US011034675B2

(12) United States Patent
Chennuru et al.

(10) Patent No.: US 11,034,675 B2
(45) Date of Patent: Jun. 15, 2021

(54) SOLID FORMS OF SELINEXOR AND PROCESS FOR THEIR PREPARATION

(71) Applicant: DR. REDDY'S LABORATORIES LIMITED, Hyderabad (IN)

(72) Inventors: Ramanaiah Chennuru, Nellore (IN); Satarupa Bhattacharjee, Howrah (IN); Srinivas Oruganti, Hyderabad (IN); Vishnu Vardhana Verna Reddy Eda, Hyderabad (IN); Ramesh Chakka, Hyderabad (IN); Vishweshwar Peddy, Hyderabad (IN); Srividya Ramakrishnan, Hyderabad (IN); Vamsi Krishna Mudapaka, Khammam (IN)

(73) Assignee: DR. REDDY'S LABORATORIES LIMITED, Hyderabad (IN)

( * ) Notice: Subject to any disclaimer, the term of this patent is extended or adjusted under 35 U.S.C. 154(b) by 0 days.

(21) Appl. No.: 16/068,552

(22) PCT Filed: Jan. 6, 2017

(86) PCT No.: PCT/IB2017/050047
§ 371 (c)(1),
(2) Date: Jul. 6, 2018

(87) PCT Pub. No.: WO2017/118940
PCT Pub. Date: Jul. 13, 2017

(65) Prior Publication Data
US 2019/0023693 A1   Jan. 24, 2019

(30) Foreign Application Priority Data

| Jan. 8, 2016 | (IN) | 201641000711 |
| May 3, 2016 | (IN) | 201641015422 |
| Nov. 4, 2016 | (IN) | 201641037733 |
| Dec. 7, 2016 | (IN) | 201641041753 |

(51) Int. Cl.
*C07D 403/12*     (2006.01)
*C07D 249/08*     (2006.01)

(52) U.S. Cl.
CPC ......... *C07D 403/12* (2013.01); *C07D 249/08* (2013.01); *C07B 2200/13* (2013.01)

(58) Field of Classification Search
None
See application file for complete search history.

(56) References Cited

U.S. PATENT DOCUMENTS

| 8,999,996 B2 | 4/2015 | Sandanayaka et al. |
| 2015/0274698 A1 | 10/2015 | Sandanayaka et al. |
| 2018/0215733 A1* | 8/2018 | Austad ................ C07D 403/12 |
| 2019/0336499 A1* | 11/2019 | Muthusamy ............ A61P 35/00 |

FOREIGN PATENT DOCUMENTS

WO   2016025904 A1   2/2016

OTHER PUBLICATIONS

International Search Report dated May 5, 2017, for corresponding International Patent Application No. PCT/IB2017/050047.
Written Opinion dated May 5, 2017, for corresponding International Patent Application No. PCT/IB2017/050047.
International Preliminary Report on Patentability dated Jul. 10, 2018, for corresponding International Patent Application No. PCT/IB2017/050047.

* cited by examiner

*Primary Examiner* — Po-Chih Chen
(74) *Attorney, Agent, or Firm* — Pergament & Cepeda LLP; Milagros A. Cepeda; Edward D. Pergament

(57) ABSTRACT

Aspects of the present application relate to solid forms of Selinexor, processes for their preparation and pharmaceutical compositions thereof. Specific aspects relate to crystalline and amorphous forms of Selinexor.

16 Claims, 11 Drawing Sheets

Position [°2Theta] (Copper(Cu))

Position [°2Theta] (Copper(Cu))

Position [°2Theta] (Copper(Cu))

Position [°2Theta] (Copper(Cu))

Position [°2Theta] (Copper(Cu))

Position [°2Theta] (Copper(Cu))

Position [°2Theta] (Copper(Cu))

Position [°2Theta] (Copper(Cu))

Position [°2Theta] (Copper(Cu))

Position [°2Theta] (Copper(Cu))

Position [°2Theta] (Copper(Cu))

Position [°2Theta] (Copper(Cu))

Position [°2Theta] (Copper(Cu))

Position [°2Theta] (Copper(Cu))

SOLID FORMS OF SELINEXOR AND PROCESS FOR THEIR PREPARATION

This application is a National Stage Application under 35 U.S.C. § 371 of PCT International Application No. PCT/IB2017/050047, filed Jan. 6, 2017, which is hereby incorporated by reference in its entirety, which PCT/IB2017/050047 application takes priority from Indian Provisional Application Numbers IN 201641000711, filed Jan. 8, 2016; IN 201641015422, filed May 3, 2016; IN 201641037733, filed Nov. 4, 2016; and IN 201641041753, filed Dec. 7, 2016.

INTRODUCTION

Aspects of the present application relate to solid forms of Selinexor, processes for their preparation and pharmaceutical compositions thereof. Specific aspects relate to crystalline and amorphous forms of Selinexor.

The drug compound having the adopted name "Selinexor" has chemical name: (Z)-3-(3-(3,5-bis(trifluoromethyl)phenyl)-IH—I,2,4-triazol-1-yl)-N'-(pyrazin-2yl) acrylohydrazide as below.

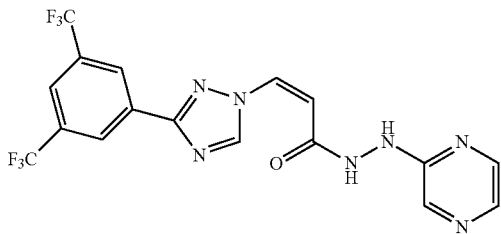 [SMILES: O=C(/C=C\n1cnc(-c2cc(C(F)(F)F)cc(C(F)(F)F)c2)n1)NNc1cnccn1]

Selinexor (KPT-330) is a first-in-class, oral Selective Inhibitor of Nuclear Export/SINE™ compound. Selinexor functions by binding with and inhibiting the nuclear export protein XPO1 (also called CRM1), leading to the accumulation of tumor suppressor proteins in the cell nucleus. This reinitiates and amplifies their tumor suppressor function and is believed to lead to the selective induction of apoptosis in cancer cells, while largely sparing normal cells. Over 1,200 patients have been treated with Selinexor in company and investigator-sponsored Phase 1 and Phase 2 clinical trials in advanced hematologic malignancies and solid tumors. Karyopharm has initiated four later-phase clinical trials of Selinexor, including one in older patients with acute myeloid leukemia (SOPRA), one in patients with Richter's transformation (SIRRT), one in patients with diffuse large B-cell lymphoma (SADAL) and a single-arm trial of Selinexor and lose-dose dexamethasone in patients with multiple myeloma (STORM). Patients may receive a twice-weekly combination of Selinexor in combination with low dose dexamethasone. Randomized 1:1, Selinexor will be dosed either at 60 mg+dexamethasone or at 100 mg+dexamethasone.

U.S. Pat. No. 8,999,996 B2 discloses Selinexor and a pharmaceutically acceptable salt thereof, pharmaceutical compositions and use for treating disorders associated with CRM1 activity. Further, it discloses preparative methods for the preparation of compounds disclosed therein including Selinexor by reacting (Z)-3-(3-(3,5-bis(trifluoromethyl)phenyl)-IH—I,2,4-triazol-1-yl)acrylic acid in 1:1 $CH_2Cl_2$:AcOEt with 2-Hydrazinopyrazine at −40° C. followed by addition of $T_3P$[Propylphosphonic anhydride] (50%) and DIPEA. After 30 minutes, the reaction mixture was concentrated and the crude oil was purified by preparative TLC using 5% MeOH in $CH_2Cl_2$ as mobile phase (under ammonia atmosphere) to afford 40 mg of Selinexor with purity: 95.78%. However, it is not disclosed about the nature of the compound obtained therein.

WO 2016025904 A1 discloses various crystalline forms of Selinexor namely Form A, Form B, Form C, Form D, compositions and MoU thereof for the treatment of disorder associated with CRM1 activity and their preparative processes.

Prior art process for the preparation of Selinexor suffers from disadvantages interms of process such as the use of lengthy procedures to practice and resulting in low yields, which may not be viable at industrial scale. Synthetic product obtained therein has very low purity and contains significant amounts of unreacted starting materials and trans-isomer of Selinexor, which are further purified by time consuming and expensive chromatographic separations leading to loss of yield. Hence, there remains a need for improved process for the preparation of Selinexor which is industrially viable and reproducible. Particularly, it is desirable to have a process avoiding purification steps still meeting desired pharmaceutical quality.

In general, polymorphism refers to the ability of a substance to exist as two or more crystalline phases that have different spatial arrangements and/or conformations of molecules in their crystal lattices. Thus, "polymorphs" refer to different crystalline forms of the same pure substance in which the molecules have different spatial arrangements of the molecules, atoms, and/or ions forming the crystal. Different polymorphs may have different physical properties such as melting point, solubility, etc. The variation in solid forms may appreciably influence the pharmaceutical properties, such as bioavailability, handling properties, dissolution rate, and stability, and in turn such properties may significantly influence the processing, shelf life, and commercial acceptance of a polymorphic form.

For these reasons, the drug manufacturing companies put efforts into identifying all polymorphic forms of new drug substances e.g., crystalline, amorphous, solvates, stable dispersions with a pharmaceutically acceptable carriers. The existence and possible numbers of polymorphic forms for a given compound may not be predicted, and there are no "standard" procedures that may be used to prepare polymorphic forms of a substance. This is well-known in the art, as reported, for example, by A. Goho, "Tricky Business," Science News, Vol. 166(8), August 2004.

There remains a need for the identification of stable and commercially viable solid form of Selinexor with characteristics suitable to formulate a dosage form. Particularly, it is desirable to have a reproducible crystalline form of Selinexor and process for its preparation. Further, need for the identification of a solid form with suitable physical properties, which may lead to its selection as the final drug substance for pharmaceutical dosage form development. Particularly, it is desirable to have an amorphous form or a crystalline form of drug to meet the needs of drug development and reproducible process for their preparation.

SUMMARY

In an aspect, the present application provides an improved process for the preparation of Selinexor, comprising the steps of:
  a) N-alkylation of triazole compound of formula (II) to obtain the N-alkylated ester of formula (IV), wherein X may be hydrogen, Y may be a leaving group such as a halogen or a sulphonate group (or) X and Y may together form a triple bond between carbons atoms to which there are linked and R may be an optionally substituted alkyl, optionally substituted aryl, optionally substituted arylalkyl, optionally substituted heteroaryl group;

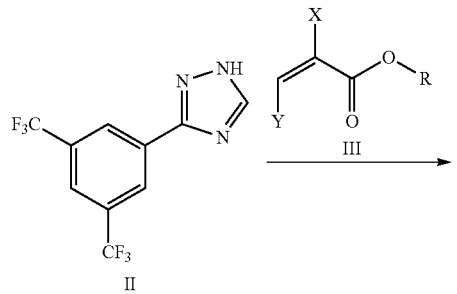

II + III b) optionally purifying the N-alkylated ester of formula (IV);
c) hydrolysis of the N-alkylated ester of formula (IV) of step a) or step b) to corresponding N-alkylated acid of formula (IVa);

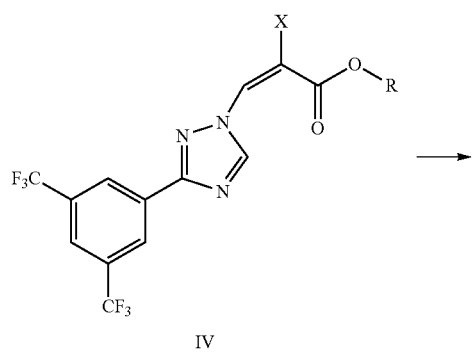

IV → IVa d) purifying the N-alkylated acid of formula (IVa) through formation of its addition salt of formula (VI), wherein B is a base;

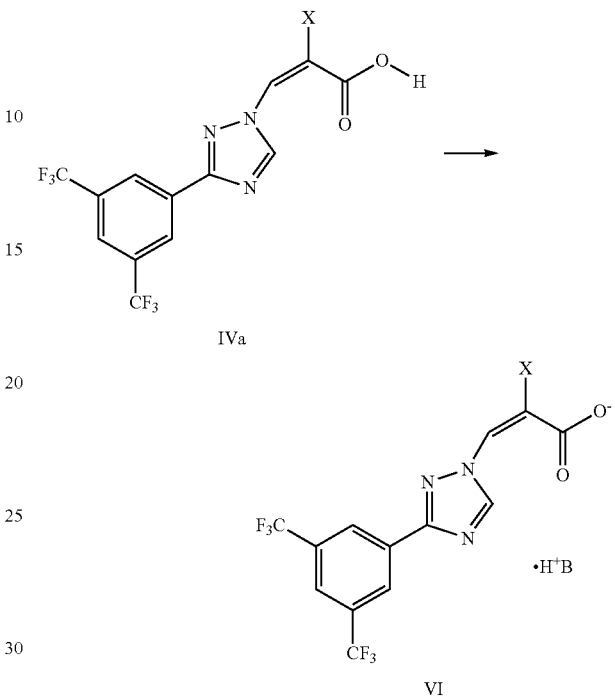

IVa → VI e) converting the addition salt of formula (VI) or N-alkylated acid of formula (IVa) to Selinexor of formula (I), wherein Z may be hydrogen or a protecting group.
f) optionally, removing the protecting group to obtain Selinexor.

In another aspect, the present application provides a process for the preparation of Selinexor or a salt thereof, comprising the steps of:

a) N-alkylation of triazole compound of formula (II) to obtain the N-alkylated ester of formula (IV), wherein X may be hydrogen and Y may be a leaving group such as a halogen or a sulphonate group (or) X and Y together form a triple bond between carbons atoms to which there are linked, R may be an optionally substituted alkyl, optionally substituted aryl, optionally substituted arylalkyl, optionally substituted heteroaryl group;

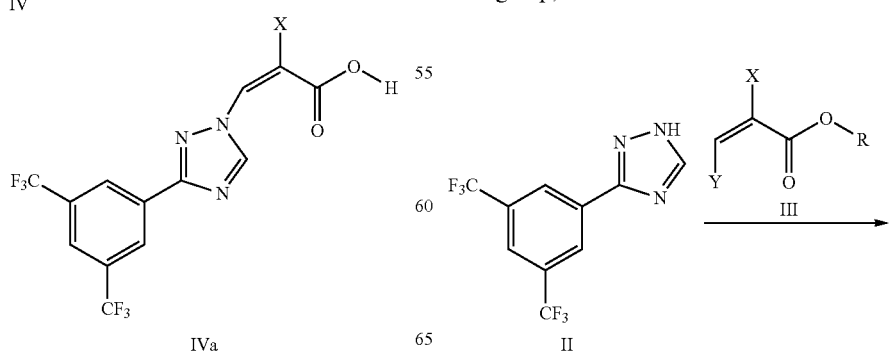

II + III

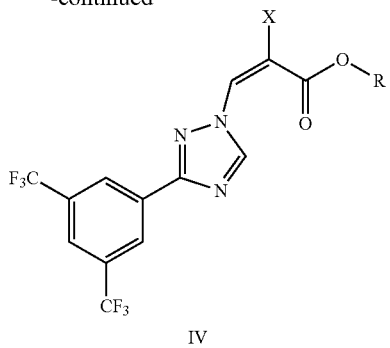

IV b) optionally purifying the N-alkylated ester of formula (IV) of step a);
c) reacting the N-alkylated ester of step a) or step b) with 2-Hydrazinopyrazine derivative of formula V, wherein Z may be hydrogen or protecting group to obtain Selinexor of formula I.

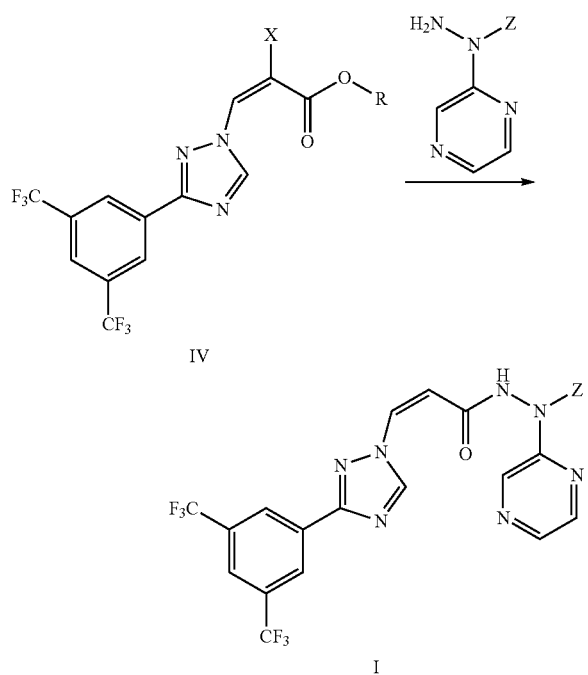

d) Optionally, removing the protecting group to obtain Selinexor.
e) purifying the Selinexor obtained in step c) or d).

In another aspect, the present application provides an addition salt of N-alkylated acid of formula VI.

In another aspect, the present application provides a process for the preparation of Selinexor comprising the step of preparing an addition salt of N-alkylated acid of formula VI.

In another aspect, the present application provides a pharmaceutical composition comprising Selinexor obtained according any of the aspects of this application and at least one pharmaceutically acceptable excipient.

In another aspect, the present application provides crystalline Form-Alpha of Selinexor, characterized by a PXRD pattern comprising the peaks at about 4.38, 12.45, 13.13, 15.85, 19.98 and 21.35 ±0.2° 2θ. In an embodiment, the application provides crystalline form Alpha of Selinexor, characterized by a PXRD pattern having one or more additional peaks at about 14.51, 14.77, 20.30 and 27.32 ±0.2° 2θ.

In another aspect, the present application provides crystalline Form-Beta of Selinexor, characterized by a PXRD pattern comprising the peaks at about 5.87, 11.73, 18.71, 20.53 and 24.05 ±0.2° 2θ. In an embodiment, the application provides crystalline Form-Beta of Selinexor, characterized by a PXRD pattern having one or more additional peaks at about 16.28 and 21.28 ±0.2° 2θ.

In another aspect, the present application provides crystalline Form-Gamma of Selinexor, characterized by a PXRD pattern comprising the peaks at about 3.28, 11.95, 14.62, 15.74 and 20.96 ±0.2° 2θ. In an embodiment, the application provides crystalline Form-Gamma of Selinexor, characterized by a PXRD pattern having one or more additional peaks at about 16.95, 18.23, 20.01 and 22.13 ±0.2° 2θ.

In another aspect, the present application provides crystalline Form-Delta of Selinexor, characterized by a PXRD pattern comprising the peaks at about 6.11, 12.16, 13.00, 20.28 and 24.43 ±0.2° 2θ. In an embodiment, the application provides crystalline Form-Delta of Selinexor, characterized by a PXRD pattern having one or more additional peaks at about 19.35, 23.39 and 23.78 ±0.2° 2θ.

In another aspect, the present application provides crystalline Form-Epsilon of Selinexor, characterized by a PXRD pattern comprising the peaks at about 5.87, 11.72, 17.61, 18.68, 20.50, 22.78, 23.20, 23.53 and 23.97 ±0.2° 2θ. In an embodiment, the application provides crystalline Form-Epsilon of Selinexor, characterized by a PXRD pattern having one or more additional peaks at about 16.26, 21.25, 25.35, 29.22 and 30.14±0.2° 2θ.

In another aspect, the present application provides crystalline Form-Zeta of Selinexor, characterized by a PXRD pattern comprising the peaks at about 4.86, 6.99, 7.74, 10.86, 15.50 and 19.47 ±0.2° 2θ. In an embodiment, the application provides crystalline Form-Zeta of Selinexor, characterized by a PXRD pattern having one or more additional peaks at about 14.00, 18.27, 20.73, 21.51 and 22.14 ±0.2° 2θ.

In another aspect, the present application provides crystalline Form-Eta of Selinexor, characterized by a PXRD pattern comprising the peaks at about 3.54, 7.03, 9.91, 11.59, 19.84, 20.44 and 21.64 ±0.2° 2θ. In an embodiment, the application provides crystalline Form-Eta of Selinexor, characterized by a PXRD pattern having one or more additional peaks at about 17.55, 21.09, 22.45 and 23.28 ±0.2° 2θ.

In another aspect, the present application provides crystalline Form-Theta of Selinexor, characterized by a PXRD pattern comprising the peaks at about 6.96, 13.92, 20.95 and 22.82 ±0.2° 2θ. In an embodiment, the application provides crystalline Form-Theta of Selinexor, characterized by a PXRD pattern having one or more additional peaks at about 17.24, 20.03, 20.37 and 23.41 ±0.2° 2θ.

In another aspect, the present application provides crystalline Form-Iota of Selinexor, characterized by a PXRD pattern comprising the peaks at about 3.69, 7.33, 11.01, 14.66, 16.19 and 18.36 ±0.2° 2θ.

In another aspect, the present application provides crystalline Form-Kappa of Selinexor, characterized by a PXRD pattern comprising the peaks at about 3.22, 11.71, 12.56, 14.42 and 25.20 ±0.2° 2θ.

In another aspect, the present application provides crystalline Form-Lambda of Selinexor, characterized by a PXRD pattern comprising the peaks at about 12.61, 19.00, 19.95 and 21.29 ±0.2° 2θ. The application provides crystalline Form-Lambda of Selinexor, characterized by a PXRD pattern having one or more additional peaks at about 14.13, 21.29, 21.75, 23.10, 24.65 and 30.86 ±0.2° 2θ.

In another aspect, the present application provides crystalline Form-Mu of Selinexor, characterized by a PXRD pattern comprising the peaks at about 9.31, 17.45, 17.85 and 22.72 ±0.2° 2θ. In an embodiment, the application provides crystalline Form-Mu of Selinexor, characterized by a PXRD pattern having one or more additional peaks at about 21.20, 25.01 and 27.59 ±0.2° 2θ.

In another aspect, the present application provides crystalline Form-Nu of Selinexor, characterized by a PXRD pattern comprising the peaks at about 10.75, 17.52, 21.84, 22.16 and 22.38 ±0.2° 2θ. In an embodiment, the application provides crystalline Form-Nu of Selinexor, characterized by a PXRD pattern having one or more additional peaks at about 18.30, 24.53 and 28.91 ±0.2° 2θ.

In another aspect, the present application provides crystalline Form-Xi of Selinexor, characterized by a PXRD pattern comprising the peaks at about 10.54, 11.68, 12.72 and 24.56 ±0.2° 2θ. In an embodiment, the application provides crystalline Form-Xi of Selinexor, characterized by a PXRD pattern having one or more additional peaks at about 3.70, 7.36, 18.10, 19.72 and 21.21 ±0.2° 2θ.

In another aspect, the present application provides an amorphous form of Selinexor.

In another aspect, the present application provides a pharmaceutical composition comprising amorphous form of Selinexor combined with at least one pharmaceutically acceptable excipient.

In another aspect, the present application provides amorphous solid dispersion of Selinexor together with at least one pharmaceutically acceptable excipient.

In another aspect, the present application provides a pharmaceutical composition comprising amorphous solid dispersion of Selinexor combined with at least one additional pharmaceutically acceptable excipient.

In another aspect, the present application provides process for preparing a crystalline form of Selinexor, which comprises:
  a) combining amorphous Selinexor with a solvent or a mixture thereof;
  b) stirring the mixture of step a);
  c) optionally adding an anti-solvent to the mixture of step a) or b)
  d) isolating crystalline form of Selinexor.

In another aspect, the present application provides a process for the preparation of crystalline form of Selinexor or a solvate thereof, comprising the step of converting amorphous Selinexor to crystalline form of Selinexor or a solvate thereof.

In another aspect, the present application provides process for preparing a crystalline Form-Alpha of Selinexor, which comprises:
  a) combining Selinexor with acetone: water mixture;
  b) stirring the mixture of step a);
  c) isolating crystalline Form-Alpha of Selinexor.

In another aspect, the present application provides process for preparing a crystalline Form-Delta of Selinexor, which comprises:
  a) combining Selinexor with methanol;
  b) stirring the mixture of step a);
  c) isolating crystalline Form-Delta of Selinexor.

In another aspect, the present application provides process for preparing a crystalline Form-Epsilon of Selinexor, which comprises:
  a) combining Selinexor with ethanol;
  b) stirring the mixture of step a);
  c) isolating crystalline Form-Epsilon of Selinexor.

In another aspect, the present application provides process for preparing a crystalline Form-Zeta of Selinexor, which comprises:
  a) combining Selinexor with acetic acid and water;
  b) stirring the mixture of step a);
  c) isolating crystalline Form-Zeta of Selinexor.

In another aspect, the present application provides process for preparing a crystalline Form-Eta of Selinexor, which comprises:
  a) combining Selinexor with nitromethane;
  b) stirring the mixture of step a);
  c) isolating crystalline Form-Eta of Selinexor.

In another aspect, the present application provides process for preparing a crystalline Form-Theta of Selinexor, which comprises:
  a) providing a solution of Selinexor in formic acid;
  b) contacting the solution of step a) with an anti-solvent;
  c) isolating crystalline Form-Theta of Selinexor.

In another aspect, the present application provides process for preparing a crystalline Form-Iota of Selinexor, which comprises the step of drying Form-Eta of Selinexor.

In another aspect, the present application provides process for preparing a crystalline Form-Kappa of Selinexor, which comprises:
  a) combining Selinexor with water;
  b) stirring the mixture of step a);
  c) isolating crystalline Form-Kappa of Selinexor.

In another aspect, the present application provides process for preparing a crystalline Form-Lambda of Selinexor, which comprises:
  a) combining Selinexor with glycerol;
  b) stirring the mixture of step a);
  c) isolating crystalline Form-Lambda of Selinexor.

In another aspect, the present application provides process for preparing a crystalline Form-Mu of Selinexor, which comprises:
  a) combining Selinexor with dimethyl formamide;
  b) stirring the mixture of step a);
  c) isolating crystalline Form-Mu of Selinexor.

In another aspect, the present application provides process for preparing a crystalline Form-Nu of Selinexor, which comprises:
  a) combining Selinexor with dimethylacetamide;
  b) stirring the mixture of step a);
  c) isolating crystalline Form-Nu of Selinexor.

In another aspect, the present application provides process for preparing a crystalline Form-Xi of Selinexor, which comprises the step of drying Form-kappa of Selinexor.

In another aspect, the present application provides process for preparing a crystalline Form-Kappa of Selinexor, which comprises:
  a) providing a solution of Selinexor in methanol or a mixture thereof;
  b) contacting the solution of step a) with water;
  c) isolating crystalline Form-Kappa of Selinexor.

In another aspect, the present application provides a process for the preparation of an amorphous form of Selinexor, comprising the steps of:
  a) providing a solution of Selinexor in a solvent or a mixture thereof;
  b) removing the solvent from the solution obtained in step a); and
  c) isolating the amorphous form of Selinexor.

d) optionally combining amorphous form of step c) with at least one pharmaceutically acceptable excipient.

In another aspect, the present application provides a process for the preparation of an amorphous solid dispersion of Selinexor, comprising the steps of:
a) providing a solution of Selinexor and at least one pharmaceutically acceptable excipient in a solvent or a mixture thereof;
b) removing the solvent from the solution obtained in step a), and
c) isolating the amorphous solid dispersion of Selinexor.
d) optionally combining amorphous solid dispersion of step c) with at least one additional pharmaceutically acceptable excipient.

In another aspect, the present application provides a pharmaceutical composition comprising the any of the solid forms of Selinexor described in the specification and at least one pharmaceutically acceptable excipient. In embodiments, the present application provides a pharmaceutical composition comprising amorphous form, its solid dispersion or crystalline forms of Selinexor and at least one pharmaceutically acceptable excipient.

In another aspect, the present application provides pharmaceutical composition comprising Selinexor and at least one pharmaceutically acceptable excipient, wherein Selinexor may be selected from group comprising of crystalline Form-Alpha, Form-Beta, Form-Gamma, Form-Delta, Form-Epsilon, Form-Zeta, Form-Eta, Form-Theta, Form-Iota, Form-Kappa, Form-Lambda, Form-Mu, Form-Nu and Form-Xi of Selinexor or mixtures thereof.

BRIEF DESCRIPTION OF THE DRAWING

According to National Institute of Standards and Technology (NIST), for silica powder, one of the PXRD peak position is at 28.44° (2θ). Silica powder was spiked to all the crystalline forms (Forms-Alpha, Beta and Gamma) of Selinexor in order to obtain accurate PXRD peak positions. In FIGS. 1 to 4, peak at 28.44° (2θ) corresponds to silica powder.

DETAILED DESCRIPTION

Figure 1:
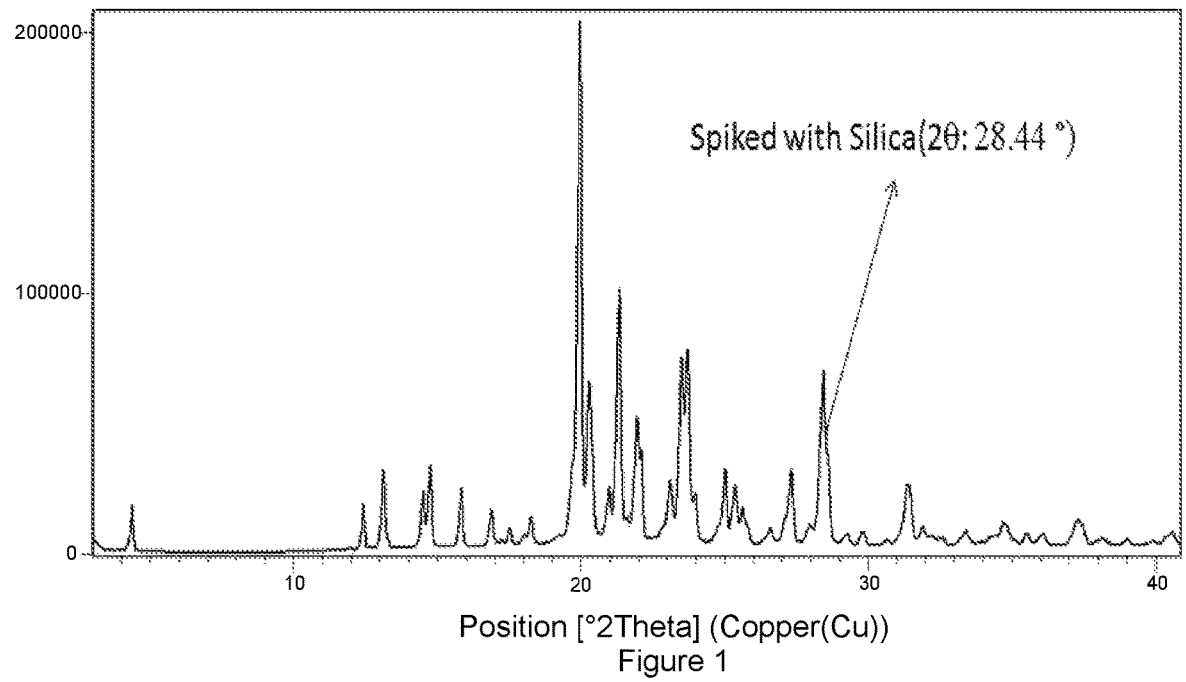
FIG. 1 is an illustrative X-ray powder diffraction pattern of crystalline Form-Alpha of Selinexor prepared by the method of Example No 4.

In an aspect, the present application provides an improved process for the preparation of Selinexor, comprising the steps of:
a) N-alkylation of triazole compound of formula (II) to obtain the N-alkylated ester of formula (IV), wherein X may be hydrogen, Y may be a leaving group such as a halogen or a sulphonate group (or) X and Y may together form a triple bond between carbons atoms to which there are linked and R may be an optionally substituted alkyl, optionally substituted aryl, optionally substituted arylalkyl, optionally substituted heteroaryl group;

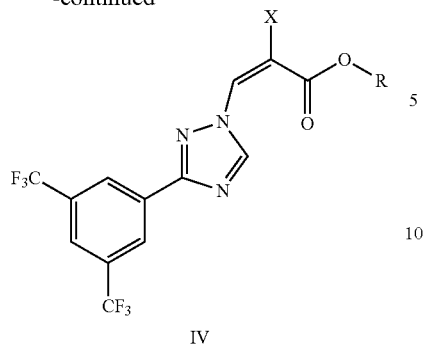

IV b) optionally purifying the N-alkylated ester of formula (IV);
c) hydrolysis of the N-alkylated ester of formula (IV) of step a) or step b) to corresponding N-alkylated acid of formula (IVa);

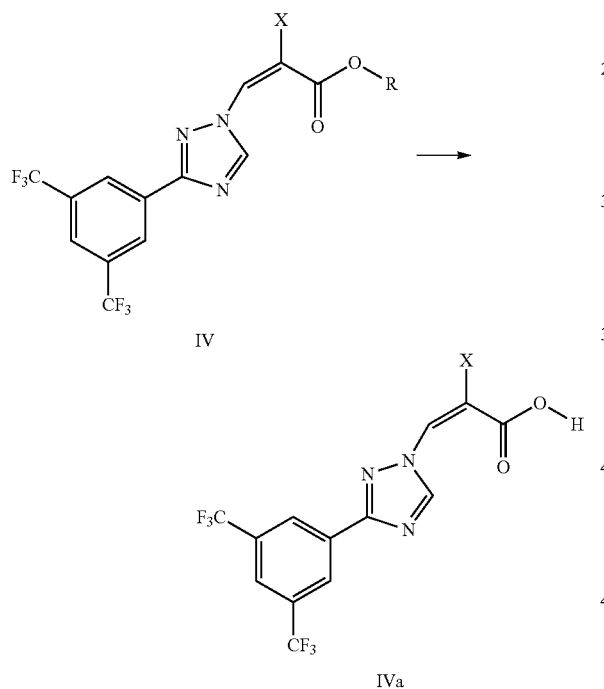

d) purifying the N-alkylated acid of formula (IVa) through formation of its addition salt of formula (VI), wherein B is a base;

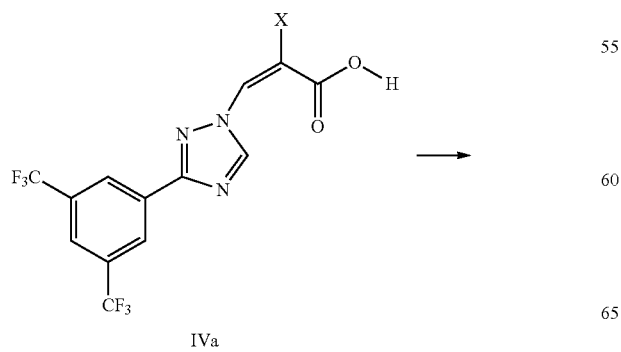

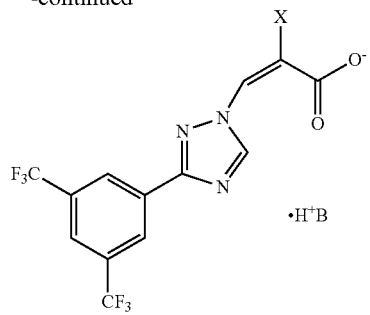

VI e) converting the addition salt of formula (IV) or N-alkylated acid of formula (IVa) to Selinexor of formula (I), wherein Z may be hydrogen or a protecting group.
f) optionally, removing the protecting group to obtain Selinexor.

The individual steps of the process are described herein below.

Starting materials, triazole compound of formula (II) and ester compound of formula (III) are either commercially available or may be prepared by the procedures known in art or the procedures described and exemplified in present application.

The starting materials can be purified by techniques known in art like column chromatography, fractional distillation, acid-base treatment, slurring or re-crystallization, before using.

In an embodiment, step a) may be carried out by N-alkylation of triazole compound of formula (II) with an ester compound of formula (III) to obtain the N-alkylated ester of formula (IV), wherein X may be hydrogen, Y may be a leaving group such as a halogen or a sulphonate group (or) X and Y may together form a triple bond between carbons atoms to which there are linked and R may be an optionally substituted alkyl, optionally substituted aryl, optionally substituted arylalkyl, optionally substituted heteroaryl group.

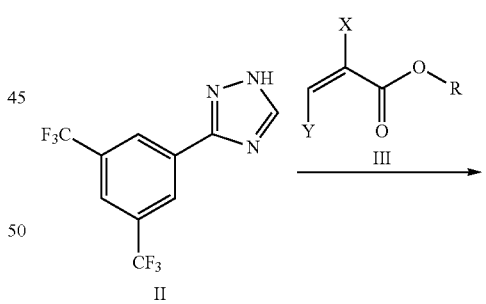

In an embodiment, N-alkylation of triazole compound of formula (II) may be carried out in the presence of a base. Base may be selected from the group consisting of 1,8-diazabicyclo[5.4.0]undec-7-ene (DBU), 1,5-diazabicyclo[4.3.0]non-5-ene(DBN), 1,4-diazabicyclo(2.2.2)octane (DABCO), N,N-dicyclohexylmethylamine, 2,6-di-tert-butyl-4-methylpyridine, quinuclidine, 1,2,2,6,6-pentamethylpiperidine (PMP), 7-methyl-1,5,7-triazabicyclo(4.4.0)dec-5-ene (MTBD), triphenylphosphine, tri-tert-butylphosphine, tricyclohexylphosphine, triethylamine, diisopropyl amine or the like.

In an embodiment, N-alkylation of triazole compound of formula (II) may be carried out in the presence of a suitable solvent. Suitable solvent may include, but not limited to ether solvent such as tetrahydrofuran, dioxane; ketone solvent such as acetone, methyl ethyl ketone, methyl isobutyl ketone; ester solvent such as ethyl acetate, isopropyl acetate; alcohol solvent such as methanol, ethanol, isopropyl alcohol, butanol; nitrile solvent such as acetonitrile; halogenated hydrocarbons such as dichloromethane; water and the like.

In an embodiment, N-alkylation of triazole compound of formula (II) may be carried out at suitable temperature at about −30° C. to reflux temperature of the solvent used. In preferred embodiment, N-alkylation may be carried out at about −10° C. to 50° C.

In an embodiment, N-alkylation of triazole compound of formula (II) may be carried out for sufficient time to complete alkylation of triazole compound. In preferred embodiment, N-alkylation may be carried out for at least 30 minutes or more.

In an embodiment, step b) of this aspect may be carried out by optionally purifying N-alkylated ester of formula (IV) before proceeding to next step. In an embodiment N-alkylated ester may be purified by methods known in the art such as chromatographic separations, fractional distillation, acid-base treatment, recrystallization, slurry or procedures described or exemplified in the present application.

In an embodiment, N-alkylated ester of formula (IV) may be purified by chromatographic separations, recrystallizing or slurrying in a solvent or mixture of solvents.

In an embodiment, N-alkylated ester of formula (IV) may be purified by recrystallizing or slurrying in a solvent or mixture of solvents. In embodiments, the recrystallization or slurrying of N-alkylated ester may be repeated to attain desired quality of the product. In an embodiment, the recrystallization or slurrying of N-alkylated ester may be repeated to obtain substantially single isomer i.e., cis-isomer of N-alkylated ester of formula (IV). It is evident from the exemplification of the present application, that the unwanted trans-isomer of the N-alkylated ester of formula (IV) has been well controlled with this purification method.

In an embodiment, N-alkylated ester of formula (IV) may be purified by slurrying it in a solvent or mixture of solvents at suitable temperature and for sufficient time to obtain the product with desired quality. In an embodiment, N-alkylated ester of formula (IV) may be slurried in the solvent at temperature of about −50° C. to about 0° C. In an embodiment, N-alkylated ester of formula (IV) may be slurried in the solvent for at least 10 minutes or more.

Solvent may include, but not limited to hydrocarbons such as hexane, cyclohexane, pentane, cyclopentane, toluene, xylene, or the like.

In a preferred embodiment, N-alkylated ester of formula (IV) may be purified by slurrying in a solvent system comprising at least one hydrocarbon solvent such as hexane, heptane or the like.

N-alkylated ester of formula (IV) or its addition salt recovered by the processes of application can be subjected to drying at suitable temperatures, such as about 30°-100° C. and suitable pressures, using drying equipment known in the art, such as air dryer, vacuum dryer, fluidized bed dryer, spin flash dryer, flash dryer, and the like. Drying can be carried out at temperatures and times sufficient to achieve desired quality of product.

Step c) of this aspect may be carried out by hydrolyzing the N-alkylated ester of formula (IV) to corresponding N-alkylated acid of formula (IVa) under suitable conditions. Hydrolysis of N-alkylated ester may be carried out according any method known in the art for ester hydrolysis or by following procedures described or exemplified in the present application.

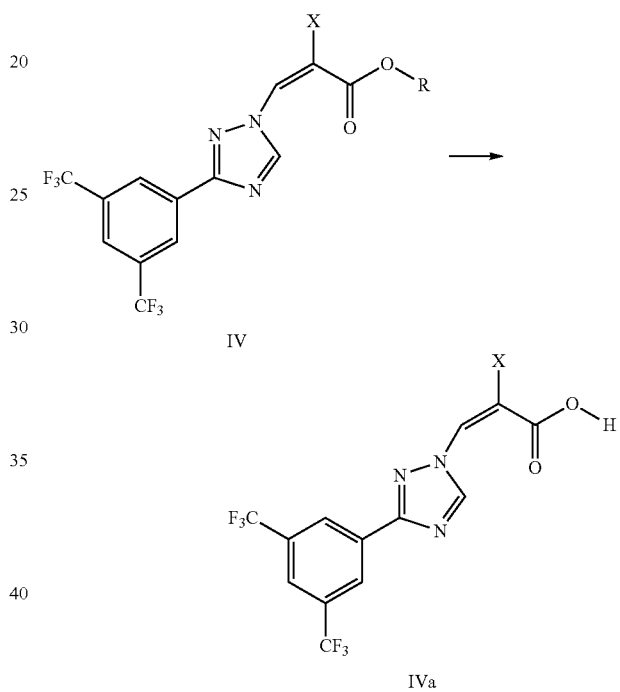

In an embodiment, N-alkylated ester may be hydrolyzed under acidic, basic or neutral conditions to obtain N-alkylated acid of formula (IVa). In preferred embodiment, the N-alkylated ester may be hydrolyzed using suitable acid or base.

Suitable acid may be selected from group comprising of inorganic or organic acid such as concentrated or diluted Hydrochloric acid, Sulphuric acid, phosphoric acid, formic acid, acetic acid, alkyl sulphonic acids or the like.

Suitable base may be selected from group comprising of hydroxides, carbonates, bicarbonates or alkoxides of alkali or alkali earth metal such as Lithium, Sodium, Potassium, Cesium, Calcium, Magnesium or the like.

Step d) of this aspect may be carried out by purification of N-alkylated acid of formula (IVa) through the formation of its addition salt of formula (VI).

Alternatively, N-alkylated acid may be purified by chromatographic separations, recrystallizing or slurrying in a solvent or mixture of solvents.

Inventors of the present application have identified, that the purity of N-alkylated acid of formula (IVa) was surprisingly enhanced to significant extent through acid-base treatment such as through formation of its salt and it is evidential as per the exemplification of the present application.

In an embodiment, N-alkylated acid of formula (IVa) may be purified comprising the steps of
I. converting the N-alkylated acid of formula (IVa) to its addition salt of N-alkylated acid of formula (VI), wherein B is a base.
II. neutralizing this addition salt to obtain pure N-alkylated acid of formula IVa;

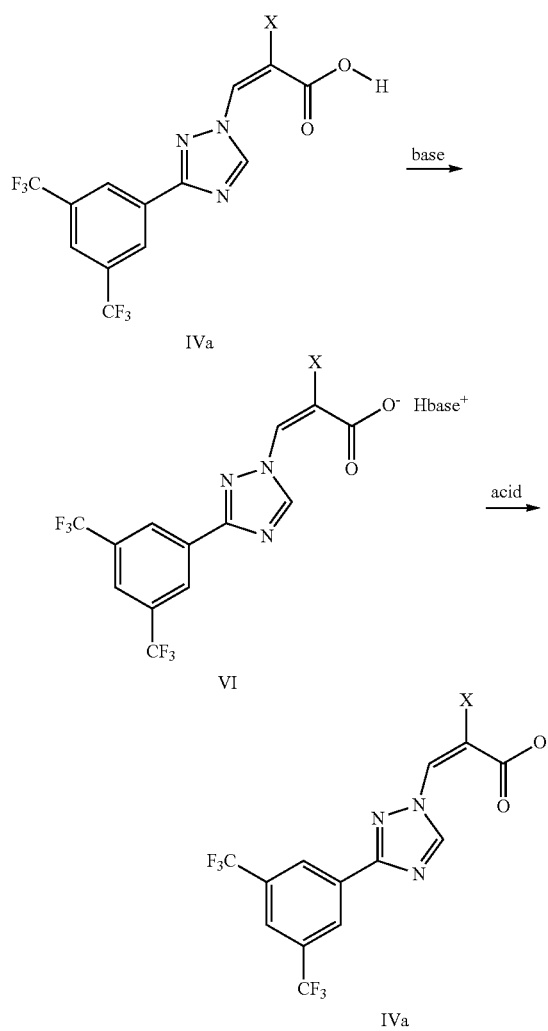

In an embodiment, N-alkylated acid of formula (IVa) may be treated with a base to obtain an addition salt thereof under suitable conditions. Base may be a inorganic or organic base selected from the group comprising of hydroxides, carbonates, alkoxides, bicarbonates of alkali metals, alkaline earth metals, non-toxic metals, ammonium for example the sodium, potassium, lithium, calcium, magnesium, aluminum, zinc, ammonium trimethylammonium, triethanolammonium, Pyridinium, substituted Pyridinium salts; mono-, di- and trisubstituted amines such as, Dicyclohexylamine (DCHA), tert-Butyl amine, diethyl amine, dibutylamine, Morpholine, 3-diemthylamino-1-propylamine, diisopropyl amine, N-tert-butylbenzylamine, N-benzylmethylamine, α-Methyl benzyl amine, (s)-α-methyl benzylamine, benzyl amine, dibenzylamine, cyclohexyl amine, tert-octylamine. Tris(hydroxymethyl)aminomethane, 2-Amino-2-methyl-1-propanol, 2-Amino-2-methyl-1,3-propanediol, 2,2'-(Propane-1,3-diyldiimino)bis[2-(hydroxymethyl) propane-1,3-diol],2-[Bis(2-hydroxyethyl)imino]-2-(hydroxymethyl)-1,3-propanediol, 2-Aminoethanol, (2R,3R,4R,5S)-6-Methylaminohexane-1,2,3,4,5-pentol, 2,2',2"-Nitrilotriethanol or the like.

In an embodiment, N-alkylated acid may be treated with the base in the presence of a solvent or mixture of solvents. In an embodiment, the mixture of N-alkylated acid of formula (IVa) and the solvent may be either homogenous or heterogeneous. Solvent that are disclosed in any aspect of the present application may be used for the purification of N-alkylated acid of formula (IVa).

In an embodiment, N-alkylated acid of formula (IVa) may be treated with the base for sufficient time and suitable temperature to complete formation of its addition salt.

In an embodiment, base may be treated with N-alkylated acid by adding the base for sufficient time either gradually in a single lot or periodically in multiple lots. Base may be treated directly or in diluted state in a solvent.

In an embodiment, base may be treated with N-alkylated acid at suitable temperature of about 0° C. to reflux temperature of the reaction mixture. In preferred embodiment, base treatment may be carried out at 0° C. to 60° C.

In an embodiment, the addition salt of N-alkylated acid of formula (VI) may be isolated by any methods known in the art or by following the procedures described or exemplified in the present application. In embodiments, the addition salt of N-alkylated acid may be isolated by cooling crystallization, anti-solvent addition or evaporation of the solvent or combinations thereof.

In an embodiment, the addition salt of N-alkylated acid may be neutralized before proceeding to next step (or) the addition salt of N-alkylated acid of formula (VI) may be directly used in the next step for the preparation of Selinexor of formula I.

In an embodiment, the addition salt of N-alkylated acid of formula (VI) may be neutralized with an acid to obtain pure N-alkylated acid. Acid may be selected from the group comprising of inorganic or organic acids such as hydrochloric acid, hydrobromic acid, sulphuric acid, phosphoric acid, Perchloric acid, formic acid, acetic acid, alkyl or aryl sulphonic acid or the like. Acid may be used in concentrated or in diluted state such as aqueous or alcoholic solutions.

In an embodiment, addition salt of N-alkylated acid of formula (VI) may be treated with the acid optionally in the presence of a solvent or mixture of solvents. In an embodiment, the mixture of addition salt of N-alkylated acid of formula (VI) and the solvent may be either homogenous or heterogeneous.

In an embodiment, addition salt of N-alkylated acid of formula (VI) may be treated with the acid for sufficient time and suitable temperature to complete liberation of pure N-alkylated acid of formula (IVa).

In an embodiment, acid may be treated with addition salt of formula (VI) by adding the acid for sufficient time either gradually in a single lot or periodically in multiple lots.

In an embodiment, acid may be treated with addition salt at suitable temperature of about 0° C. to reflux temperature of the reaction mixture. In preferred embodiment, base treatment may be carried out at 0° C. to 60° C.

In an embodiment, the N-alkylated acid of formula (IVa) may be isolated by any methods known in the art or by following the procedures described or exemplified in the present application. In embodiments, N-alkylated acid may be isolated by cooling crystallization, anti-solvent addition or evaporation of the solvent or combinations thereof.

In an embodiment, the N-alkylated acid of formula (IVa) or its addition salt of formula (VI) may be recovered employing any of the techniques known to a person skilled in art. Techniques for the recovering pure N-alkylate acid may include, but not limited to: decantation, filtration by gravity or suction, centrifugation, and the like, and optionally washing with a solvent.

The N-alkylate acid of formula (IVa) or its addition salt of formula (VI) recovered by the processes of application can be subjected to drying at suitable temperatures, such as about 30°–100° C. and suitable pressures, using drying equipment known in the art, such as air dryer, vacuum dryer, fluidized bed dryer, spin flash dryer, flash dryer, and the like. Drying can be carried out at temperatures and times sufficient to achieve desired quality of product.

Step e) of this aspect may be carried out by converting the addition salt of formula (IV) or N-alkylated acid of formula (IVa) to Selinexor of formula (I).

In an embodiment, N-alkylated acid of formula (IVa) may be reacted with 2-Hydrazinopyrazine derivative of formula V, wherein Z may be hydrogen or protecting group.

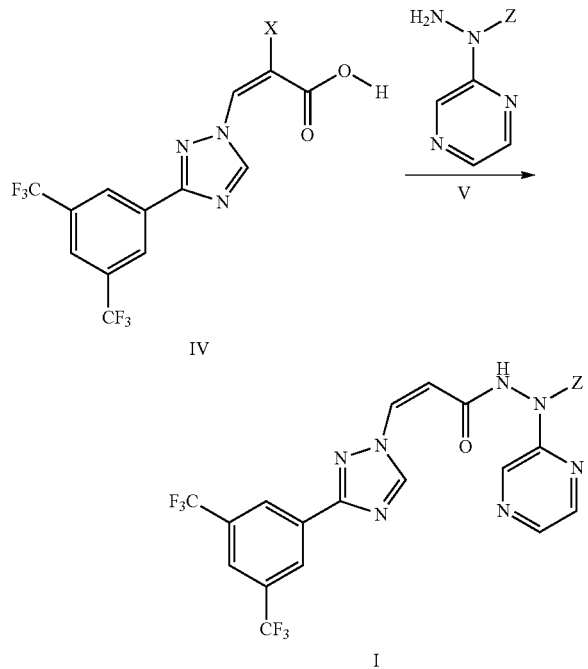

In an embodiment, step e) of this aspect may be carried out by reacting the addition salt thereof of formula (VI) with 2-Hydrazinopyrazine derivative of formula V optionally in the presence of a base according any methods known in the art or procedures described or exemplified in the present application.

In an embodiment, step e) of this aspect may be carried out by reacting N-alkylated acid of formula (IVa) with 2-Hydrazinopyrazine derivative of formula V, wherein the N-alkylated acid is either in isolated state or generated insitu without its isolation. In embodiments, the N-alkylated acid of formula (IVa) is generated insitu either by hydrolysis of corresponding ester of formula (IV) or by neutralization of corresponding addition salt of formula (VI). In embodiments, hydrolysis of the ester or neutralization of addition salt may be carried out according to the methods known in the art or procedures described or exemplified in the present application.

In an embodiment, N-alkylated acid of formula (IVa) may be reacted with 2-Hydrazinopyrazine derivative of formula V optionally in the presence of a catalyst.

Catalyst that may be used for the reaction of N-alkylated ester of formula (IV) or N-alkylated acid of formula (IVa) with 2-Hydrazinopyrazine derivative of formula V may be selected from the group comprising of pyridine, dimethyl aminopyridine, triethyl amine, diisopropyl ethyl amine, metal alkoxides such as sodiummethoxide, organoaluminium reagents such as trialkyl or triaryl aluminium, 1-hydroxy benzotriazole (HOBT), 1-Ethyl-3-(3-dimethyl-aminopropyl)carbodiimide (EDCI) OR ITS HCl salt, Carbonyldiimidazole (CDI), dicylohexylcarbodiimide, Propane Phosphonic Acid Anhydride (T$_3$P), HOBT+EDC, dicyclohexylcarbodiimide (DCC) or the like.

Step f) of this aspect may be carried out by optionally removing the protecting the group to obtain Selinexor of formula (I), wherein Z may be hydrogen. Removal of protecting group may be carried out according to methods known in the art for deprotection of nitrogen or according to the procedures described or exemplified in the present application.

Selinexor obtained according to the present aspect may be optionally purified by according to the suitable methods known in the art which include, but not limited to chromatographic separations, recrystallizing or slurrying in a solvent or mixture of solvents, acid-base treatment i.e., through salt formation or the like. Suitable acid that may be used is selected from any of the acceptable organic or inorganic acids known in the art and suitable for the formation of acid-addition salt or any acid disclosed in any aspect of the instant application.

Selinexor of formula (I) or its addition salt recovered by the processes of application can be subjected to drying at suitable temperatures, such as about 30°-100° C. and suitable pressures, using drying equipment known in the art, such as air dryer, vacuum dryer, fluidized bed dryer, spin flash dryer, flash dryer, and the like. Drying can be carried out at temperatures and times sufficient to achieve desired quality of product.

In another aspect, the present application provides a process for the preparation of Selinexor or a salt thereof, comprising the steps of:
a) N-alkylation of triazole compound of formula (II) to obtain the N-alkylated ester of formula (IV), wherein X may be hydrogen and Y may be a leaving group such as a halogen or a sulphonate group (or) X and Y together form a triple bond between carbons atoms to which there are linked, R may be an optionally substituted alkyl, optionally substituted aryl, optionally substituted arylalkyl, optionally substituted heteroaryl group;

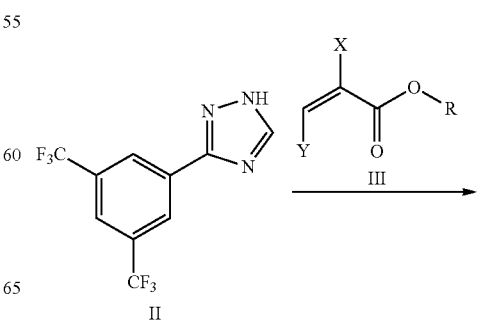

-continued

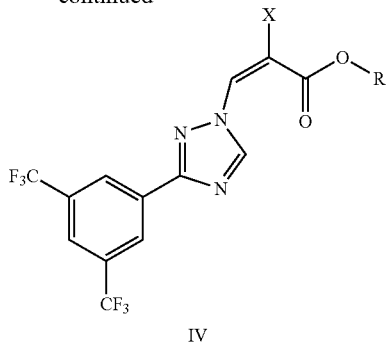

IV b) optionally purifying the N-alkylated ester of formula (IV) of step a);
c) reacting the N-alkylated ester of step a) or step b) with 2-Hydrazinopyrazine derivative of formula V, wherein Z may be hydrogen or protecting group to obtain Selinexor of formula I.

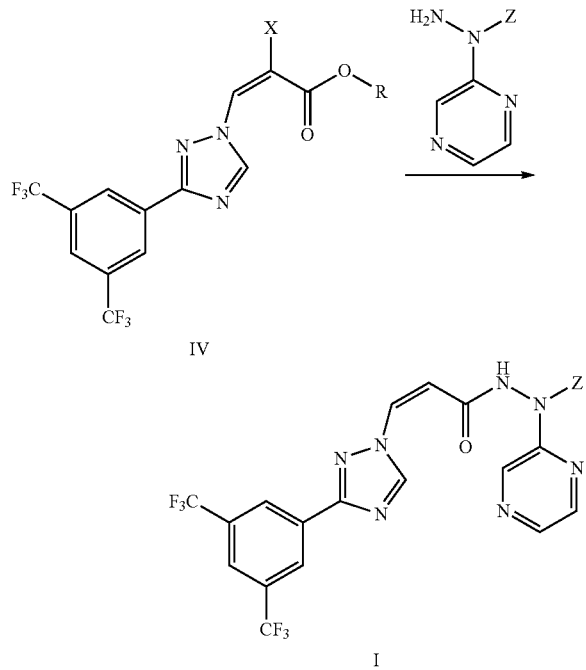

d) Optionally, removing the protecting group to obtain Selinexor.
e) purifying the Selinexor obtained in step c) or d).

Starting materials, triazole compound of formula (II) and ester compound of formula (III) are either commercially available or may be prepared by the procedures known in art or the procedures described and exemplified in present application.

The starting materials can be purified by techniques known in art like column chromatography, fractional distillation, acid-base treatment, slurrying or re-crystallization, before using.

Process of this aspect is advantageous interms of reduced number of steps for the preparation of Selinexor of formula (I). The process of this aspect avoids the step of hydrolysis of N-alkylated ester of formula (IV) and converting it directly to Selinexor of formula (I) as against the process known in the prior art.

Step a) of this aspect may be carried out by N-alkylation of triazole compound of formula (II) to obtain the N-alkylated ester of formula (IV). N-alkylation may be carried out according to any of the procedures described in any of the previous aspect or exemplified in the present application.

In embodiments, N-alkylated ester of formula (IV) may be purified using methods such as recrystallization or slurrying in a suitable solvent or mixture of solvents, chromatographic separation or acid-base treatment i.e., through salt formation and neutralization.

Step b) of this aspect may be carried out by optionally purifying the N-alkylated ester of formula (IV) according to any of the methods known in the art or procedures as described in previous aspect or exemplified in the present application. In an embodiment, purification of N-alkylated ester of formula (IV) may be carried out through the formation of its addition salt according to methods described in any aspect of the instant application.

In an alternate embodiment, the N-alkylated ester of formula (IV) may be optionally purified by slurrying in a solvent or mixture of solvents at suitable temperature and sufficient time. Solvent that may be used include, but not limited to an alcohol such as methanol, ethanol, isopropyl alcohol; an ester such as ethyl acetate, isopropyl acetate; an ketone such as acetone, methyl isobutyl ketone; hydrocarbons such as hexane, cyclohexane, pentane, cyclopentane, toluene, xylene; water or the mixtures thereof.

N-alkylated ester of formula (IV) may be purified by slurrying in a solvent or mixture of solvents for sufficient time till the desired content of either of the Cis or trans isomer is obtained. In an embodiment, N-alkylated ester of formula (IV) may be purified by slurrying at suitable temperature of about −50° C. and above.

N-alkylated ester of formula (IV) or its addition salt recovered by the processes of application can be subjected to drying at suitable temperatures, such as about 30°-100° C. and suitable pressures, using drying equipment known in the art, such as air dryer, vacuum dryer, fluidized bed dryer, spin flash dryer, flash dryer, and the like. Drying can be carried out at temperatures and times sufficient to achieve desired quality of product.

Step c) of this aspect may be carried out by reacting the N-alkylated ester of formula (IV) with 2-Hydrazinopyrazine derivative of formula V to obtain Selinexor of formula (I), wherein Z may be hydrogen or protecting group.

In an embodiment, N-alkylated ester of formula (IV) may be reacted with 2-Hydrazinopyrazine derivative of formula V, to obtain Selinexor of formula I optionally in the presence of a solvent. Any of the solvents disclosed in any aspect of the instant application may be used.

N-alkylated ester of formula (IV) may be reacted with 2-Hydrazinopyrazine derivative of formula V using any of the methods or conditions known in the art or procedures described or exemplified in this specification.

In an embodiment, N-alkylated ester of formula (IV) may be reacted with 2-Hydrazinopyrazine derivative of formula V by heating the reaction mixture. In an embodiment, the reaction mixture may be heated to about 50° C. to reflux temperature of the reaction mixture.

In an embodiment, N-alkylated ester of formula (IV) may be reacted with 2-Hydrazinopyrazine derivative of formula V for sufficient time to complete the formation of Selinexor of formula (I).

In an embodiment, N-alkylated ester of formula (IV) may be reacted with 2-Hydrazinopyrazine derivative of formula V optionally in the presence of a catalyst. Catalyst may be selected from the group comprising of pyridine, dimethyl aminopyridine, triethyl amine, diisopropyl ethyl amine, metal alkoxides such as sodiummethoxide, organoaluminium reagents such as trialkyl or triaryl aluminium, 1-hydroxy benzotriazole (HOBT), 1-Ethyl-3-(3-dimethylaminopropyl)carbodiimide (EDCI) OR ITS HCl salt, Carbonyldiimidazole (CDI), dicylohexylcarbodiimide, Propane Phosphonic Acid Anhydride (T3P) or the like.

Step d) of this aspect may be carried out by optionally removing the protecting the group to obtain Selinexor of formula (I), wherein Z may be hydrogen. Removal of protecting group may be carried out according to methods known in the art for deprotection of nitrogen or according to the procedures described or exemplified in the present application.

Step e) of this aspect may be carried out by purifying Selinexor obtained in step c) of d) according to the suitable methods known in the art which include, but not limited to chromatographic separations, recrystallizing or slurrying in a solvent or mixture of solvents, acid-base treatment i.e., through salt formation or the like. Suitable acid that may be used is selected from any of the acceptable organic or inorganic acids known in the art and suitable for the formation of acid-addition salt or any acid disclosed in any aspect of the instant application.

In an embodiment, Selinexor may be purified through the formation of its acid addition salt.

In an embodiment, formation of acid addition salt of Selinexor may be obtained according to the methods known in the art or procedures described or exemplified in the instant application. In embodiments, Selinexor may be combined with a suitable acid optionally in the presence of a solvent or mixture of solvents to provide its acid addition salt.

The acid addition salt of Selinexor may be optionally isolated or converted into free Selinexor insitu without its isolation. In an embodiment, the salt of Selinexor may be combined with a suitable base to obtain free Selinexor.

In alternate embodiment, the salt of Selinexor may be isolated and then neutralized with a base to obtain Selinexor. Selinexor obtained by this method may be substantially pure Cis-isomer of Selinexor with enhanced chemical purity.

Selinexor of formula (I) or its addition salt recovered by the processes of application can be subjected to drying at suitable temperatures, such as about 30°-100° C. and suitable pressures, using drying equipment known in the art, such as air dryer, vacuum dryer, fluidized bed dryer, spin flash dryer, flash dryer, and the like. Drying can be carried out at temperatures and times sufficient to achieve desired quality of product.

In another aspect, the present application provides an addition salt of N-alkylated acid of formula VI.

In an embodiment, a addition salt of N-alkylated acid of formula VI may be a salt with a base selected from inorganic or organic base comprising hydroxides, carbonates, alkoxides, bicarbonates of alkali metals, alkaline earth metals, non-toxic metals, ammonium for example sodium, potassium, lithium, calcium, magnesium, aluminum, zinc, ammonium trimethylammonium, triethanolammonium, Pyridinium, substituted Pyridinium salts; mono-, di- and trisubstituted amines such as, Dicyclohexylamine(DCHA), tert-Butyl amine, diethyl amine, dibutylamine, Morpholine, 3-diemthylamino-1-propylamine, diisopropyl amine, N-tert-butylbenzylamine, N-benzylmethylamine, α-Methyl benzyl amine, (s)-α-methyl benzylamine, benzyl amine, dibenzylamine, cyclohexyl amine, tert-octylamine. Tris(hydroxymethyl)aminomethane, 2-Amino-2-methyl-1-propanol, 2-Amino-2-methyl-1,3-propanediol, 2,2'-(Propane-1,3-diyldiimino)bis[2-(hydroxymethyl) propane-1,3-diol],2-[Bis(2-hydroxyethyl)imino]-2-(hydroxymethyl)-1,3-propanediol, 2-Aminoethanol, (2R,3R,4R,5S)-6-Methylaminohexane-1,2,3,4,5-pentol, 2,2',2"-Nitrilotriethanol or the like.

In another aspect, the present application provides a process for the preparation of Selinexor comprising the step of preparing an addition salt of N-alkylated acid of formula VI.

In an embodiment, the process of preparing Selinexor using an addition salt of N-alkylated acid of formula VI obtained according to procedures described or exemplified in any aspect of the present application.

In embodiments, the addition salt of N-alkylated acid may be neutralized to obtain corresponding free acid of formula (IVa) before proceeding to next step (or) the addition salt of N-alkylated acid of formula (VI) may be directly used for the preparation of Selinexor. Neutralization of addition salt of N-alkylated acid may be carried out according to procedures described or exemplified in any aspect of the present application to obtain corresponding free acid of formula (IVa).

In another aspect, the present application provides N-alkylated acid of formula IVa or N-alkylated ester of formula IV having a chemical purity of at least 99% by HPLC or at least 99.5% by HPLC or at least 99.9% by HPLC.

In another aspect, the present application provides N-alkylated acid of formula IVa or N-alkylated ester of formula IV with corresponding trans-isomer content of not more than 0.1% by HPLC or not more than 0.05% by HPLC.

In another aspect, the present application provides a pharmaceutical composition comprising Selinexor obtained according any of the aspects of this application and at least one pharmaceutically acceptable excipient.

In another aspect, the present application provides Selinexor or its pharmaceutical composition comprising trans-isomer of Selinexor or (E)-3-(3-(3,5-bis(trifluoromethyl)phenyl)-1H-1,2,4-triazol-1-yl)acrylic acid of not more than 0.1% by HPLC or not more than 0.05% by HPLC.

In another aspect, the present application provides crystalline form of Selinexor. In embodiments, the crystalline form of Selinexor may be selected from the group comprising Form-Alpha, Form-Beta, Form-Gamma, Form-Delta, Form-Epsilon, Form-Zeta, Form-Eta, Form-Theta, Form-Iota, Form-Kappa, Form-Lambda, Form-Mu, Form Nu and Form-Xi of Selinexor or mixtures thereof.

In another aspect, the present application provides a crystalline Form-Alpha of Selinexor, characterized by a PXRD pattern comprising the peaks at about 4.38, 12.45, 13.13, 15.85, 19.98 and 21.35 ±0.2° 2θ. In an embodiment, the application provides crystalline form Alpha of Selinexor, characterized by a PXRD pattern having one or more additional peaks at about 14.51, 14.77, 20.30 and 27.32 ±0.2° 2θ.

Figure 2:
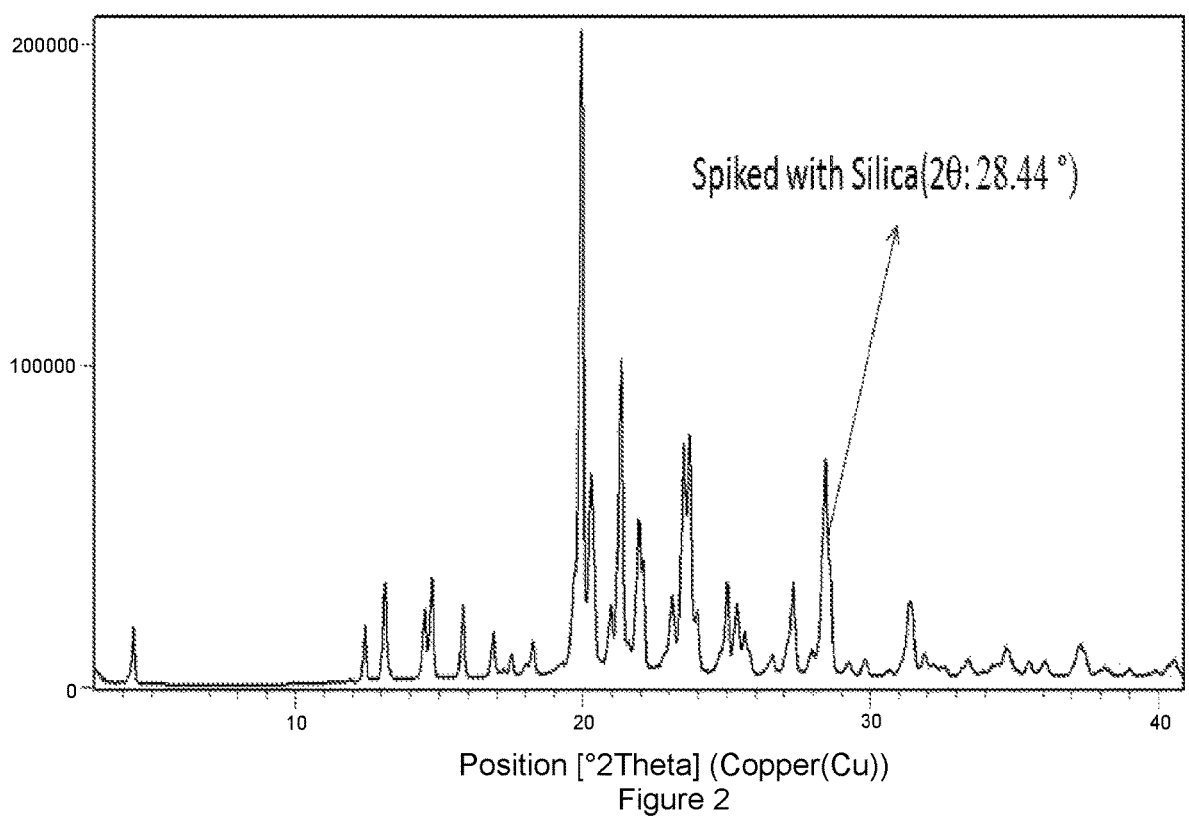
FIG. 2 is an illustrative X-ray powder diffraction pattern of crystalline Form-Alpha of Selinexor prepared by the method of Example No 5.

In an embodiment, the present application provides a crystalline Form-Alpha of Selinexor, characterized by a PXRD pattern having peaks located substantially as shown in FIG. 1 or 2.

In another aspect, the present application provides crystalline Form-Beta of Selinexor, characterized by a PXRD pattern comprising the peaks at about 5.87, 11.73, 18.71, 20.53 and 24.05 ±0.2° 2θ. In an embodiment, the application provides crystalline Form-Beta of Selinexor, characterized by a PXRD pattern having one or more additional peaks at about 16.28 and 21.28 ±0.2° 2θ.

Figure 3:
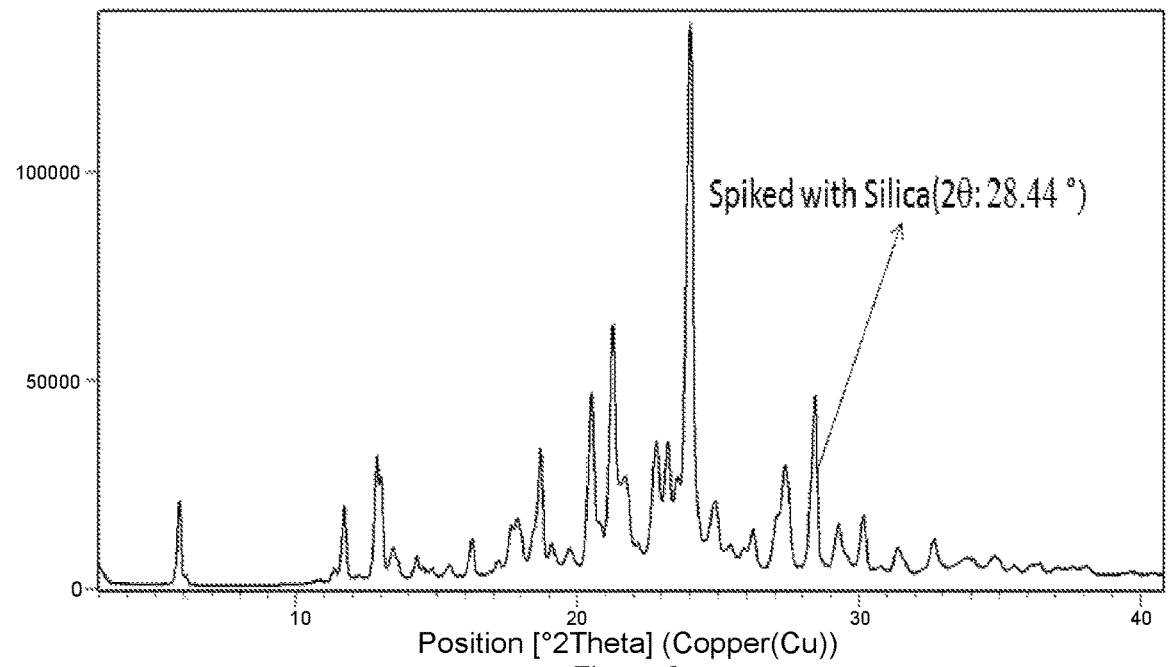
FIG. 3 is an illustrative X-ray powder diffraction pattern of crystalline Form-Beta of Selinexor prepared by the method of Example No 6.

In an embodiment, the present application provides a crystalline Form-Beta of Selinexor, characterized by a PXRD pattern having peaks located substantially as shown in FIG. 3.

In another aspect, the present application provides crystalline Form-Gamma of Selinexor, characterized by a PXRD pattern comprising the peaks at about 3.28, 11.95, 14.62, 15.74 and 20.96 ±0.2° 2θ. In an embodiment, the application provides crystalline Form-Gamma of Selinexor, characterized by a PXRD pattern having one or more additional peaks at about 16.95, 18.23, 20.01 and 22.13 ±0.2° 2θ.

Figure 4:
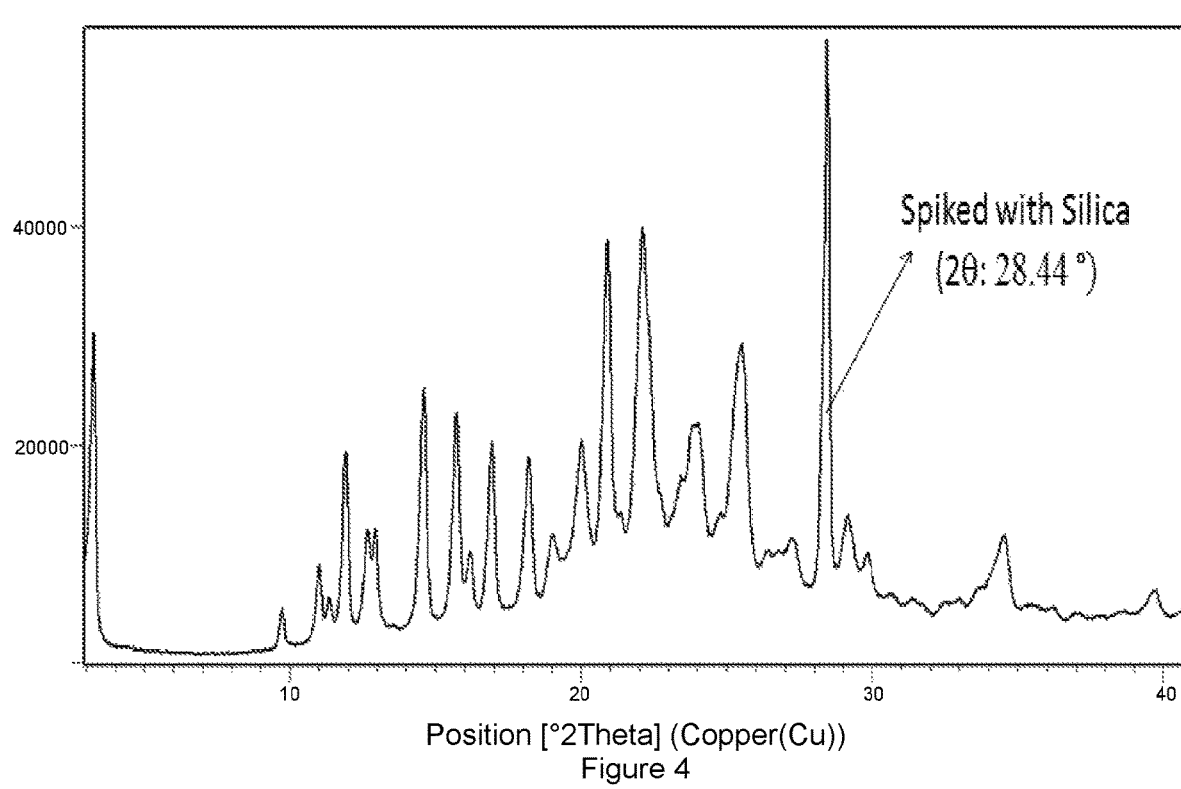
FIG. 4 is an illustrative X-ray powder diffraction pattern of crystalline Form-Gamma of Selinexor prepared by the method of Example No 7.

In an embodiment, the present application provides a crystalline Form-Gamma of Selinexor, characterized by a PXRD pattern having peaks located substantially as shown in FIG. 4.

In an aspect, the present application provides crystalline Form-Delta of Selinexor, characterized by a PXRD pattern comprising the peaks at about 6.11, 12.16, 13.00, 20.28 and 24.43 ±0.2° 2θ. In an embodiment, the application provides crystalline Form-Delta of Selinexor, characterized by a PXRD pattern having one or more additional peaks at about 19.35, 23.39 and 23.78 ±0.2° 2θ.

Figure 5:
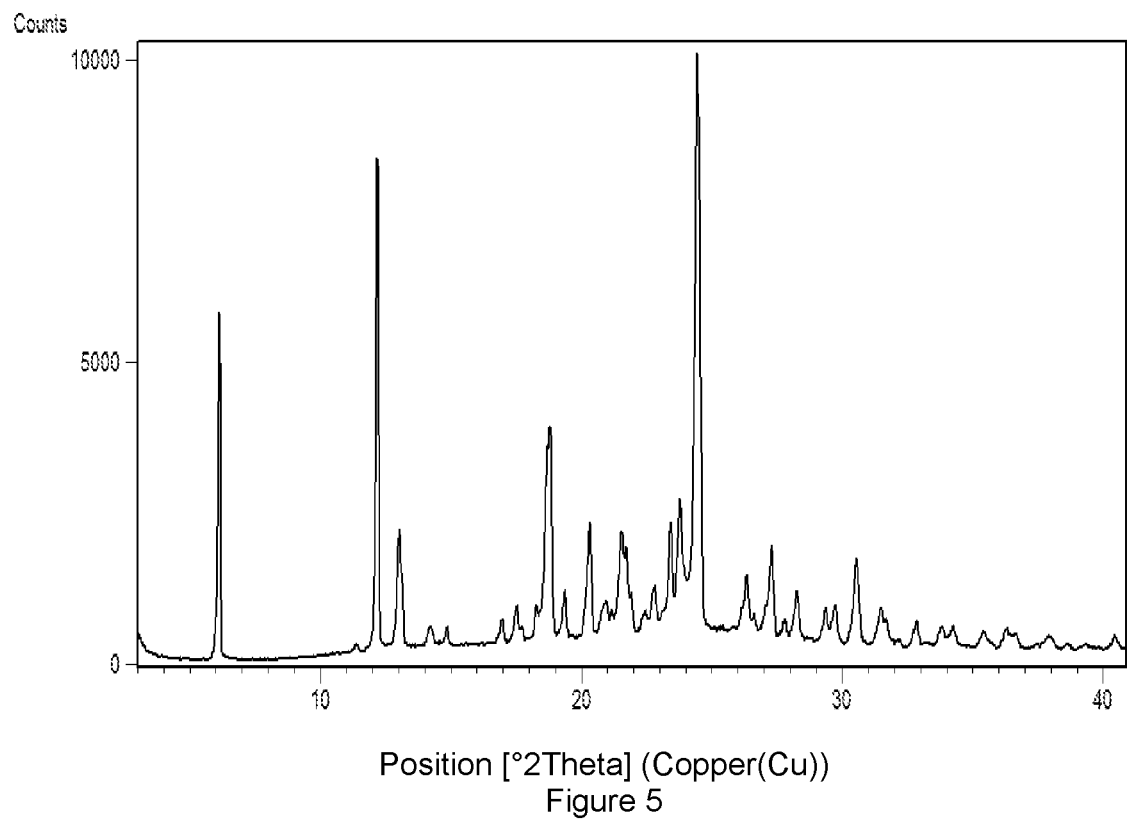
FIG. 5 is an illustrative X-ray powder diffraction pattern of crystalline Form-Delta of Selinexor prepared by the method of Example No 8.

In an embodiment, the present application provides a crystalline Form-Delta of Selinexor, characterized by a PXRD pattern having peaks located substantially as shown in FIG. 5.

In another aspect, the present application provides crystalline Form-Epsilon of Selinexor, characterized by a PXRD pattern comprising the peaks at about 5.87, 11.72, 17.61, 18.68, 20.50, 22.78, 23.20, 23.53 and 23.97±0.2° 2θ. In an embodiment, the application provides crystalline Form-Epsilon of Selinexor, characterized by a PXRD pattern having one or more additional peaks at about 16.26, 21.25, 25.35, 29.22 and 30.14±0.2° 2θ.

Figure 6:
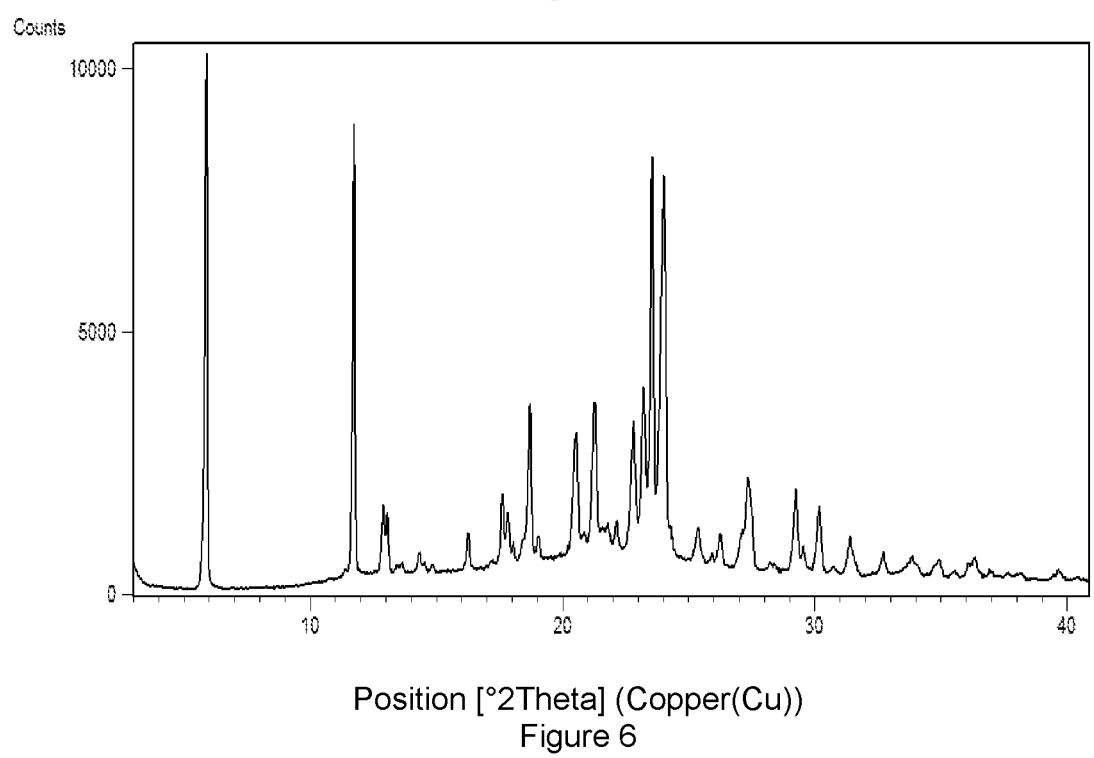
FIG. 6 is an illustrative X-ray powder diffraction pattern of crystalline Form-Epsilon of Selinexor prepared by the method of Example No 9.

In an embodiment, the present application provides a crystalline Form-Epsilon of Selinexor, characterized by a PXRD pattern having peaks located substantially as shown in FIG. 6.

In another aspect, the present application provides crystalline Form-Zeta of Selinexor, characterized by a PXRD pattern comprising the peaks at about 4.86, 6.99, 7.74, 10.86, 15.50 and 19.47 ±0.2° 2θ. In an embodiment, the application provides crystalline Form-Zeta of Selinexor, characterized by a PXRD pattern having one or more additional peaks at about 14.00, 18.27, 20.73, 21.51 and 22.14 ±0.2° 2θ.

Figure 7:
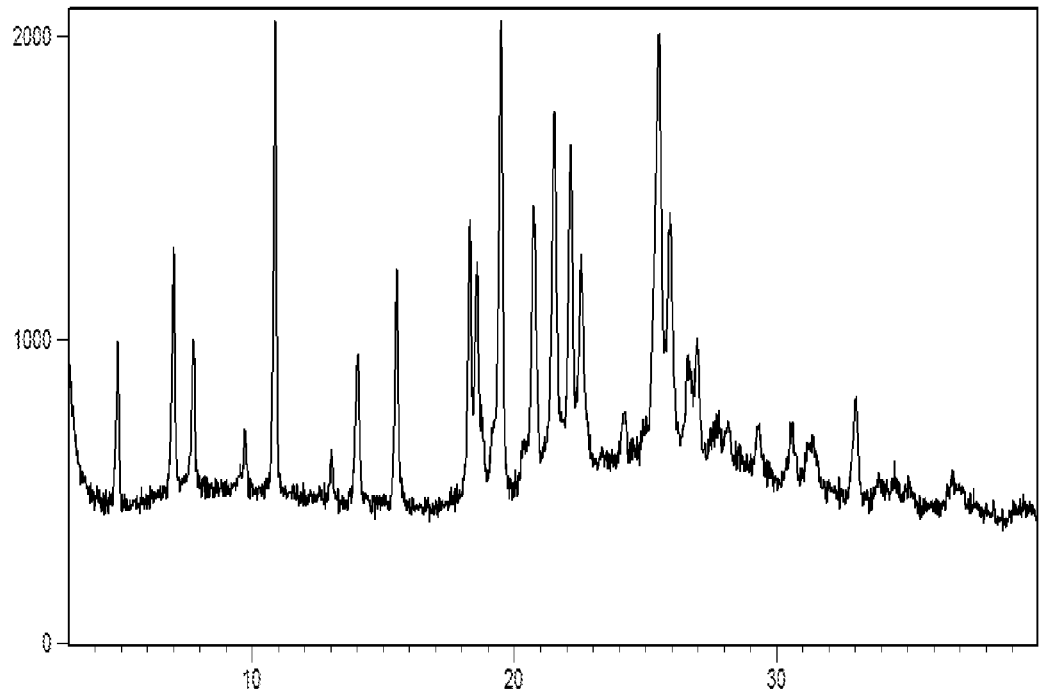
FIG. 7 is an illustrative X-ray powder diffraction pattern of crystalline Form-Zeta of Selinexor prepared by the method of Example No 10.

In an embodiment, the present application provides a crystalline Form-Zeta of Selinexor, characterized by a PXRD pattern having peaks located substantially as shown in FIG. 7.

In another aspect, the present application provides crystalline Form-Eta of Selinexor, characterized by a PXRD pattern comprising the peaks at about 3.54, 7.03, 9.91, 11.59, 19.84, 20.44 and 21.64 ±0.2° 2θ. In an embodiment, the application provides crystalline Form-Eta of Selinexor, characterized by a PXRD pattern having one or more additional peaks at about 17.55, 21.09, 22.45 and 23.28 ±0.2° 2θ.

Figure 8:
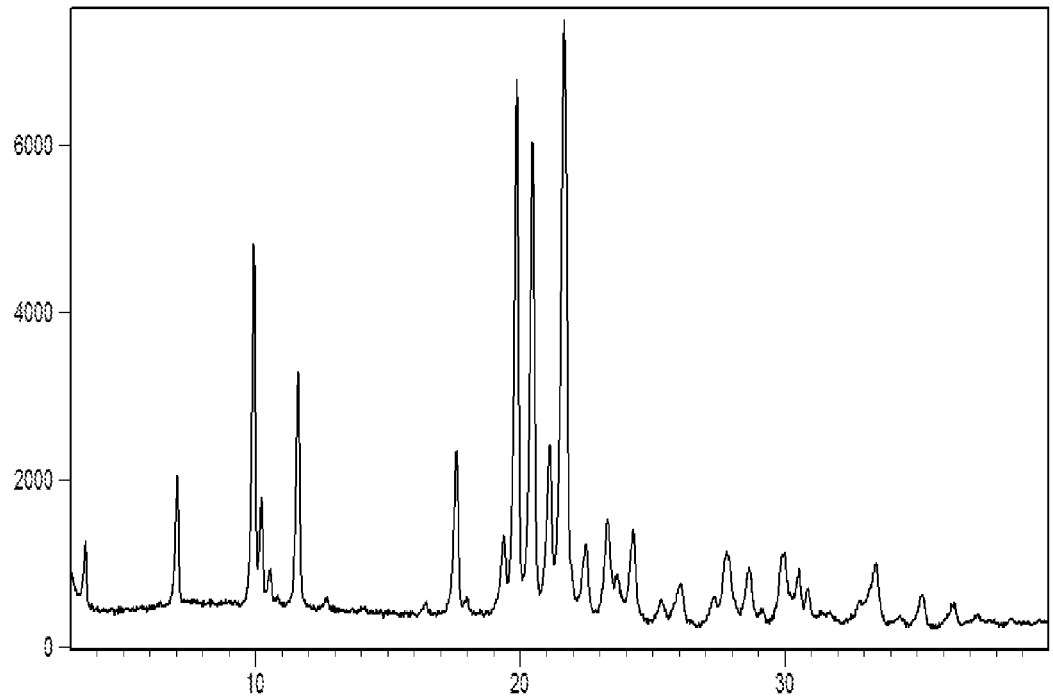
FIG. 8 is an illustrative X-ray powder diffraction pattern of crystalline Form-Eta of Selinexor prepared by the method of Example No 11.

In an embodiment, the present application provides a crystalline Form-Eta of Selinexor, characterized by a PXRD pattern having peaks located substantially as shown in FIG. 8.

In another aspect, the present application provides crystalline Form-Theta of Selinexor, characterized by a PXRD pattern comprising the peaks at about 6.96, 13.92, 20.95 and 22.82 ±0.2° 2θ. In an embodiment, the application provides crystalline Form-Theta of Selinexor, characterized by a PXRD pattern having one or more additional peaks at about 17.24, 20.03, 20.37 and 23.41 ±0.2° 2θ.

Figure 9:
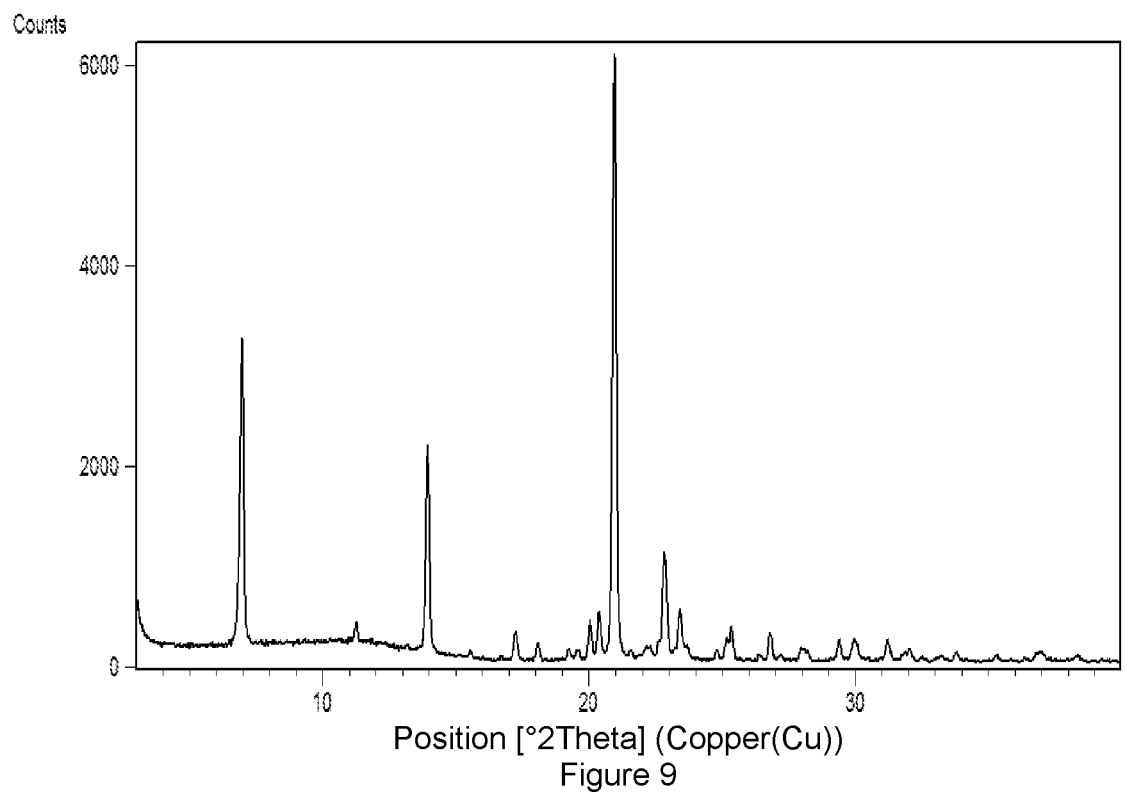
FIG. 9 is an illustrative X-ray powder diffraction pattern of crystalline Form-Theta of Selinexor prepared by the method of Example No 12.

In an embodiment, the present application provides a crystalline Form-Theta of Selinexor, characterized by a PXRD pattern having peaks located substantially as shown in FIG. 9.

In another aspect, the present application provides crystalline Form-Iota of Selinexor, characterized by a PXRD pattern comprising the peaks at about 3.69, 7.33, 11.01, 14.66, 16.19 and 18.36 ±0.2° 2θ.

Figure 10:
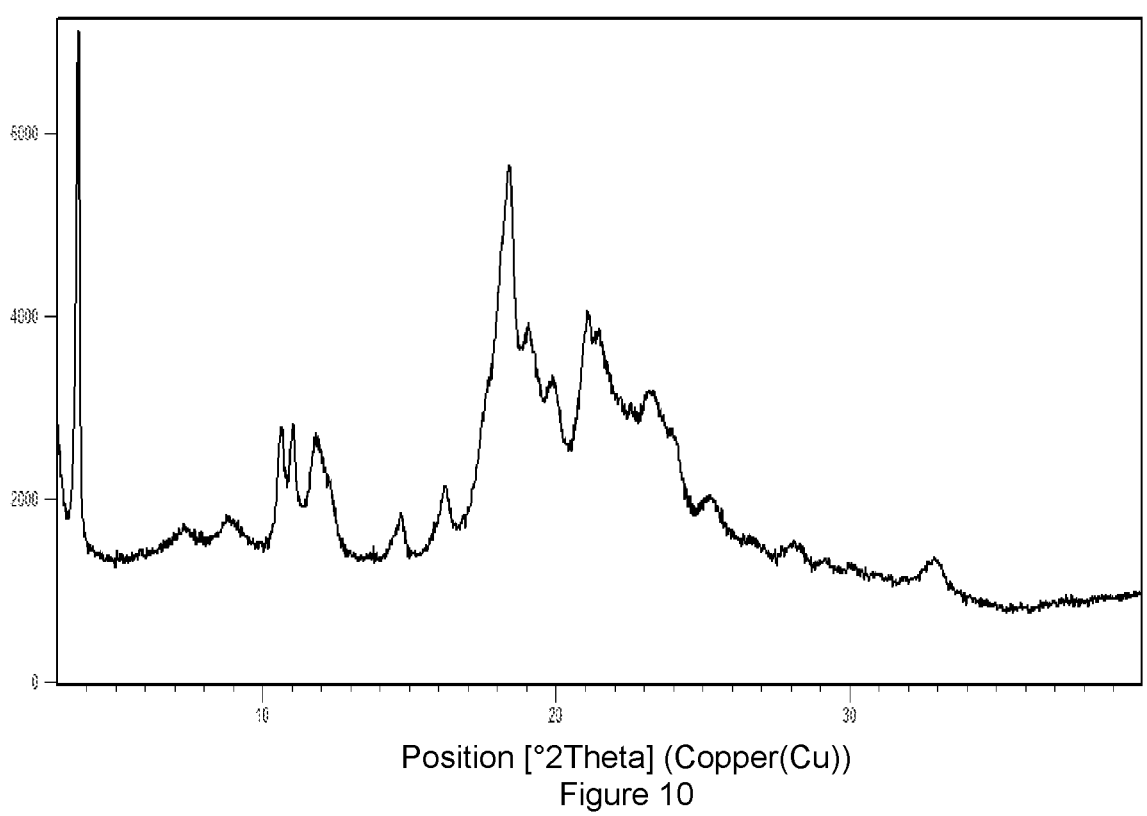
FIG. 10 is an illustrative X-ray powder diffraction pattern of crystalline Form-Iota of Selinexor prepared by the method of Example No 13.

In an embodiment, the present application provides a crystalline Form-Iota of Selinexor, characterized by a PXRD pattern having peaks located substantially as shown in FIG. 10.

In another aspect, the present application provides crystalline Form-Kappa of Selinexor, characterized by a PXRD pattern comprising the peaks at about 3.22, 11.71, 12.56, 14.42 and 25.20 ±0.2° 2θ.

Figure 11:
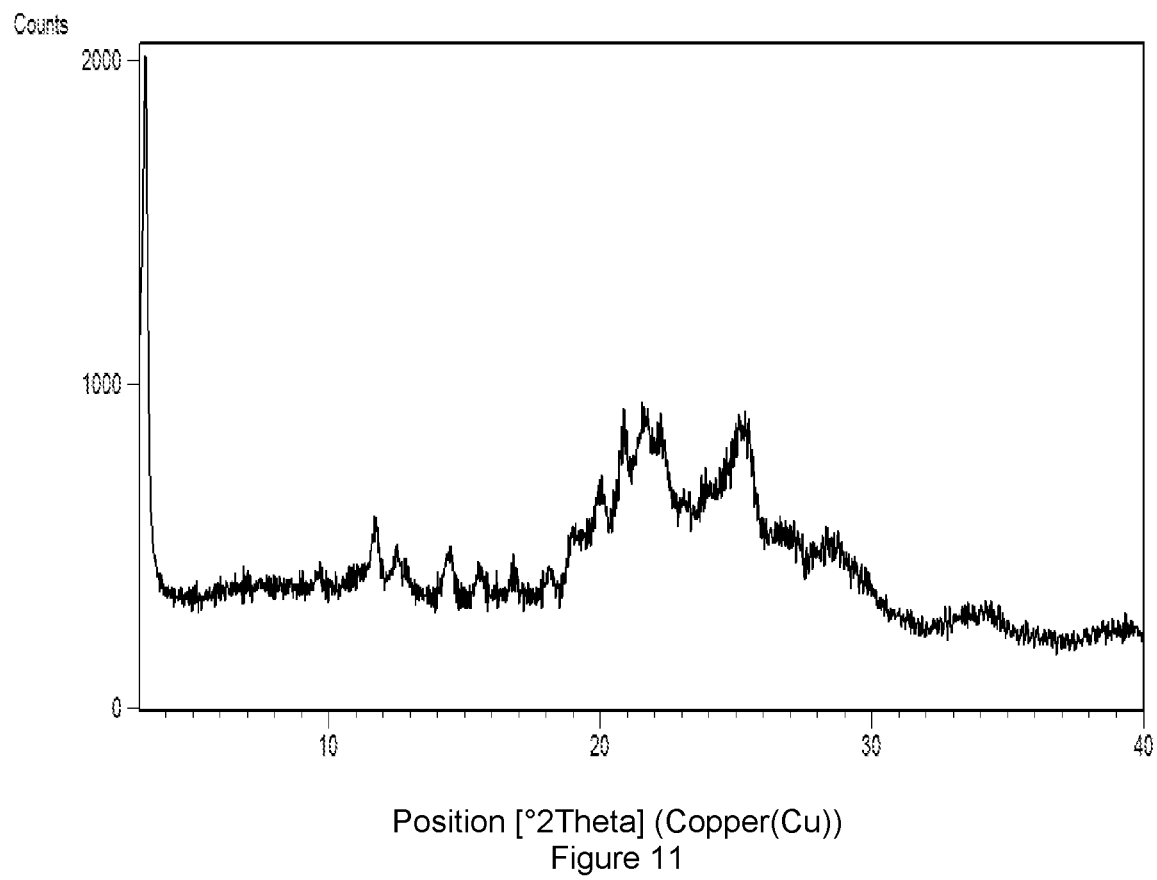
FIG. 11 is an illustrative X-ray powder diffraction pattern of crystalline Form-Kappa of Selinexor prepared by the method of Example No 14.
Figure 22:
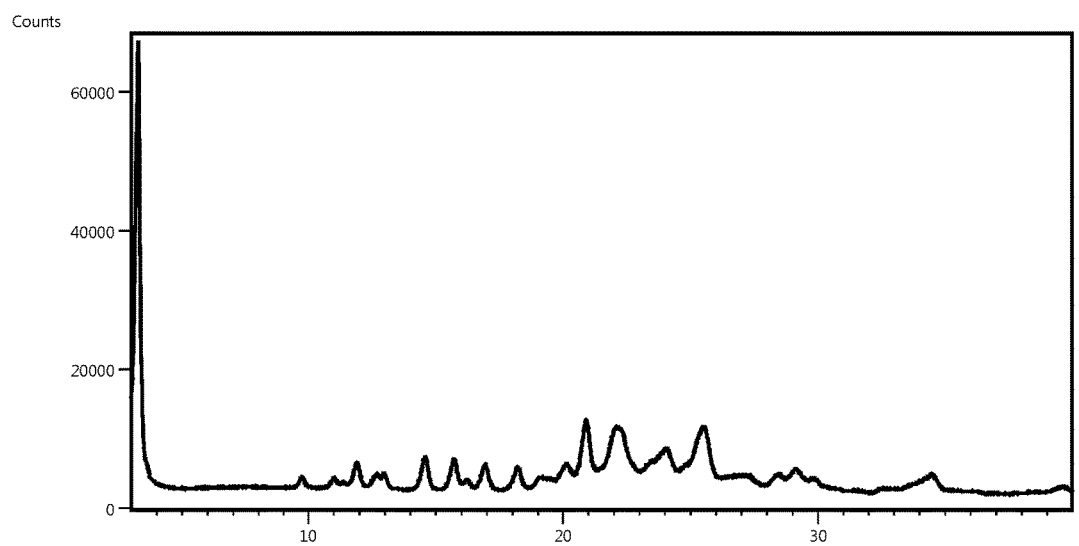
FIG. 22 is an illustrative X-ray powder diffraction pattern of crystalline Form-Kappa of Selinexor prepared by the alternate method of Example No 14.

In an embodiment, the present application provides a crystalline Form-Kappa of Selinexor, characterized by a PXRD pattern having peaks located substantially as shown in FIGS. 11 & 22.

In another aspect, the present application provides crystalline Form-Lambda of Selinexor, characterized by a PXRD pattern comprising the peaks at about 12.61, 19.00, 19.95 and 21.29 ±0.2° 2θ. In an embodiment, the application provides crystalline Form-Lambda of Selinexor, characterized by a PXRD pattern having one or more additional peaks at about 14.13, 21.29, 21.75, 23.10, 24.65 and 30.86 ±0.2° 2θ.

Figure 12:
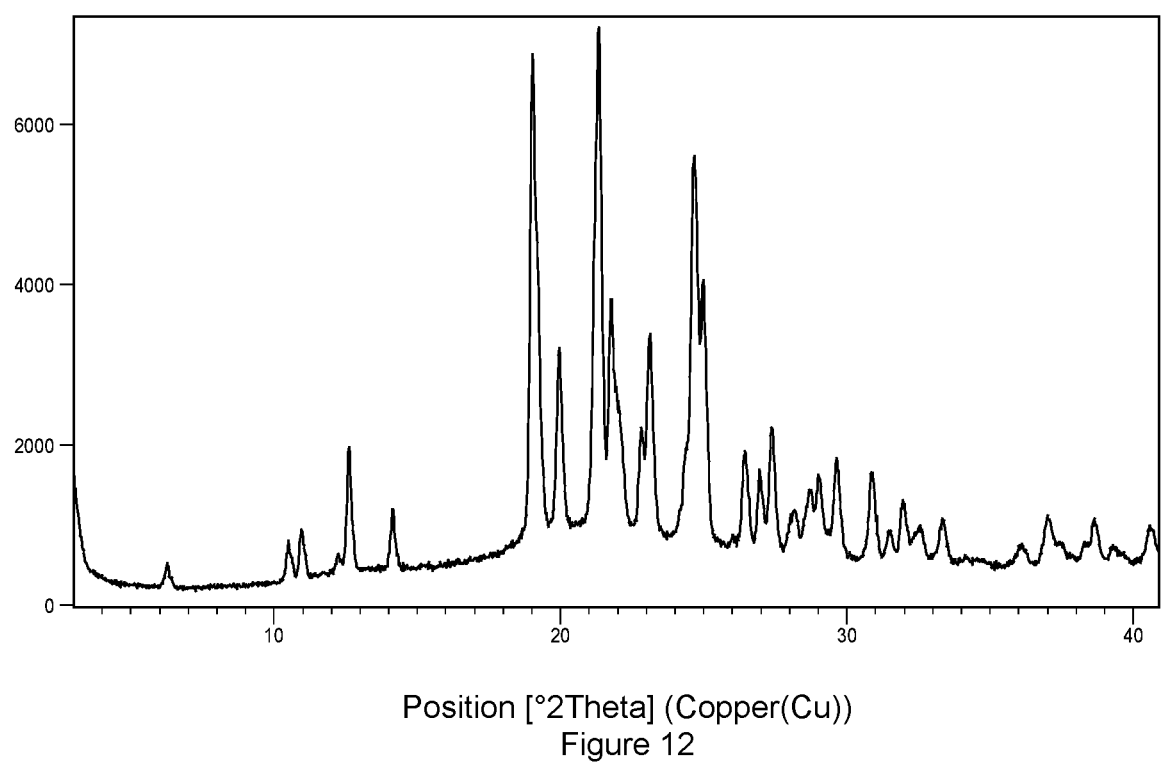
FIG. 12 is an illustrative X-ray powder diffraction pattern of crystalline Form-Lambda of Selinexor prepared by the method of Example No 15.

In an embodiment, the present application provides a crystalline Form-Lambda of Selinexor, characterized by a PXRD pattern having peaks located substantially as shown in FIG. 12.

In another aspect, the present application provides crystalline Form-Mu of Selinexor, characterized by a PXRD pattern comprising the peaks at about 9.31, 17.45, 17.85 and 22.72 ±0.2° 2θ. In an embodiment, the application provides crystalline Form-Mu of Selinexor, characterized by a PXRD pattern having one or more additional peaks at about 21.20, 25.01 and 27.59 ±0.2° 2θ.

Figure 13:
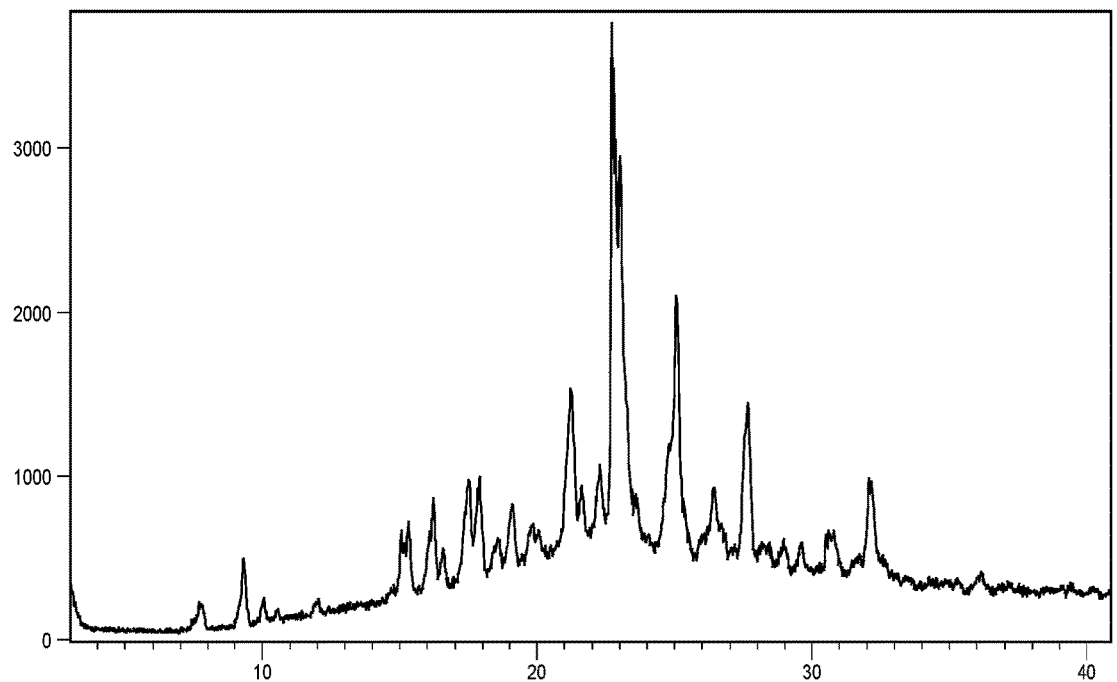
FIG. 13 is an illustrative X-ray powder diffraction pattern of crystalline Form-Mu of Selinexor prepared by the method of Example No 16.

In an embodiment, the present application provides a crystalline Form-Mu of Selinexor, characterized by a PXRD pattern having peaks located substantially as shown in FIG. 13.

In another aspect, the present application provides crystalline Form-Nu of Selinexor, characterized by a PXRD pattern comprising the peaks at about 10.75, 17.52, 21.84, 22.16 and 22.38 ±0.2° 2θ. In an embodiment, the application provides crystalline Form-Nu of Selinexor, characterized by a PXRD pattern having one or more additional peaks at about 18.30, 24.53 and 28.91 ±0.2° 2θ.

Figure 14:
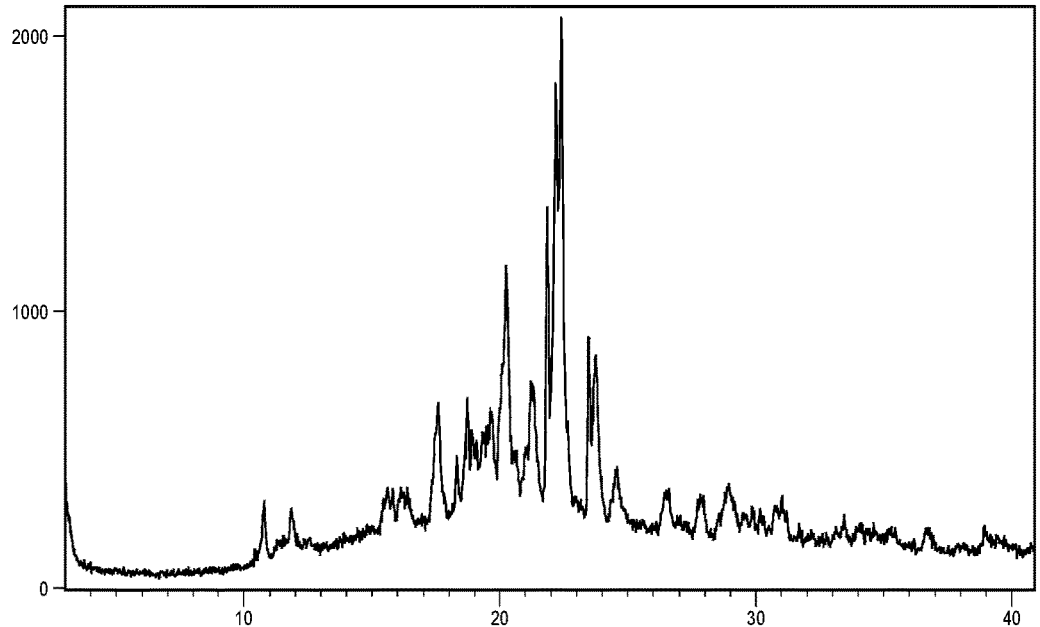
FIG. 14 is an illustrative X-ray powder diffraction pattern of crystalline Form-Nu of Selinexor prepared by the method of Example No 17.

In an embodiment, the present application provides a crystalline Form-Nu of Selinexor, characterized by a PXRD pattern having peaks located substantially as shown in FIG. 14.

In another aspect, the present application provides crystalline Form-Xi of Selinexor, characterized by a PXRD pattern comprising the peaks at about 10.54, 11.68, 12.72 and 24.56 ±0.2° 2θ. In an embodiment, the application provides crystalline Form-Xi of Selinexor, characterized by a PXRD pattern having one or more additional peaks at about 3.70, 7.36, 18.10, 19.72 and 21.21 ±0.2° 2θ.

Figure 15:
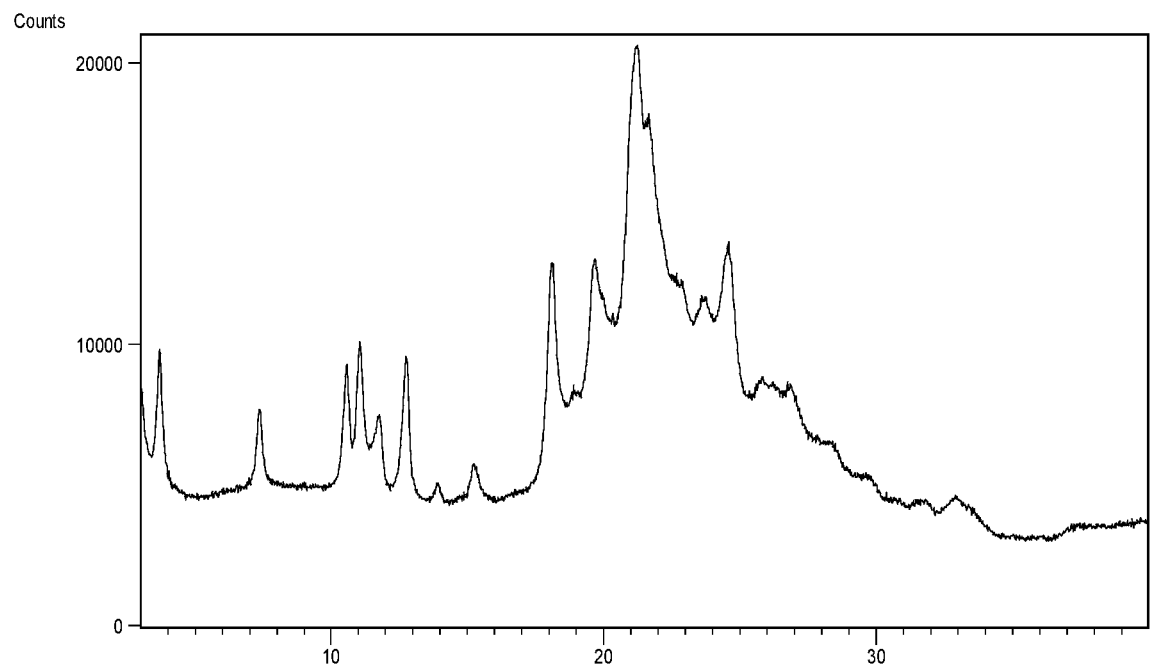
FIG. 15 is an illustrative X-ray powder diffraction pattern of crystalline Form-Xi of Selinexor prepared by the method of Example No 18.

In an embodiment, the present application provides a crystalline Form-Xi of Selinexor, characterized by a PXRD pattern having peaks located substantially as shown in FIG. 15.

Figure 16:
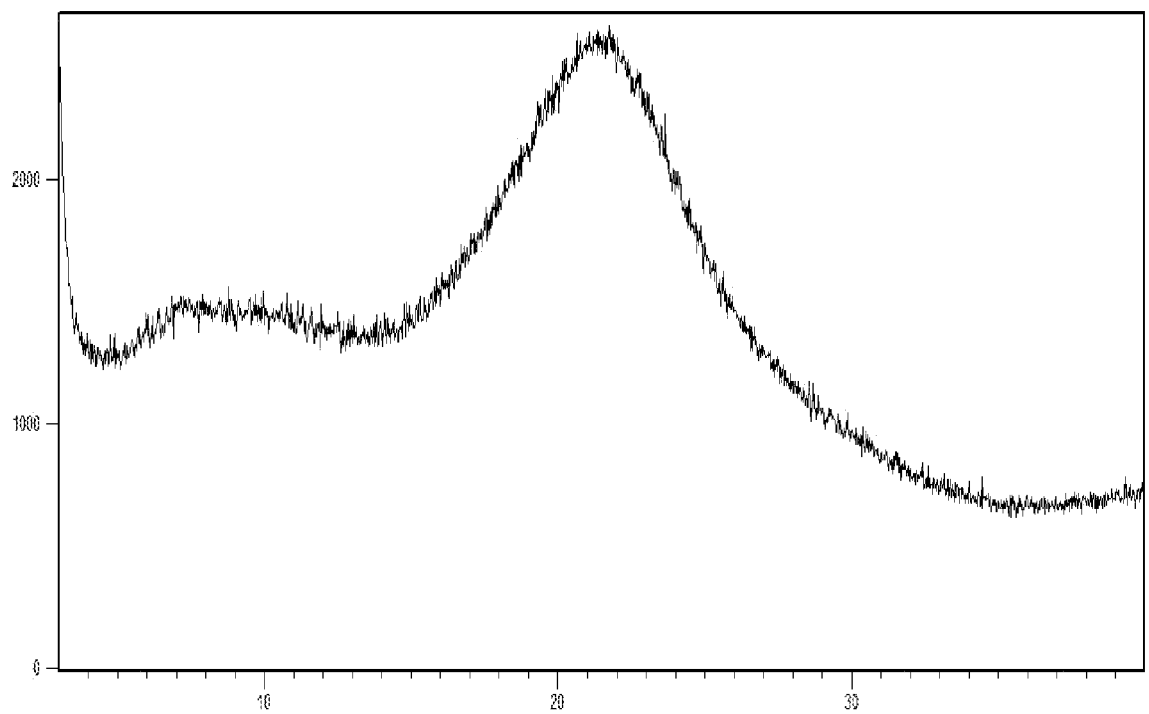
FIG. 16 is an illustrative X-ray powder diffraction pattern of amorphous form of Selinexor prepared by the method of Example No 19.
Figure 17:
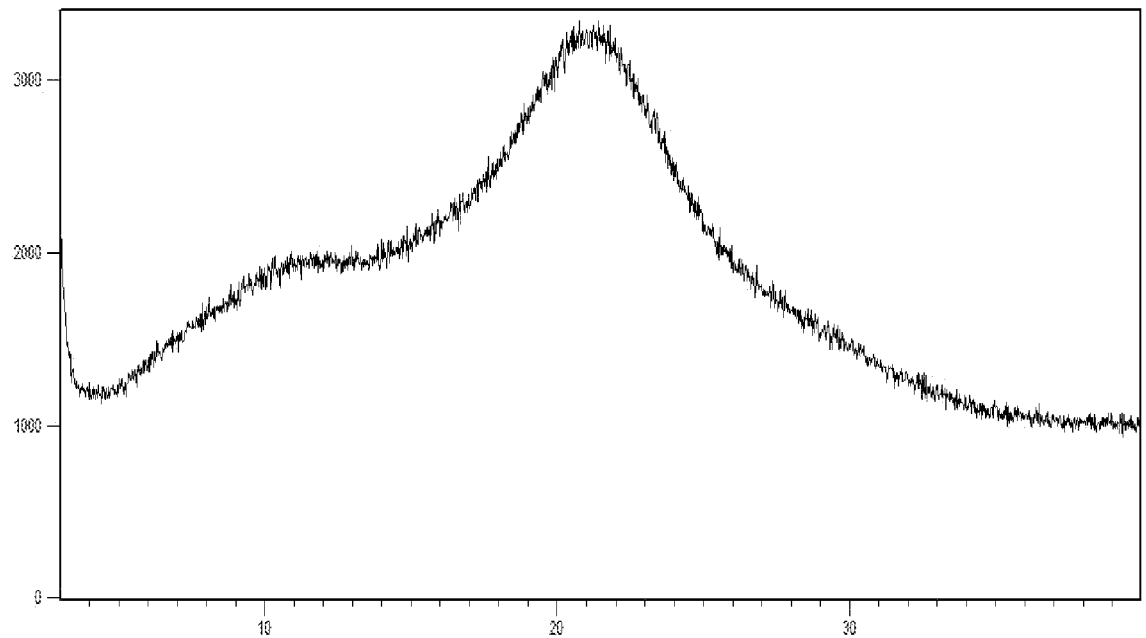
FIG. 17 is an illustrative X-ray powder diffraction pattern of amorphous solid dispersion of Selinexor with povidone K-30 prepared by the method of Example No 21.
Figure 18:
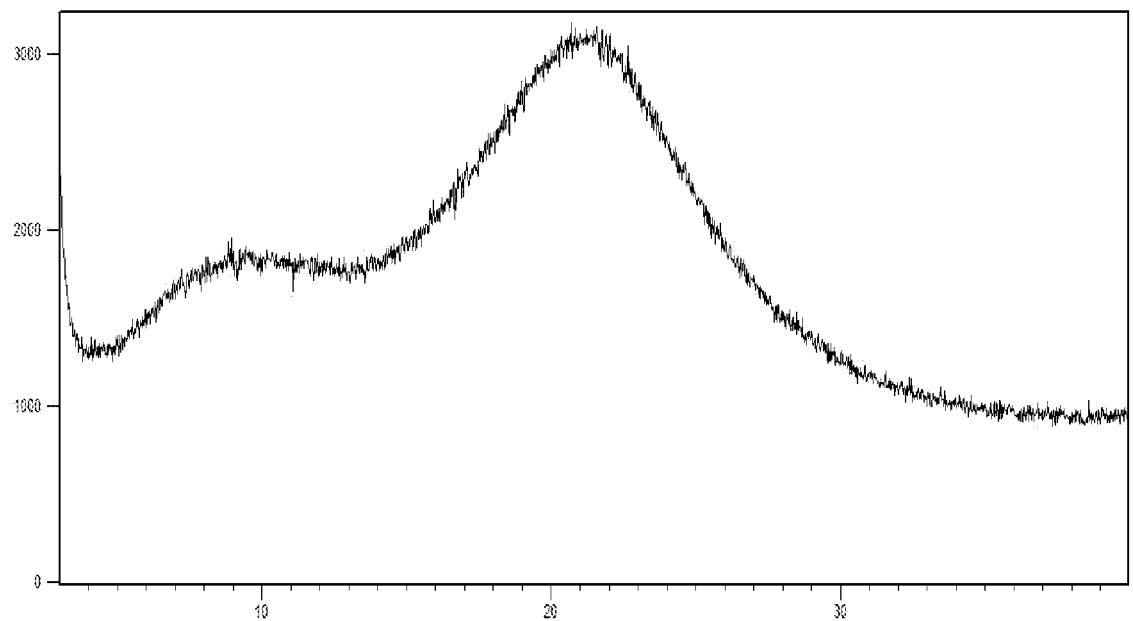
FIG. 18 is an illustrative X-ray powder diffraction pattern of amorphous solid dispersion of Selinexor with HPMC phthalate prepared by the method of Example No 22.
Figure 19:
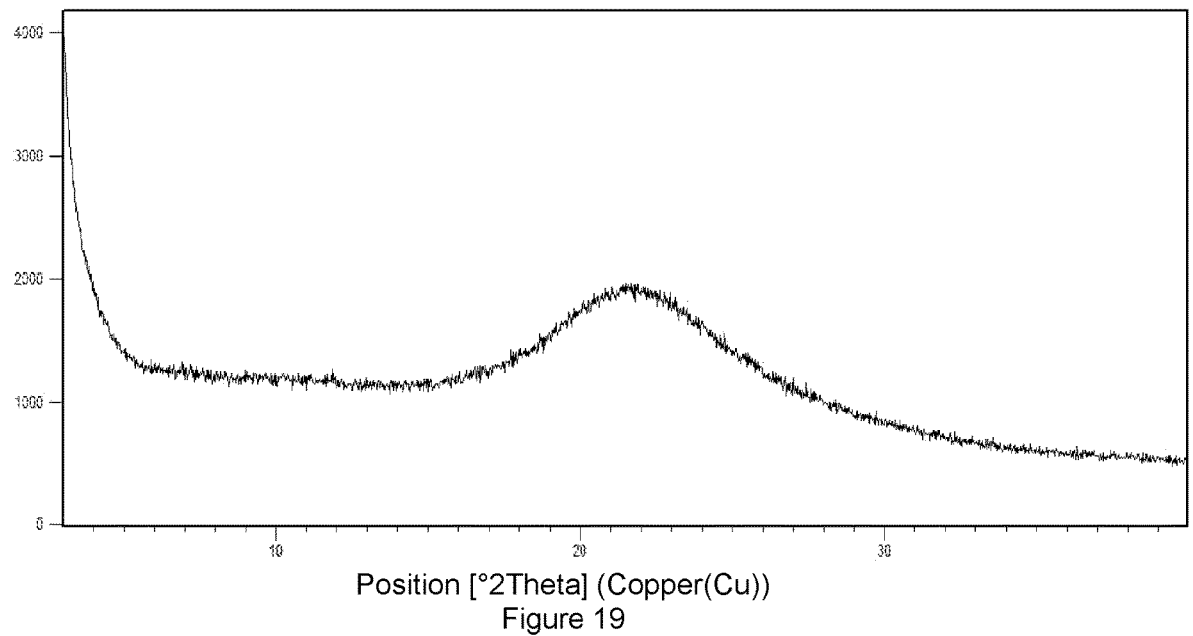
FIG. 19 is an illustrative X-ray powder diffraction pattern of amorphous solid dispersion of Selinexor with povidone K-30 and Syloid-244 FP NF prepared by the method of Example No 21.
Figure 20:
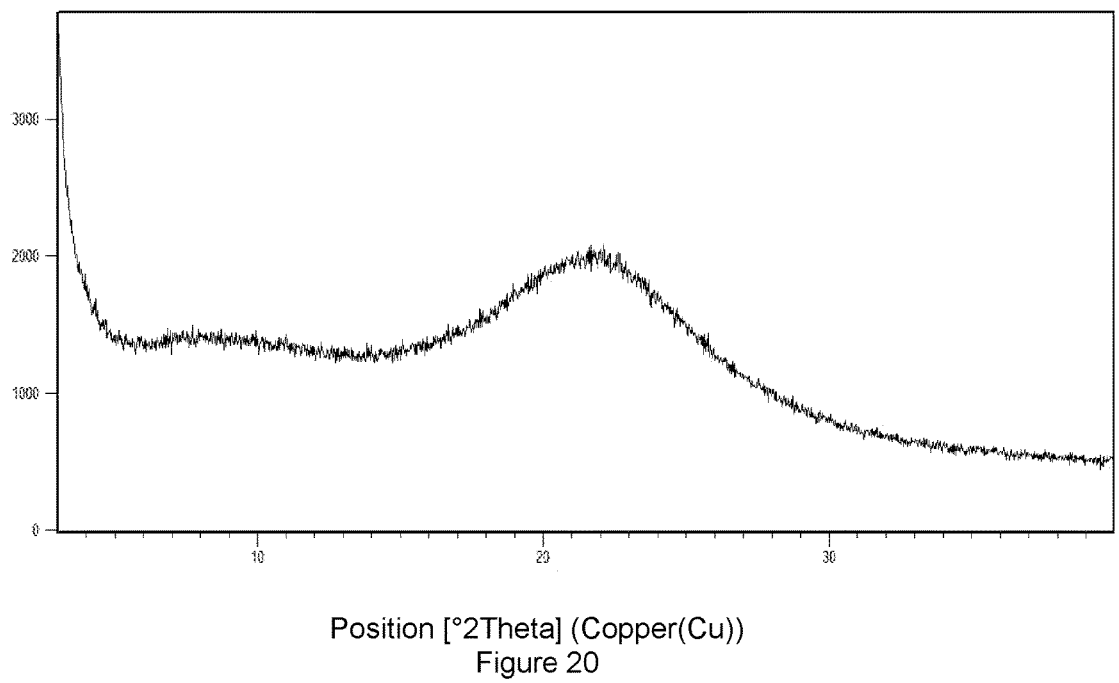
FIG. 20 is an illustrative X-ray powder diffraction pattern of amorphous solid dispersion of Selinexor with HPMC phthalate and Syloid-244 FP NF prepared by the method of Example No 22.
Figure 21:
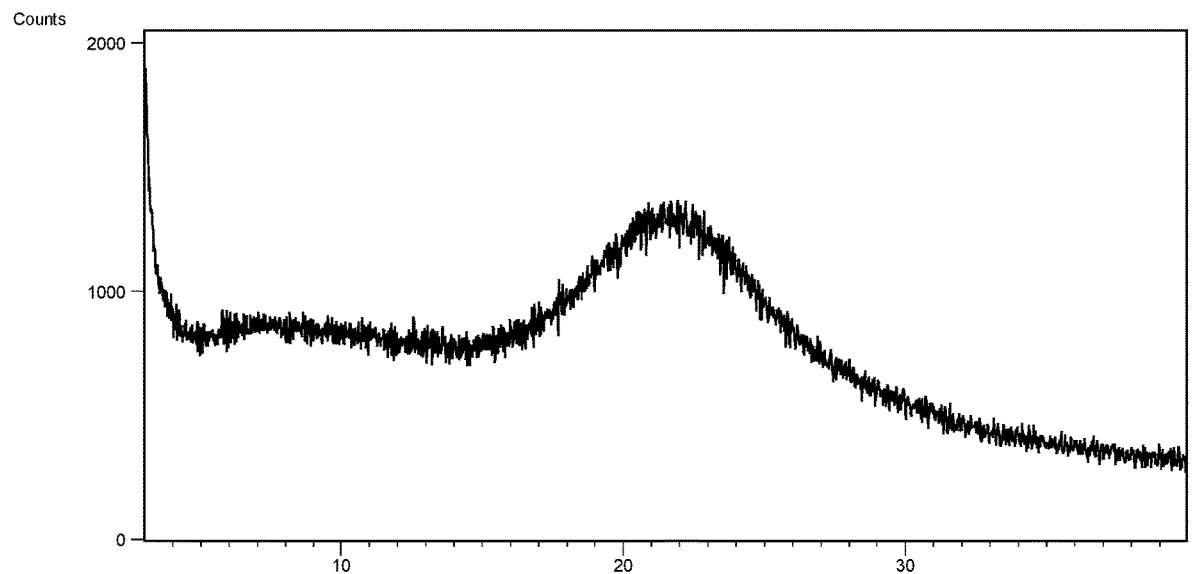
FIG. 21 is an illustrative X-ray powder diffraction pattern of amorphous form Selinexor with Syloid-244 FP NF prepared by the method of Example No 23.

In another aspect, the present application provides an amorphous form of Selinexor. In an embodiment, the present application provides an amorphous form of Selinexor characterized by a powder X-ray diffraction (PXRD) pattern, substantially as illustrated by FIG. 16.

The present application provides a stable amorphous form of Selinexor suitable for powder handling and downstream processes. Amorphous form of Selinexor of the present application which was surprisingly found to be highly stable under mechanical stress such as grinding and milling and stable under hygroscopic conditions such as higher relative humidity conditions of more than 60% RH. In an embodiment, the present application provides a stable amorphous form of Selinexor with less than 5% of crystallinity, preferably with less than 1% crystallinity and more preferably devoid of crystallinity as per X-ray diffraction analysis.

In another aspect, the present application provides a pharmaceutical composition comprising amorphous form of Selinexor combined with at least one pharmaceutically acceptable excipient.

In an embodiment, pharmaceutically acceptable excipient may be selected from the group consisting of silicon dioxide, e.g. colloidal or fumed silicon dioxide or porous silica; copolymers, such as polyethylene/polyvinyl alcohol copolymer, polyethylene/polyvinyl pyrrolidinone copolymer; and cellulose, preferably microcrystalline cellulose.

In an aspect, the present application provides amorphous solid dispersion of Selinexor together with at least one pharmaceutically acceptable excipient.

In an embodiment, the present application provides amorphous solid dispersion of Selinexor together with at least one pharmaceutically acceptable excipient characterized by a powder X-ray diffraction (PXRD) pattern, substantially as illustrated by FIGS. 17-20.

In an embodiment, pharmaceutically acceptable excipient of this aspect may be selected from the group consisting of polyvinyl pyrrolidone, povidone K-30, povidone K-60, Povidone K-90, polyvinylpyrrolidone vinylacetate, co-povidone NF, polyvinylacetal diethylaminoacetate (AEA®), polyvinyl acetate phthalate, polysorbate 80, polyoxyethylene-polyoxypropylene copolymers (Poloxamer® 188), polyoxyethylene (40) stearate, polyethyene glycol monomethyl ether, polyethyene glycol, poloxamer 188, pluronic F-68, methylcellulose, methacrylic acid copolymer (Eudragit), hydroxypropylmethyl cellulose phthalate, hydroxypropylmethyl cellulose acetate succinate, hydroxypropylmethyl cellulose, hydroxypropyl cellulose SL, hydroxyethyl cellulose, gelucire 44/14, ethyl cellulose, D-alpha-tocopheryl polyethylene glycol 1000 succinate, cellulose acetate phthalate, carboxymethylethylcelluloseand the like; cyclodextrins, gelatins, hypromellose phthalates, sugars, polyhydric alcohols, and the like; water soluble sugar excipients, preferably having low hygroscopicity, which include, but are not limited to, mannitol, lactose, fructose, sorbitol, xylitol, maltodextrin, dextrates, dextrins, lactitol and the like; polyethylene oxides, polyoxyethylene derivatives, polyvinyl alcohols, propylene glycol derivatives and the like; organic amines such as alkyl amines (primary, secondary, and tertiary), aromatic amines, alicyclic amines, cyclic amines, aralkyl amines, hydroxylamine or its derivatives, hydrazine or its derivatives, and guanidine or its derivatives, or any other excipient at any aspect of present application. The use of mixtures of more than one of the pharmaceutical excipients to provide desired release profiles or for the enhancement of stability is within the scope of this invention. Also, all viscosity grades, molecular weights, commercially available products, their copolymers, and mixtures are all within the scope of this invention without limitation.

In another aspect, the present application provides a pharmaceutical composition comprising amorphous solid dispersion of Selinexor combined with at least one pharmaceutically acceptable excipient.

In an embodiment, pharmaceutically acceptable excipient may be different from the excipient used in solid dispersion. In an embodiment, pharmaceutically acceptable excipient selected from the group consisting of silicon dioxide, e.g. colloidal or fumed silicon dioxide or porous silica; copolymers, such as polyethylene/polyvinyl alcohol copolymer, polyethylene/polyvinyl pyrrolidinone copolymer; and cellulose, preferably microcrystalline cellulose.

In another aspect, the present application provides process for preparing a crystalline form of Selinexor, which comprises:
a) combining amorphous Selinexor with a solvent or a mixture thereof;
b) stirring the mixture of step a);
c) optionally adding an anti-solvent to the mixture of step a) or b)
d) isolating crystalline form of Selinexor.

In an embodiment, Selinexor that is used in step a) of this aspect may be either the amorphous form of Selinexor or by directly taking a synthetic reaction mixture comprising Selinexor and a solvent or mixture of solvents.

In an embodiment, amorphous Selinexor that is used in step a) may be purified by any methods known in the art such as column chromatography, fractional distillation, acid-base treatment, slurring or re-crystallization, before using.

In an embodiment of step a), solvent may include, but not limited to water; ketones, such as acetone, methyl ethyl ketone, methyl isobutyl ketone, and diethyl ketone; esters, such as ethyl acetate, propyl acetate, isopropyl acetate, and butyl acetate; alcohols, such as methanol, ethanol, ethylene glycol, 1-propanol, 2-propanol (isopropyl alcohol), 1-butanol, 2-butanol, iso-butyl alcohol, t-butyl alcohol, 2-ethoxyethanol; nitriles, such as acetonitrile and propionitrile; halogenated hydrocarbons, such as dichloromethane, chloroform and carbontetrachloride; and dimethoxyethane; aprotic nonpoplar solvents such as dimethylsulfoxide; formamide, N,N-dimethylformamide, N,N-dimethylacetamide, N-methyl-2-pyrrolidone; any mixtures of two or more thereof.

In an embodiment, amorphous Selinexor may be combined with solvent at any suitable temperatures, such as at about 0° C. to about the reflux temperature of the solvent or mixture thereof. The mixture of Selinexor in solvent may be prepared preferably at about 0° C. to 80° C.

In an embodiment the mixture of amorphous Selinexor and solvent may be either a heterogeneous or homogeneous phase.

In an embodiment, the mixture of amorphous Selinexor and solvent may be optionally filtered to make particle free solution when it is a homogeneous clear solution and treated with a decolorizing agent, such as carbon, before filtration.

In an embodiment, the mixture of amorphous Selinexor and solvent may be cooled to suitable temperature for the precipitation of crystalline Selinexor from the mixture. In an embodiment, the mixture of amorphous Selinexor and solvent may be cooled drastically or gradually with either constant rate of cooling or by step-wise cooling periodically to achieve desired nature of the crystalline Selinexor.

In an embodiment, the mixture of amorphous Selinexor and solvent may be stirred for sufficient time to complete formation of crystalline Selinexor. In an embodiment, the mixture of amorphous Selinexor and solvent may be stirred for at least 1 hour or more, preferably for at least 24 hours or more and more preferably at least 48 hours or more.

In an embodiment, the mixture of amorphous Selinexor and solvent may be stirred at suitable temperature for the formation of crystalline form of Selinexor. In an embodiment, the mixture of amorphous Selinexor and solvent may be stirred at 0° C. and above, preferably between 0° C. to reflux temperature of the solvent used, more preferably between 0° C. and 50° C.

In an embodiment, optionally an anti-solvent may be added to the mixture of step a) or b). In an embodiment, anti-solvent may be added for sufficient time and at suitable temperature to complete the formation of crystalline Selinexor. Anti-solvents may include but not limited to water; aliphatic hydrocarbons, such as hexane, heptane, cyclohexane; aromatic hydrocarbons, such as toluene, xylene and chlorobenzene; ethers, such as diethyl ether, di-isopropyl ether, tetrahydrofuran, dioxane; or the like.

In an embodiment, isolation of crystalline form of Selinexor may be carried out by any methods known in the art or procedures described in the present application. In an embodiment, crystalline Selinexor may be isolated by employing any of the techniques, but not limited to: decantation, filtration by gravity or suction, centrifugation, adding solvent to make slurry followed by filtration, or other techniques specific to the equipment used and the like, and optionally washing with a solvent.

In an embodiment, isolated crystalline form of Selinexor may be dried in a suitable drying equipment such as tray dryer, vacuum oven, rotatory cone dryer, air oven, fluidized bed dryer, spin flash dryer, flash dryer, or the like. The drying may be carried out at atmospheric pressure or under reduced pressures at temperatures of less than about 100° C., less than about 60° C., less than about 40° C., or any other suitable temperatures. Drying can be carried out at temperatures and times sufficient to achieve desired quality of product. Drying may be carried out for any time period required for obtaining a desired quality, such as from about 15 minutes to 10 hours or longer.

In embodiments, the crystalline Selinexor isolated at step d) of this aspect may be selected from the group comprising of Form-Alpha, Form-Beta, Form-Gamma, Form-Delta, Form-Epsilon, Form-Zeta, Form-Eta, Form-Theta, Form-Iota, Form-Kappa, Form-Lambda, Form-Mu, Form Nu and Form-Xi or mixtures thereof.

In another aspect, the present application provides a process for the preparation of crystalline form of Selinexor or a solvate thereof, comprising the step of converting amorphous Selinexor to crystalline form of Selinexor or a solvate thereof.

In an embodiment, crystalline form of Selinexor may be selected from the group comprising of crystalline form A, Form B, Form C, Form D, Form-Alpha, Form-Beta, Form-Gamma, Form-Delta, Form-Epsilon, Form-Zeta, Form-Eta, Form-Theta, Form-Iota, Form-Kappa, Form-Lambda, Form-Mu, Form Nu and Form-Xi or mixtures thereof.

In an embodiment, the step of converting amorphous Selinexor to crystalline form may be carried out by suspending or re-crystallizing amorphous Selinexor in a suitable solvent or mixture of solvents.

Re-crystallizing amorphous Selinexor may be carried out by according previous aspects or any of the methods or procedures described or exemplified in the present application. In an embodiment, amorphous Selinexor may be suspended in a suitable solvent or mixture of solvents under suitable conditions in which crystalline Form is stable.

In another aspect, the present application provides process for preparing a crystalline Form-Alpha of Selinexor, which comprises:

a) combining Selinexor with acetone: water mixture;
b) stirring the mixture of step a);
c) isolating crystalline Form-Alpha of Selinexor.

In an embodiment, Selinexor that is used in step a) may be purified by any methods known in the art such as column chromatography, fractional distillation, acid-base treatment, slurring or re-crystallization, before using.

In an embodiment, Selinexor that is used in step a) of this aspect may be either the amorphous form or any other crystalline form of Selinexor or by directly taking a synthetic reaction mixture comprising Selinexor and acetone: water mixture.

In an embodiment, Selinexor may be combined with mixture of acetone and water at any suitable temperatures, such as at about 0° C. to about the reflux temperature of the solvent mixture. The mixture of Selinexor and acetone-water solvent may be prepared preferably at about 0° C. to 60° C.

In an embodiment the mixture of Selinexor and acetone-water may be either a heterogeneous or homogeneous phase.

The acetone to water ratio of the acetone-water mixture may be between about 1:1 to 20:1, preferably between about 1:1 to 15:1.

In an embodiment, the mixture of Selinexor and acetone-water may be optionally filtered to make particle free solution when it is a homogenous clear solution and treated with a decolorizing agent, such as carbon, before filtration.

In an embodiment, Selinexor that may be used in step a) of this aspect may be amorphous form of Selinexor.

In an embodiment, the mixture of Selinexor and acetone-water at step b) may be stirred for sufficient time to complete formation of crystalline Form-Alpha of Selinexor. In an embodiment, the mixture of Selinexor and acetone-water may be stirred for at least 1 hour or more, preferably for at least 24 hours or more and more preferably at least 48 hours or more.

In an embodiment, the mixture of Selinexor and acetone-water may be stirred at suitable temperature for the formation of crystalline Form-Alpha of Selinexor. In an embodiment, the mixture of Selinexor and acetone-water may be stirred at 0° C. and above, preferably between 0° C. to reflux temperature of the solvent used, more preferably between 0° C. and 50° C.

In an embodiment, isolation of crystalline Form-Alpha of Selinexor may be carried out by any methods known in the art or procedures described in the present application. In an embodiment, crystalline Form-Alpha of Selinexor may be isolated by employing any of the techniques, but not limited to: decantation, filtration by gravity or suction, centrifugation, adding solvent to make slurry followed by filtration, or other techniques specific to the equipment used and the like, and optionally washing with a solvent.

Drying process for crystalline Form-Alpha of Selinexor may be carried out in the similar manner as described in the above aspect for crystalline Selinexor.

In another aspect, the present application provides a process for preparing a crystalline Form-Delta of Selinexor, which comprises:

a) combining Selinexor with methanol;
b) stirring the mixture of step a);
c) isolating crystalline Form-Delta of Selinexor.

In an embodiment, Selinexor may be combined with methanol at any suitable temperatures, such as at about 0° C.

to about the reflux temperature of the mixture. The mixture of Selinexor and methanol may be prepared preferably at about 0° C. to 60° C.

In an embodiment the mixture of Selinexor and methanol may be either a heterogeneous or homogeneous phase.

In an embodiment, the mixture of Selinexor and methanol may be optionally filtered to make particle free solution, in case the mixture forms a homogenous clear solution and may be treated with a decolorizing agent, such as carbon, before filtration.

In an embodiment, Selinexor that may be used in step a) of this aspect may be amorphous form of Selinexor.

In an embodiment, the mixture of Selinexor and methanol at step b) may be stirred for sufficient time to complete formation of crystalline Form-Delta of Selinexor. In an embodiment, the mixture of Selinexor and methanol may be stirred for at least 5 minutes or more.

In an embodiment, the mixture of Selinexor and methanol may be stirred at suitable temperature for the formation of crystalline Form-Delta of Selinexor. In an embodiment, the mixture of Selinexor and methanol may be stirred at 0° C. and above, preferably between 0° C. to reflux temperature of the reaction mixture.

In an embodiment, isolation of crystalline Form-Delta of Selinexor may be carried out by any methods known in the art or procedures described in the present application. In an embodiment, crystalline Form-Delta of Selinexor may be isolated by employing any of the techniques, but not limited to: decantation, filtration by gravity or suction, centrifugation, adding solvent to make slurry followed by filtration, or other techniques specific to the equipment used and the like, and optionally washing with a solvent.

In an embodiment, isolated crystalline Form-Delta of Selinexor may be dried in a suitable drying equipment such as tray dryer, vacuum oven, rotatory cone dryer, air oven, fluidized bed dryer, spin flash dryer, flash dryer, or the like. The drying may be carried out at atmospheric pressure or under reduced pressures at temperatures of less than about 100° C., less than about 60° C., less than about 40° C., or any other suitable temperatures. Drying can be carried out at temperatures and times sufficient to achieve desired quality of product. Drying may be carried out for any time period required for obtaining a desired quality, such as from about 15 minutes to 10 hours or longer.

In another aspect, the present application provides a process for preparing a crystalline Form-Epsilon of Selinexor, which comprises:
  a) combining Selinexor with ethanol;
  b) stirring the mixture of step a);
  c) isolating crystalline Form-Epsilon of Selinexor.

In an embodiment, Selinexor may be combined with ethanol at any suitable temperatures, such as at about 0° C. to about the reflux temperature of the reaction mixture. The mixture of Selinexor and ethanol may be prepared preferably at about 0° C. to 60° C.

In an embodiment the mixture of Selinexor and ethanol may be either a heterogeneous or homogeneous phase.

In an embodiment, the mixture of Selinexor and ethanol may be optionally filtered to make particle free solution, in case the mixture forms a homogenous clear solution and may be treated with a decolorizing agent, such as carbon, before filtration.

In an embodiment, Selinexor that may be used in step a) of this aspect may be amorphous form of Selinexor.

In an embodiment, the mixture of Selinexor and ethanol at step b) may be stirred for sufficient time to complete formation of crystalline Form-Epsilon of Selinexor. In an embodiment, the mixture of Selinexor and ethanol may be stirred for at least 5 minutes or more.

In an embodiment, the mixture of Selinexor and ethanol may be stirred at suitable temperature for the formation of crystalline Form-Epsilon of Selinexor.

In an embodiment, the mixture of Selinexor and ethanol may be stirred at 0° C. and above, preferably between 0° C. to reflux temperature of the reaction mixture.

In an embodiment, isolation of crystalline Form-Epsilon of Selinexor may be carried out by any methods known in the art or procedures described in the present application. In an embodiment, crystalline Form-Epsilon of Selinexor may be isolated by employing any of the techniques, but not limited to: decantation, filtration by gravity or suction, centrifugation, adding solvent to make slurry followed by filtration, or other techniques specific to the equipment used and the like, and optionally washing with a solvent.

Drying process for crystalline Form-Epsilon of Selinexor may be carried out in the similar manner as described in the above aspect for crystalline Form-Delta of Selinexor.

In another aspect, the present application provides process for preparing a crystalline Form-Zeta of Selinexor, which comprises:
  a) combining Selinexor with acetic acid and water;
  b) stirring the mixture of step a);
  c) isolating crystalline Form-Zeta of Selinexor.

In an embodiment, Selinexor may be combined with acetic acid and water at any suitable temperatures, such as at about 0° C. to about the reflux temperature of reaction mixture. The mixture of Selinexor with acetic acid and water may be prepared preferably at about 0° C. to 60° C.

In an embodiment the mixture of Selinexor with acetic acid and water may be either a heterogeneous or homogeneous phase.

In an embodiment, the mixture of Selinexor and water may be optionally filtered to make particle free solution, in case the mixture forms a homogenous clear solution and may be treated with a decolorizing agent, such as carbon, before filtration.

In an embodiment, Selinexor that may be used in step a) of this aspect may be amorphous form of Selinexor.

In an embodiment, the mixture of Selinexor with acetic acid and water at step b) may be stirred for sufficient time to complete formation of crystalline Form-Zeta of Selinexor. In an embodiment, the mixture of Selinexor with acetic acid and water may be stirred for at least 5 minutes or more.

In an embodiment, the mixture of Selinexor with acetic acid and water may be stirred at suitable temperature for the formation of crystalline Form-Zeta of Selinexor. In an embodiment, the mixture of Selinexor and water may be stirred at 0° C. and above, preferably between 0° C. to reflux temperature of reaction mixture.

In an embodiment, isolation of crystalline Form-Zeta of Selinexor may be carried out by any methods known in the art or procedures described in the present application. In an embodiment, crystalline Form-Zeta of Selinexor may be isolated by employing any of the techniques, but not limited to: decantation, filtration by gravity or suction, centrifugation, adding solvent to make slurry followed by filtration, or other techniques specific to the equipment used and the like, and optionally washing with a solvent.

Drying process for crystalline Form-Zeta of Selinexor may be carried out in the similar manner as described in the above aspect for crystalline Form-Delta of Selinexor.

In another aspect, the present application provides process for preparing a crystalline Form-Theta of Selinexor, which comprises:

a) providing a solution of Selinexor in formic acid;
b) contacting the solution of step a) with an anti-solvent;
c) isolating crystalline Form-Theta of Selinexor.

In an embodiment, Selinexor may be combined with Formic acid at any suitable temperatures, such as at about 0° C. to about the reflux temperature of the reaction mixture. The mixture of Selinexor in solvent may be prepared preferably at about 0° C. to 50° C.

In an embodiment the mixture of Selinexor and Formic acid may be either a heterogeneous or homogeneous phase.

In an embodiment, the mixture of Selinexor and Formic acid may be optionally filtered to make particle free solution, in case the mixture forms a homogeneous clear solution and may be treated with a decolorizing agent, such as carbon, before filtration.

In an embodiment, the mixture of Selinexor and formic acid may be optionally cooled to suitable temperature.

In an embodiment, the mixture of step a) may be contacted with an anti-solvent. Anti-solvent may be added for sufficient time and at suitable temperature for the formation of crystalline Form-Theta of Selinexor. Anti-solvents may be selected from the group comprising of water; ethers, such as diethyl ether, di-isopropyl ether, tetrahydrofuran, dioxane; aliphatic hydrocarbons, such as hexane, heptane, cyclohexane; aromatic hydrocarbons, such as toluene, xylene and chlorobenzene; or mixtures thereof.

In an embodiment, the mixture of Selinexor and formic acid may be stirred for sufficient time for the formation of crystalline Form-Theta of Selinexor, before or after contacting with anti-solvent.

In an embodiment, isolation of crystalline Form-Theta of Selinexor may be carried out by any methods known in the art or procedures described in the present application. In an embodiment, crystalline Form-Theta of Selinexor may be isolated by employing any of the techniques, but not limited to: decantation, filtration by gravity or suction, centrifugation, adding solvent to make slurry followed by filtration, or other techniques specific to the equipment used and the like, and optionally washing with a solvent.

Drying process for crystalline Form-Theta of Selinexor may be carried out in the similar manner as described in the above aspect for crystalline Form-Delta of Selinexor.

In another aspect, the present application provides process for preparing a crystalline Form-Eta of Selinexor, which comprises:
a) combining Selinexor with nitromethane;
b) stirring the mixture of step a);
c) isolating crystalline Form-Eta of Selinexor.

In an embodiment, Selinexor may be combined with nitromethane at any suitable temperatures, such as at about 0° C. to about the reflux temperature of reaction mixture. The mixture of Selinexor and nitromethane may be prepared preferably at about 0° C. to 60° C.

In an embodiment the mixture of Selinexor and nitromethane may be either a heterogeneous or homogeneous phase.

In an embodiment, the mixture of Selinexor and nitromethane may be optionally filtered to make particle free solution, in case it forms a homogenous clear solution and may be treated with a decolorizing agent, such as carbon, before filtration.

In an embodiment, the mixture of Selinexor and nitromethane at step b) may be stirred for sufficient time to complete formation of crystalline Form-Eta of Selinexor. In an embodiment, the mixture of Selinexor and nitromethane may be stirred for at least 5 minutes or more.

In an embodiment, the mixture of Selinexor and nitromethane may be stirred at suitable temperature for the formation of crystalline Form-Eta of Selinexor. In an embodiment, the mixture of Selinexor and nitromethane may be stirred at 0° C. and above, preferably between 0° C. to reflux temperature of reaction mixture.

In an embodiment, isolation of crystalline Form-Eta of Selinexor may be carried out by any methods known in the art or procedures described in the present application. In an embodiment, crystalline Form-Eta of Selinexor may be isolated by employing any of the techniques, but not limited to: decantation, filtration by gravity or suction, centrifugation, adding solvent to make slurry followed by filtration, or other techniques specific to the equipment used and the like, and optionally washing with a solvent.

In another aspect, the present application provides process for preparing a crystalline Form-Iota of Selinexor, which comprises the step of drying Form-Eta of Selinexor.

In an embodiment, drying Form-Eta of Selinexor may be carried out in suitable drying equipment such as a tray drier optionally under reduced pressure or other drying conditions known in the art such as Buchi rotavapour vacuum drying, rotatory cone vacuum drying; fluid bed drying optionally under nitrogen atmosphere, thin film drying; or the like.

In an embodiment, drying Form-Eta of Selinexor may be carried out at suitable temperatures of about 25° C. and above, optionally under reduced pressure. In an embodiment, drying may be carried out at about 50° C. and above.

In an embodiment, drying Form-Eta of Selinexor may be carried out for sufficient time to complete its conversion to Form-Iota of Selinexor. Drying can be carried out at temperatures and times sufficient to achieve desired quality of product. Drying may be carried out for any time period required for obtaining a desired quality, such as from about 15 minutes to 5 hours or longer.

In another aspect, the present application provides process for preparing a crystalline Form-Kappa of Selinexor, which comprises:
a) combining Selinexor with water;
b) stirring the mixture of step a);
c) isolating crystalline Form-Kappa of Selinexor.

In an embodiment, Selinexor may be combined with water at any suitable temperatures, such as at about 0° C. to about the reflux temperature of reaction mixture. The mixture of Selinexor and water may be prepared preferably at about 0° C. to 60° C.

In an embodiment the mixture of Selinexor and water may be either a heterogeneous or homogeneous phase.

In an embodiment, the mixture of Selinexor and water may be optionally filtered to make particle free solution, in case it forms a homogenous clear solution and may be treated with a decolorizing agent, such as carbon, before filtration.

In an embodiment, Selinexor that may be used in step a) of this aspect may be amorphous form of Selinexor.

In an embodiment, the mixture of Selinexor and water at step b) may be stirred for sufficient time to complete formation of crystalline Form-Kappa of Selinexor. In an embodiment, the mixture of Selinexor and water may be stirred for at least 5 minutes or more.

In an embodiment, the mixture of Selinexor and water may be stirred at suitable temperature for the formation of crystalline Form-Kappa of Selinexor. In an embodiment, the mixture of Selinexor and water may be stirred at 0° C. and above, preferably between 0° C. to reflux temperature of reaction mixture.

In an embodiment, isolation of crystalline Form-Kappa of Selinexor may be carried out by any methods known in the art or procedures described in the present application. In an embodiment, crystalline Form-Kappa of Selinexor may be isolated by employing any of the techniques, but not limited to: decantation, filtration by gravity or suction, centrifugation, adding solvent to make slurry followed by filtration, or other techniques specific to the equipment used and the like, and optionally washing with a solvent.

In another aspect, the present application provides process for preparing a crystalline Form-Lambda of Selinexor, which comprises:
a) combining Selinexor with glycerol;
b) stirring the mixture of step a);
c) isolating crystalline Form-Lambda of Selinexor.

In an embodiment, Selinexor may be combined with glycerol at any suitable temperatures, such as at about 0° C. to about the reflux temperature of the mixture. The mixture of Selinexor and methanol may be prepared preferably at about 0° C. to 60° C.

In an embodiment the mixture of Selinexor and glycerol may be either a heterogeneous or homogeneous phase.

In an embodiment, the mixture of Selinexor and glycerol may be optionally filtered to make particle free solution, in case the mixture forms a homogenous clear solution and may be treated with a decolorizing agent, such as carbon, before filtration.

In an embodiment, Selinexor that may be used in step a) of this aspect may be amorphous form of Selinexor.

In an embodiment, the mixture of Selinexor and glycerol at step b) may be stirred for sufficient time to complete formation of crystalline Form-Lambda of Selinexor. In an embodiment, the mixture of Selinexor and glycerol may be stirred for at least 5 minutes or more.

In an embodiment, the mixture of Selinexor and glycerol may be stirred at suitable temperature for the formation of crystalline Form-Lambda of Selinexor. In an embodiment, the mixture of Selinexor and glycerol may be stirred at 0° C. and above, preferably between 0° C. to reflux temperature of the reaction mixture.

In an embodiment, isolation of crystalline Form-Lambda of Selinexor may be carried out by any methods known in the art or procedures described in the present application. In an embodiment, crystalline Form-Lambda of Selinexor may be isolated by employing any of the techniques, but not limited to: decantation, filtration by gravity or suction, centrifugation, adding solvent to make slurry followed by filtration, or other techniques specific to the equipment used and the like, and optionally washing with a solvent.

In an embodiment, isolated crystalline Form-Lambda of Selinexor may be dried in a suitable drying equipment such as tray dryer, vacuum oven, rotatory cone dryer, air oven, fluidized bed dryer, spin flash dryer, flash dryer, or the like. The drying may be carried out at atmospheric pressure or under reduced pressures at temperatures of less than about 100° C., less than about 60° C., less than about 40° C., or any other suitable temperatures. Drying can be carried out at temperatures and times sufficient to achieve desired quality of product. Drying may be carried out for any time period required for obtaining a desired quality, such as from about 15 minutes to 10 hours or longer.

In another aspect, the present application provides process for preparing a crystalline Form-Mu of Selinexor, which comprises:
a) combining Selinexor with dimethyl formamide;
b) stirring the mixture of step a);
c) isolating crystalline Form-Mu of Selinexor.

In an embodiment, Selinexor may be combined with dimethyl formamide at any suitable temperatures, such as at about 0° C. to about the reflux temperature of the reaction mixture. The mixture of Selinexor and dimethyl formamide may be prepared preferably at about 0° C. to 60° C.

In an embodiment the mixture of Selinexor and dimethyl formamide may be either a heterogeneous or homogeneous phase.

In an embodiment, the mixture of Selinexor and dimethyl formamide may be optionally filtered to make particle free solution, in case the mixture forms a homogenous clear solution and may be treated with a decolorizing agent, such as carbon, before filtration.

In an embodiment, Selinexor that may be used in step a) of this aspect may be amorphous or crystalline form of Selinexor.

In an embodiment, the mixture of Selinexor and dimethyl formamide at step b) may be stirred for sufficient time to complete formation of crystalline Form-Mu of Selinexor. In an embodiment, the mixture of Selinexor and dimethyl formamide may be stirred for at least 5 minutes or more.

In an embodiment, the mixture of Selinexor and dimethyl formamide may be stirred at suitable temperature for the formation of crystalline Form-Mu of Selinexor.

In an embodiment, the mixture of Selinexor and dimethyl formamide may be stirred at 0° C. and above, preferably between 0° C. to reflux temperature of the reaction mixture.

In an embodiment, the mixture of Selinexor and dimethyl formamide may be optionally evaporated either under atmospheric pressure or reduced pressure. In an embodiment, the mixture of Selinexor and dimethyl formamide may be subjected to slow solvent evaporation.

In an embodiment, isolation of crystalline Form-Mu of Selinexor may be carried out by any methods known in the art or procedures described in the present application. In an embodiment, crystalline Form-Mu of Selinexor may be isolated by employing any of the techniques, but not limited to: decantation, filtration by gravity or suction, centrifugation, adding solvent to make slurry followed by filtration, or other techniques specific to the equipment used and the like, and optionally washing with a solvent.

In another aspect, the present application provides process for preparing a crystalline Form-Nu of Selinexor, which comprises:
a) combining Selinexor with dimethyl acetamide;
b) stirring the mixture of step a);
c) isolating crystalline Form-Nu of Selinexor.

In an embodiment, Selinexor may be combined with dimethyl acetamide at any suitable temperatures, such as at about 0° C. to about the reflux temperature of reaction mixture. The mixture of Selinexor and dimethyl acetamide may be prepared preferably at about 0° C. to 60° C.

In an embodiment the mixture of Selinexor and dimethyl acetamide may be either a heterogeneous or homogeneous phase.

In an embodiment, the mixture of Selinexor and dimethyl acetamide may be optionally filtered to make particle free solution, in case the mixture forms a homogenous clear solution and may be treated with a decolorizing agent, such as carbon, before filtration.

In an embodiment, Selinexor that may be used in step a) of this aspect may be amorphous or crystalline form of Selinexor.

In an embodiment, the mixture of Selinexor and dimethyl acetamide at step b) may be stirred for sufficient time to complete formation of crystalline Form-Nu of Selinexor. In an embodiment, the mixture of Selinexor and dimethyl acetamide may be stirred for at least 5 minutes or more.

In an embodiment, the mixture of Selinexor and dimethyl acetamide may be stirred at suitable temperature for the formation of crystalline Form-Nu of Selinexor. In an embodiment, the mixture of Selinexor and dimethyl acetamide may be stirred at 0° C. and above, preferably between 0° C. to reflux temperature of reaction mixture.

In an embodiment, the mixture of Selinexor and dimethyl formamide may be optionally evaporated either under atmospheric pressure or reduced pressure. In an embodiment, the mixture of Selinexor and dimethyl formamide may be subjected to slow solvent evaporation.

In an embodiment, isolation of crystalline Form-Nu of Selinexor may be carried out by any methods known in the art or procedures described in the present application. In an embodiment, crystalline Form-Nu of Selinexor may be isolated by employing any of the techniques, but not limited to: decantation, filtration by gravity or suction, centrifugation, adding solvent to make slurry followed by filtration, or other techniques specific to the equipment used and the like, and optionally washing with a solvent.

In another aspect, the present application provides process for preparing a crystalline Form-Xi of Selinexor, which comprises the step of drying Form-kappa of Selinexor.

In an embodiment, drying Form-kappa of Selinexor may be carried out in suitable drying equipment such as a tray drier optionally under reduced pressure or other drying conditions known in the art such as Buchi rotavapour vacuum drying, rotatory cone vacuum drying; fluid bed drying optionally under nitrogen atmosphere, thin film drying; or the like.

In an embodiment, drying Form-kappa of Selinexor may be carried out at suitable temperatures of about 25° C. and above, optionally under reduced pressure.

In an embodiment, drying Form-kappa of Selinexor may be carried out for sufficient time to complete its conversion to Form-Xi of Selinexor. Drying can be carried out at temperatures and times sufficient to achieve desired quality of product. Drying may be carried out for any time period required for obtaining a desired quality, such as from about 15 minutes to 1 hour or longer.

In another aspect, the present application provides process for preparing a crystalline Form-Kappa of Selinexor, which comprises:
 a) providing a solution of Selinexor in methanol or a mixture thereof;
 b) contacting the solution of step a) with water;
 c) isolating crystalline Form-Kappa of Selinexor.

In an embodiment, Selinexor that may be used in step a) may be any other crystalline or amorphous form. In an embodiment, solution of step a) may be provided by combining Selinexor with methanol or a mixture thereof, optionally heating the mixture to obtain a homogeneous solution. The solution may be filtered to make it particle free, after optionally treating with carbon.

Step b) of this aspect may be carried out by contacting the solution of step a) with water. In an embodiment, the solution of step a) may be contacted with water at a suitable temperature of about 0° C. and above. In an embodiment, the solution of step a) may be optionally cooled either before or after contacting it with water.

In an embodiment, either the solution of step a) may be added to water or water may be added to it. The ratio of methanol to water that may be used vary between about 1:1 and 1:50. In embodiment, addition may be carried out at a suitable temperature of about 0° C. and above for sufficient time to nucleate and stabilize crystalline form kappa.

In an embodiment, the mixture of step b) may be stirred for sufficient time to obtain crystalline form kappa of Selinexor for at least 5 minutes or more at about 0° C. or above.

In an embodiment, isolation of crystalline Form-kappa of Selinexor at step c) may be carried out by any methods known in the art or procedures described in the present application. In an embodiment, crystalline Form-kappa of Selinexor may be isolated by employing any of the techniques, but not limited to: decantation, filtration by gravity or suction, centrifugation, adding solvent to make slurry followed by filtration, or other techniques specific to the equipment used and the like, and optionally washing with a solvent.

Selinexor that is used any of the aspects of present application may be purified by any methods known in the art such as column chromatography, fractional distillation, acid-base treatment, slurring or re-crystallization, before using.

Selinexor that is used any of the aspects of present application may be either in amorphous form or any other crystalline form of Selinexor or by directly taking a synthetic reaction mixture comprising Selinexor.

In embodiments, for the preparation of the crystalline from of Selinexor selected from the group comprising Form-Alpha, Form-Delta, Form-Epsilon, Form-Zeta, Form-Eta, Form-Theta, Form-Iota, Form-Kappa, Form-Lambda, Form-Mu, Form-Nu and Form-Xi or mixtures thereof, at least one additional solvent may be optionally used, other than the solvent mentioned in their respective aspects.

In another aspect, the present application provides a process for the preparation of an amorphous form of Selinexor, comprising the steps of:
 a) providing a solution of Selinexor in a solvent or a mixture thereof;
 b) removing the solvent from the solution obtained in step a); and
 c) isolating the amorphous form of Selinexor.
 d) optionally combining amorphous form of step c) with at least one pharmaceutically acceptable excipient.

In an embodiment, Selinexor that is used in step a) may be purified by any methods known in the art such as column chromatography, fractional distillation, acid-base treatment, slurring or re-crystallization, before using.

In an embodiment, Selinexor that is used in step a) of this aspect may be either a crystalline form of Selinexor or by directly taking a synthetic reaction mixture comprising Selinexor and a solvent or a mixture of solvents.

In an embodiment, solvent at step a) of this aspect may be selected from C1-C6 alcohols, C3-C6 ketones, C5-C8 aliphatic or aromatic hydrocarbons, C3-C6 esters, C2-C6 aliphatic or cyclic ethers, C2-C6 nitriles, halogenated hydrocarbons, water or mixtures thereof.

In preferred embodiment, the solvent may be selected from the group comprising of alcohol solvents such as methanol, ethanol, 2-propanol, 1-butanol, 2-butanol, 1-pentanol, 2-pentanol, 3-pentanol; ketone solvents such as acetone, methyl ethyl ketone, methyl isobutyl ketone; esters solvents such as methyl acetate, ethyl acetate, isopropyl acetate; water and mixtures thereof.

In an embodiment, providing a solution at step a) may be carried out by dissolving Selinexor in a solvent or by taking the reaction mixture containing Selinexor directly. In an embodiment, a solution of Selinexor can be prepared at any suitable temperatures, such as about 0° C. to about the reflux temperature of the solvent used. Stirring and heating may be used to reduce the time required for the dissolution process.

In an embodiment, a solution of Selinexor may be filtered to make it clear, free of unwanted particles. In embodiments, the obtained solution may be optionally treated with an adsorbent material, such as carbon and/or hydrose, to remove colored components, etc., before filtration.

In an embodiment, removal of solvent at step b) may be carried out by methods known in the art or any procedure disclosed in the present application. In preferred embodiments, removal of solvent may include, but not limited to: solvent evaporation under atmospheric pressure or reduced pressure/vacuum such as a rotational distillation using Büchi® Rotavapor®, spray drying, freeze drying, thin film drying, agitated thin film drying and the like.

In preferred embodiment, the solvent may be removed under reduced pressures and at temperatures of less than about 100° C., less than about 60° C., less than about 40° C., less than about 20° C., less than about 0° C., less than about −20° C., less than about −40° C., less than about −60° C., less than about −80° C., or any other suitable temperatures.

In an embodiment, the isolation of an amorphous form of Selinexor at step c) involves recovering the solid obtained in step b). The solid obtained from step b) may be recovered using techniques such as by scraping, or by shaking the container, or adding solvent to make slurry followed by filtration, or other techniques specific to the equipment used. In an embodiment, the amorphous form of Selinexor obtained from step b) may be optionally dried before or after isolating it at step c).

Amorphous form of Selinexor obtained at step c) may be optionally combined with at least one pharmaceutically acceptable excipient at step d).

In an embodiment, amorphous form of Selinexor may be combined with excipient using a technique known in art or by the procedures disclosed in the present application.

In preferred embodiment, amorphous form of Selinexor may be combined with excipient either by physical blending of both the solid components or by suspending both the components in a suitable solvent and conditions, such that both the components remain unaffected. Blending may be carried out using techniques known in art such as rotatory cone dryer, fluidized bed dryer or the like optionally under reduced pressure/vacuum or inert atmosphere such nitrogen at suitable temperature and sufficient time to obtain uniform composition of amorphous form of Selinexor and at least one pharmaceutically acceptable excipient.

In an embodiment, amorphous form of Selinexor may be combined with the excipient by evaporating the suspension or solution of amorphous form of Selinexor and at least one pharmaceutically acceptable excipient.

In an embodiment, pharmaceutically acceptable excipient may include, but not limited to an inorganic oxide such as $SiO_2$, $TiO_2$, $ZnO_2$, $ZnO$, $Al_2O_3$ and zeolite; a water insoluble polymer is selected from the group consisting of cross-linked polyvinyl pyrrolidinone, cross-linked cellulose acetate phthalate, cross-linked hydroxypropyl methyl cellulose acetate succinate, microcrystalline cellulose, polyethylene/polyvinyl alcohol copolymer, polyethylene/polyvinyl pyrrolidinone copolymer, cross-linked carboxymethyl cellulose, sodium starch glycolat, and cross-linked styrene divinyl benzene or any other excipient at any aspect of present application.

In preferred embodiment, pharmaceutically acceptable excipient may be selected from the group consisting of silicon dioxide, e.g. colloidal or fumed silicon dioxide or porous silica; copolymers, such as polyethylene/polyvinyl alcohol copolymer, polyethylene/polyvinyl pyrrolidinone copolymer; and cellulose, preferably microcrystalline cellulose.

Amorphous form of Selinexor isolated at step c) or d) may be dried in suitable drying equipment such as vacuum oven, rotatory cone dryer, air oven, fluidized bed dryer, spin flash dryer, flash dryer, or the like. The drying may be carried out at atmospheric pressure or under reduced pressures at temperatures of less than about 100° C., less than about 60° C., less than about 40° C., or any other suitable temperatures. The drying may be carried out for any time period required for obtaining a desired quality, such as from about 15 minutes to 10 hours or longer.

In an aspect, the present application provides pharmaceutical composition comprising amorphous form of Selinexor and at least one pharmaceutically acceptable excipient.

In another aspect, the present application provides a process for the preparation of an amorphous solid dispersion of Selinexor, comprising the steps of:
a) providing a solution of Selinexor and at least one pharmaceutically acceptable excipient in a solvent or a mixture thereof;
b) removing the solvent from the solution obtained in step a), and
c) isolating the amorphous solid dispersion of Selinexor.
d) optionally combining amorphous solid dispersion of step c) with at least one additional pharmaceutically acceptable excipient.

In an embodiment, Selinexor that is used in step a) may be purified by any methods known in the art such as column chromatography, fractional distillation, acid-base treatment, slurring or re-crystallization, before using.

In an embodiment, Selinexor that is used in step a) of this aspect may be either a crystalline form of Selinexor or by directly taking a synthetic reaction mixture comprising Selinexor and a solvent or a mixture of solvents.

In an embodiment, solvent at step a) of this aspect may be selected from C1-C6 alcohols, C3-C6 ketones, C5-C8 aliphatic or aromatic hydrocarbons, C3-C6 esters, C2-C6 aliphatic or cyclic ethers, C2-C6 nitriles, halogenated hydrocarbons, water or mixtures thereof.

In preferred embodiment, the solvent may be selected from the group consisting of alcohol solvents such as methanol, ethanol, 2-propanol, 1-butanol, 2-butanol, 1-pentanol, 2-pentanol, 3-pentanol; ketone solvents such as acetone, methyl ethyl ketone, methyl isobutyl ketone; esters solvents such as methyl acetate, ethyl acetate, isopropyl acetate; water and mixtures thereof.

In an embodiment, at least one pharmaceutically acceptable excipient of this aspect may be selected from the group consisting of polyvinyl pyrrolidone, povidone K-30, povidone K-60, Povidone K-90, polyvinylpyrrolidone vinylacetate, co-povidone NF, polyvinylacetal diethylaminoacetate (AEA®), polyvinyl acetate phthalate, polysorbate 80, polyoxyethylene-polyoxypropylene copolymers (Poloxamer® 188), polyoxyethylene (40) stearate, polyethyene glycol monomethyl ether, polyethyene glycol, poloxamer 188, pluronic F-68, methylcellulose, methacrylic acid copolymer (Eudragit), hydroxypropylmethyl cellulose phthalate, hydroxypropylmethyl ellulose acetate succinate, hydroxypropyl methyl ellulose, hydroxypropyl cellulose SL, hydroxyethyl cellulose, gelucire 44/14, ethyl cellulose, D-alpha-tocopheryl polyethylene glycol 1000 succinate, cellulose acetate phthalate, carboxymethylethylcelluloseand the like; cyclodextrins, gelatins, hypromellose phthalates, sugars, polyhydric alcohols, and the like; water soluble sugar excipients, preferably having low hygroscopicity, which include, but are not limited to, mannitol, lactose, fructose, sorbitol, xylitol, maltodextrin, dextrates, dextrins, lactitol and the like; polyethylene oxides, polyoxyethylene derivatives, polyvinyl alcohols, propylene glycol derivatives and the like; organic amines such as alkyl amines (primary, secondary, and tertiary), aromatic amines, alicyclic amines, cyclic amines, aralkyl amines, hydroxylamine or its derivatives, hydrazine or its derivatives, and guanidine or its derivatives, or any other excipient at any aspect of present application. The use of mixtures of more than one of the pharmaceutical excipients to provide desired release profiles or for the enhancement of stability is within the scope of this invention. Also, all viscosity grades, molecular weights, commercially available products, their copolymers, and mixtures are all within the scope of this invention without limitation.

In an embodiment, providing a solution at step a) may be carried out by dissolving Selinexor and at least one pharmaceutically acceptable excipient in a solvent simultaneously or by dissolving components in a solvent separately to form individual solutions and combining those solutions later.

In an embodiment, a solution of Selinexor and the excipient may be prepared at any suitable temperatures, such as about 0° C. to about the reflux temperature of the solvent used. Stirring and heating may be used to reduce the time required for the dissolution process.

In an embodiment, a solution of Selinexor and the excipient may be filtered to make it clear, free of unwanted particles. In embodiments, the obtained solution may be optionally treated with an adsorbent material, such as carbon and/or hydrose, to remove colored components, etc., before filtration.

In an embodiment, removal of solvent at step b) may be carried out by methods known in the art or any procedure disclosed in the present application. In preferred embodiments, removal of solvent may include, but not limited to: solvent evaporation under atmospheric pressure or reduced pressure/vacuum such as a rotational distillation using Büchi® Rotavapor®, spray drying, freeze drying, agitated thin film drying and the like.

In preferred embodiment, the solvent may be removed under reduced pressures, at temperatures of less than about 100° C., less than about 60° C., less than about 40° C., less than about 20° C., less than about 0° C., less than about −20° C., less than about −40° C., less than about −60° C., less than about −80° C., or any other suitable temperatures.

In an embodiment, the isolation of an amorphous solid dispersion of Selinexor and excipient at step c) involves recovering the solid obtained in step b). The solid obtained from step b) may be recovered using techniques such as by scraping, or by shaking the container, or adding solvent to make slurry followed by filtration, or other techniques specific to the equipment used.

In an embodiment, the amorphous solid dispersion of Selinexor and excipient obtained from step b) may be optionally dried before or after isolating at step c).

Amorphous solid dispersion of Selinexor obtained at step c) may be optionally combined with at least one additional pharmaceutically acceptable excipient at step d).

In an embodiment, amorphous solid dispersion of Selinexor may be combined with additional excipient using a technique known in art or by the procedures disclosed in the present application.

In preferred embodiment, amorphous solid dispersion of the present application may be combined with additional excipient either by physical blending of both the solid components or by suspending both the components in a solvent and conditions, such that both the components remain unaffected. Blending may be carried out using techniques known in art such as rotatory cone dryer, fluidized bed dryer or the like optionally under reduced pressure/vacuum or inert atmosphere such nitrogen at suitable temperature and sufficient time to obtain uniform composition of amorphous solid dispersion of Selinexor with pharmaceutically acceptable excipient and at least one additional pharmaceutically acceptable excipient.

In an embodiment, amorphous solid dispersion of the present application may be combined with additional excipient by evaporating the suspension or solution of amorphous solid dispersion of Selinexor and additional excipient.

In an embodiment, pharmaceutically acceptable additional excipient may be same or different from the excipient used in the preparation of amorphous solid dispersion of Selinexor. Additional excipient may include, but not limited to an inorganic oxide such as $SiO_2$, $TiO_2$, $ZnO_2$, $ZnO$, $Al_2O_3$ and zeolite; a water insoluble polymer is selected from the group consisting of cross-linked polyvinyl pyrrolidinone, cross-linked cellulose acetate phthalate, cross-linked hydroxypropyl methyl cellulose acetate succinate, microcrystalline cellulose, polyethylene/polyvinyl alcohol copolymer, polyethylene/polyvinyl pyrrolidinone copolymer, cross-linked carboxymethyl cellulose, sodium starch glycolat, and cross-linked styrene divinyl benzene or any other excipient at any aspect of present application.

In preferred embodiment, pharmaceutically acceptable additional excipient may be selected from the group consisting of silicon dioxide, e.g. colloidal or fumed silicon dioxide or porous silica; copolymers, such as polyethylene/polyvinyl alcohol copolymer, polyethylene/polyvinyl pyrrolidinone copolymer; and cellulose, preferably microcrystalline cellulose.

Amorphous solid dispersion of Selinexor isolated at step c) or d) may be dried in a suitable drying equipment such as tray dryer, vacuum oven, rotatory cone dryer, air oven, fluidized bed dryer, spin flash dryer, flash dryer, or the like. The drying may be carried out at atmospheric pressure or under reduced pressures at temperatures of less than about 100° C., less than about 60° C., less than about 40° C., or any other suitable temperatures. The drying may be carried out for any time period required for obtaining a desired quality, such as from about 15 minutes to 10 hours or longer.

In an aspect, the present application provides pharmaceutical composition comprising amorphous solid dispersion of Selinexor with at least one pharmaceutically acceptable excipient and at least one additional pharmaceutically acceptable excipient.

In an aspect, the present application provides pharmaceutical compositions comprising amorphous Selinexor and at least one pharmaceutically acceptable excipient, in particular in the form of solid dispersions and adsorbates, and a process for preparing the same. In embodiments, the pharmaceutically acceptable excipient is selected from the excipients at any aspect of present application.

In embodiments, the present application provides adsorbates, wherein Selinexor is associated with a substrate. Substrate may be a particulate and/or porous substrate, wherein this substrate has an outer and/or inner surface onto which the API may be adsorbed. This means that if the substrate has pores, these pores are filled by the Selinexor and the substrate remains unaffected, it does not, at least not essentially, change during and/or after the adsorption. In embodiments, the substrate is selected from the excipients at any aspect of present application.

Amorphous form of Selinexor or its solid dispersion may be obtained alternatively either by employing a melt-extrusion technique or by combining a solution of Selinexor as obtained any of the aspects of present application with a anti-solvent. In embodiment, amorphous product may be obtained by employing suitable melt-extrusion conditions or any of the procedures known in the art for obtaining amorphous product by melt-extrusion technique. In embodiment, solution of Selinexor may be combined with the anti-solvent at suitable temperature and for sufficient time to obtain amorphous product. Anti-solvent is a solvent, wherein Selinexor has low solubility and it may include, but not limited to aliphatic or cyclic ethers solvents, aliphatic or aromatic hydrocarbons or the like.

In an aspect, the present application provides pharmaceutical composition comprising Selinexor and at least one pharmaceutically acceptable excipient, wherein Selinexor may be selected from group comprising of crystalline Form-Alpha, Form-Beta, Form-Gamma, Form-Delta, Form-Epsilon, Form-Zeta, Form-Eta, Form-Theta, Form-Iota, Form-Kappa, Form-Lambda, Form-Mu, Form-Nu and Form-Xi of Selinexor or mixtures thereof.

In another aspect, the present application provides Selinexor or its pharmaceutical composition comprising Selinexor having a chemical purity of at least 99% by HPLC or at least 99.5% by HPLC or at least 99.9% by HPLC. In embodiment, Selinexor may be selected from group comprising of crystalline Form-Alpha, Form-Beta, Form-Gamma, Form-Delta, Form-Epsilon, Form-Zeta, Form-Eta, Form-Theta, Form-Iota, Form-Kappa, Form-Lambda, Form-Mu, Form-Nu, Form-Xi and amorphous form of Selinexor or mixtures thereof.

In another aspect, the present application provides Selinexor or its pharmaceutical composition comprising Selinexor having particle size ($D_{90}$) of less than 100 microns or less than 50 microns or less than 20 microns. In embodiments, Selinexor may be selected from group comprising of crystalline Form-Alpha, Form-Beta, Form-Gamma, Form-Delta, Form-Epsilon, Form-Zeta, Form-Eta, Form-Theta, Form-Iota, Form-Kappa, Form-Lambda, Form-Mu, Form-Nu and amorphous form of Selinexor or mixtures thereof.

X-ray powder diffraction patterns described herein were generated using a Bruker AXS D8 Advance powder X-ray diffractometer or PANalytical X'pert pro X-ray diffractometer with a copper K-alpha radiation source. Generally, a diffraction angle (2θ) in powder X-ray diffractometry may have an error in the range of ±0.2°. Therefore, the aforementioned diffraction angle values should be understood as including values in the range of about ±0.2°. Accordingly, the present invention includes not only crystals whose peak diffraction angles in powder X-ray diffractometry completely coincide with each other, but also crystals whose peak diffraction angles coincide with each other with an error of about ±0.2°. Therefore, in the present specification, the phrase "having a diffraction peak at a diffraction angle (2θ) ±0.2° of 6.3°" means "having a diffraction peak at a diffraction angle (2θ) of 6.1° to 6.5°. Although the intensities of peaks in the x-ray powder diffraction patterns of different batches of a compound may vary slightly, the peak relationships and the peak locations are characteristic for a specific polymorphic form. The relative intensities of the PXRD peaks may vary somewhat, depending on factors such as the sample preparation technique, crystal size distribution, various filters used, the sample mounting procedure, and the particular instrument employed. Moreover, instrumental variation and other factors may slightly affect the 2-theta values. Therefore, the term "substantially" in the context of PXRD is meant to encompass that peak assignments may vary by plus or minus about 0.2°. Moreover, new peaks may be observed or existing peaks may disappear, depending on the type of the machine or the settings (for example, whether a filter is used or not).

Certain specific aspects and embodiments of the present application will be explained in greater detail with reference to the following examples, which are provided only for purposes of illustration and should not be construed as limiting the scope of the application in any manner. Variations of the described procedures, as will be apparent to those skilled in the art, are intended to be within the scope of the present application.

Definitions

The term "about" when used in the present application preceding a number and referring to it, is meant to designate any value which lies within the range of ±10%, preferably within a range of ±5%, more preferably within a range of ±2%, still more preferably within a range of ±1% of its value. For example "about 10" should be construed as meaning within the range of 9 to 11, preferably within the range of 9.5 to 10.5, more preferably within the range of 9.8 to 10.2, and still more preferably within the range of 9.9 to 10.1.

The term "solvent" when used in the present application is a solvent that does not react with the reactants or reagents under conditions that cause the chemical reaction indicated to take place.

The terms "crystalline form of Selinexor" or "crystalline Selinexor" includes solvates, hydrates, and anhydrates of Selinexor. The percent crystallinity of any of the crystalline forms of Selinexor described herein can vary with respect to the total amount of Selinexor. In particular, certain embodiments provide for the percent crystallinity of a crystalline form of Selinexor being at least 10%, at least 20%, at least 30%, at least 40%, at least 50%, at least, 60%, at least 70%, at least 80%, at least 90%, at least 95%, or at least 99%. In some embodiments, the percent crystallinity can be substantially 100%, where substantially 100% indicates that the entire amount of Selinexor appears to be crystalline as best can be determined using methods known in the art.

The terms "amorphous form of Selinexor" and "amorphous Selinexor" indicate that the Selinexor is present in substantially amorphous state in the composition (e.g. solid dispersion, adsorbate or pharmaceutical composition). "Substantially" amorphous denotes that 90%, preferably 95% or 99%, more preferably all of the Selinexor being present in the solid dispersion, on the adsorbate or in the pharmaceutical composition is amorphous. In other words, an "amorphous" Selinexor composition denotes a Selinexor-containing composition, which does not contain substantial amounts, preferably does not contain noticeable amounts, of crystalline portions of Selinexor e.g. measurable upon X-ray powder diffraction analysis.

The term "solid dispersion" when used in the present application, denotes a state where most of the Selinexor, preferably 90%, 95% or all of the Selinexor of the solid dispersion, is homogeneously molecularly dispersed in a solid polymer matrix. Preferably solid dispersion, relates to a molecular dispersion where the API (active pharmaceutical ingredient) and polymer molecules are uniformly but irregularly dispersed in a non-ordered way. In other words, in a solid dispersion, the two components (polymer and API) form a homogeneous one-phase system, where the particle size of the API in the solid dispersion is reduced to its molecular size. In a preferred embodiment, in the solid dispersion according to the present invention no chemical bonds can be detected between the API and the polymer. In order to arrive at such a solid dispersion, preferably solid solution, it is required to have a substantial amount of API dissolved in a solvent at least at one time point during preparation of said solid dispersion.

The term "adsorbate" when used in the present application, specifies that the Selinexor is, preferably evenly, and preferably homogeneously, distributed on the inner and/or outer surface of the particulate substrate.

An "alcohol" is an organic compound containing a carbon bound to a hydroxyl group. "C1-C6 alcohols" include, but are not limited to, methanol, ethanol, 2-nitroethanol, 2-fluoroethanol, 2,2,2-trifluoroethanol, hexafluoroisopropyl alcohol, ethylene glycol, 1-propanol, 2-propanol (isopropyl alcohol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, phenol, glycerol, or the like.

An "aliphatic hydrocarbon" is a liquid hydrocarbon compound, which may be linear, branched, or cyclic and may be saturated or have as many as two double bonds. A liquid hydrocarbon compound that contains a six-carbon group having three double bonds in a ring is called "aromatic." Examples of "C5-C8 aliphatic or aromatic hydrocarbons" include, but are not limited to, n-pentane, isopentane, neopentane, n-hexane, isohexane, 3-methylpentane, 2,3-dimethylbutane, neohexane, n-heptane, isoheptane, 3-methylhexane, neoheptane, 2,3-dimethylpentane, 2,4-dimethylpentane, 3,3-dimethylpentane, 3-ethylpentane, 2,2,3-trimethylbutane, n-octane, isooctane, 3-methylheptane, neooctane, cyclohexane, methylcyclohexane, cycloheptane, benzene, toluene, ethylbenzene, m-xylene, o-xylene, p-xylene, trimethylbenzene, chlorobenzene, fluorobenzene, trifluorotoluene, anisole, or any mixtures thereof.

An "ester" is an organic compound containing a carboxyl group —(C═O)—O— bonded to two other carbon atoms. "C3-C6 esters" include, but are not limited to, ethyl acetate, n-propyl acetate, n-butyl acetate, isobutyl acetate, t-butyl acetate, ethyl formate, methyl acetate, methyl propanoate, ethyl propanoate, methyl butanoate, ethyl butanoate, or the like.

An "ether" is an organic compound containing an oxygen atom —O— bonded to two other carbon atoms. "C2-C6 ethers" include, but are not limited to, diethyl ether, diisopropyl ether, methyl t-butyl ether, glyme, diglyme, tetrahydrofuran, 2-methyltetrahydrofuran, 1,4-dioxane, dibutyl ether, dimethylfuran, 2-methoxyethanol, 2-ethoxyethanol, anisole, or the like.

A "halogenated hydrocarbon" is an organic compound containing a carbon bound to a halogen. Halogenated hydrocarbons include, but are not limited to, dichloromethane, 1,2-dichloroethane, trichloroethylene, perchloroethylene, 1,1,1-trichloroethane, 1,1,2-trichloroethane, chloroform, carbon tetrachloride, or the like. A "ketone" is an organic compound containing a carbonyl group —(C═O)— bonded to two other carbon atoms. "C3-C6 ketones" include, but are not limited to, acetone, ethyl methyl ketone, diethyl ketone, methyl isobutyl ketone, ketones, or the like. A "nitrile" is an organic compound containing a cyano —(C≡N) bonded to another carbon atom. "C2-C6 Nitriles" include, but are not limited to, acetonitrile, propionitrile, butanenitrile, or the like.

EXAMPLES

Example-1: Preparation of isopropyl (Z)-3-(3-(3,5-bis(trifluoromethyl)phenyl)-1H-1,2,4-triazol-1-yl)acrylate

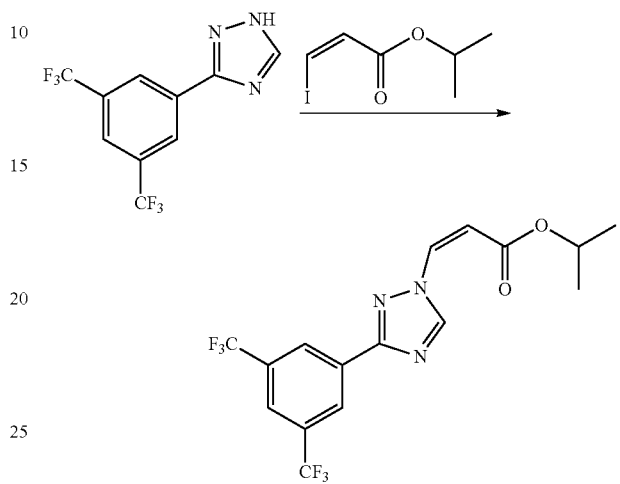

3-(3,5-bis(trifluoromethyl)phenyl)-1H-1,2,4-triazole (250 g) was dissolved in tetrahydrofuran (2 l) under nitrogen atmosphere at 27° C. and cooled to −5° C. 1,4-diazabicyclo[2.2.2]octane (DABCO, 199.5 g) was added to the reaction mixture at −5° C. and stirred at the same temperature for 40 minutes. Isopropyl (Z)-3-iodoacrylate (234.8 g in 500 mL of tetrahydrofuran) was added drop wise to the reaction mixture in 1 hour 10 minutes at −5° C. and stirred at the same temperature for 2 hours. After the completion of the reaction, the reaction mixture was added to ice cold water (2 l) and separated the organic layer. The aqueous layer was extracted with ethyl acetate (2×1 l). The combined organic layer was washed with brine solution (1 l) and dried over sodium sulphate. The dried solution was evaporated completely under vacuum at 40° C. to obtain crude product with HPLC purity of 93.53% The crude product was triturated with hexane (700 mL) and stirred for 20 minutes at −30° C. and filtered the solid. Trituration of crude product with hexane was repeated for three times and dried under vacuum to obtain the title compound with HPLC purity of 97.46% and trans-isomer content of 0.66%. Yield: 297 g Example-2: Preparation of (Z)-3-(3-(3,5-bis(trifluoromethyl)phenyl)-1H-1,2,4-triazol-1-yl)acrylic acid

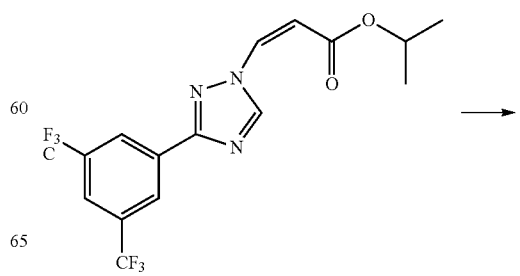

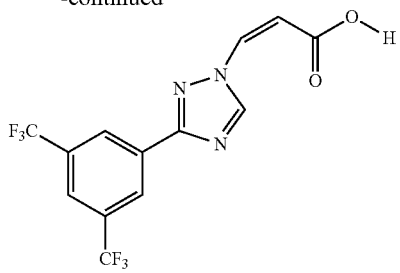

To a mixture of tetrahydrofuran (300 mL) and water (300 mL), Isopropyl (Z)-3-(3-(3,5-bis(trifluoromethyl)phenyl)-1H-1,2,4-triazol-1-yl)acrylate (30 g) was added and cooled to 0° C. Lithium hydroxide monohydrate (16.03 g) under cooling condition at 0° C. was added to the reaction mixture and stirred the reaction mixture at same temperature for 7 hours. After completion of the reaction, 2 N HCl (180 mL) was added to adjust the pH of the reaction mixture to 2 and extracted it with ethyl acetate (300 mL). Organic layer was dried over sodium sulphate and evaporated under vacuum at 40° C. The crude compound was stirred with hexane (150 mL) and filtered the solid. Dried the compound under vacuum at 40° C. for 0.5 hour to obtain the title compound with HPLC purity of 97.25% with trans-isomer content of 3%. Yield: 24 g Example-3: Purification of (Z)-3-(3-(3,5-bis(trifluoromethyl)phenyl)-1H-1,2,4-triazol-1-yl)acrylic acid

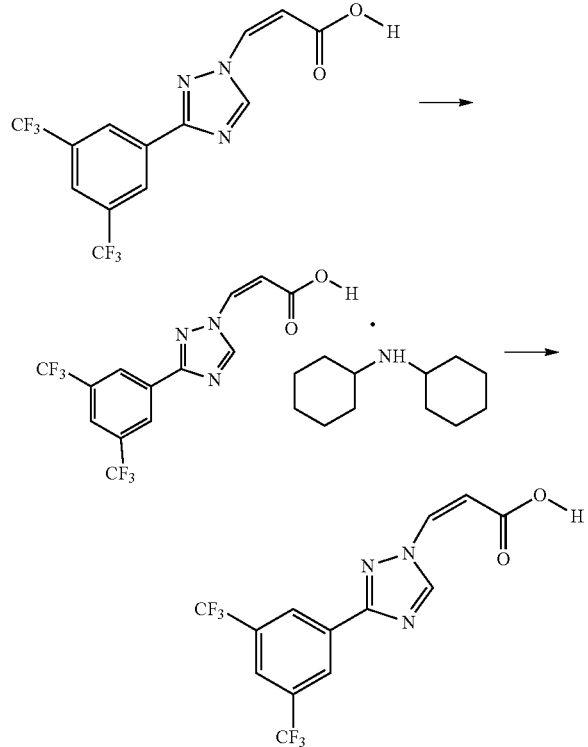

A mixture of (Z)-3-(3-(3,5-bis(trifluoromethyl)phenyl)-1H-1,2,4-triazol-1-yl)acrylic acid (24 g) and acetone (240 mL) was stirred for complete dissolution at 30° C. Dicyclohexyl amine (15 mL) was added drop wise for 20 minutes under stirring at the same temperature. Acetone (50 mL) was added to the reaction mixture and stirred for 2 hours at 27° C. Filtered the solid and washed with hot acetone (150 mL) and dried in vacuum drier at 30° C. for 1 hour to obtain the Dicyclohexyl amine salt of (Z)-3-(3-(3,5-bis(trifluoromethyl)phenyl)-1H-1,2,4-triazol-1-yl)acrylic acid. To the above salt, dichloromethane (150 mL) and water (100 mL) was added and stirred for complete dissolution at 30 and adjusted the pH of the solution with 2 N sulphuric acid (100 mL) to 2. Filtered the reaction mixture and washed the product with water (100 mL) and then with hexane (150 mL). The solid was dried under vacuum at 40° C. for 0.5 hour to obtain title compound with HPLC purity 99.98% with no detectable content of trans-isomer. Yield: 17 g Example-4: Preparation of Selinexor

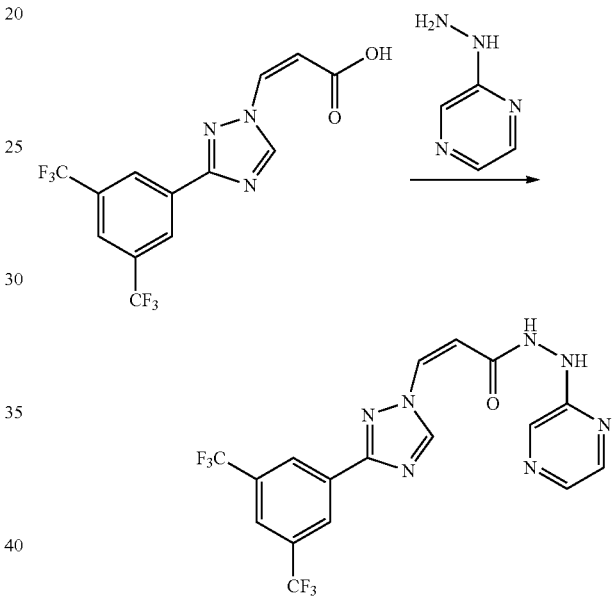

(Z)-3-(3-(3,5-bis(trifluoromethyl)phenyl)-1H-1,2,4-triazol-1-yl)acrylic acid (10 g) was combined with a mixture of acetonitrile (100 mL) and ethyl acetate (50 mL) then added the 2-hydrazinylpyrazine (3.76 g) and stirred for 5 min. Reaction mixture was cooled to 0° C. and diisopropyl ethyl amine (16.63 ml) and then Propylphosphonic anhydride ($T_3P$, 33.31 mL) was added at 0° C. and stirred the reaction mixture for 2.5 hours at the same temperature. After completion of the reaction, the reaction mixture was quenched with cold water (100 mL) and extracted the product with ethyl acetate (2×150 mL). The combined organic layer was dried over sodium sulphate and evaporated the solvent under vacuum at 40° C. to obtain the crude product as yellow syrup. The obtained crude product was combined with dichloromethane (100 mL) and filtered the solid and washed with dichloromethane (2×50 mL). The solid was dried under vacuum at 40° C. to obtain the title compound with purity by HPLC of 99.86%. Yield: 7 g Example-5: Preparation of Form-Alpha of Selinexor A mixture of amorphous Selinexor (0.2) and 9:1 acetone:water (1 mL) was stirred at 25° C. for 54 hours and filtered the solid and dried in air tray drier at 40° C. for 1 hour 20 minutes to obtain the title compound.

Example-6: Preparation of Form-Beta of Selinexor

A mixture of amorphous Selinexor (0.2) and ethanol (1 mL) was stirred at 25° C. for 54 hours and filtered the solid and dried in air tray drier at 40° C. for 1 hour to obtain the title compound.

Example-7: Preparation of Form-Gamma of Selinexor

A mixture of amorphous Selinexor (0.2) and water (1 mL) was stirred at 25° C. for 55 hours and filtered the solid and dried in air tray drier at 40° C. for 1 hour 10 minutes to obtain the title compound.

Example-8: Preparation of Form-Delta of Selinexor

A mixture of amorphous Selinexor (500 mg) and methanol (1 mL) was stirred at 25° C. for 45 minutes. Filtered the solid and dried in air tray drier at 30° C. for 1 hour to obtain the title compound.

Example-9: Preparation of Form-Epsilon of Selinexor

A mixture of amorphous Selinexor (500 mg) and ethanol (1 mL) was stirred at 25° C. for 10 minutes. Filtered the solid and dried in air tray drier at 30° C. for 1 hour to obtain the title compound.

Example-10: Preparation of Form-Zeta of Selinexor

A mixture of amorphous Selinexor (1 g), acetic acid (15 mL) and water (25 mL) was stirred at 25° C. for 4.5 hours. Filtered the solid and dried in air tray drier at 30° C. for 1 hour to obtain the title compound.

Example-11: Preparation of Form-Eta of Selinexor

A mixture of Selinexor (1 g) and nitromethane (25 mL) was stirred at 25° C. for 22 hours. Filtered the solid and dried in air tray drier at 30° C. for 1 hour to obtain the title compound.

Example-12: Preparation of Form-Theta of Selinexor

Selinexor (1 g) was dissolved in formic acid (1 mL) at 25° C. to obtain a clear solution. Methyl tert. Butyl ether (25 mL) and hexane (30 mL) were added to the above solution at 25° C. Stirred the reaction mixture for 23 hours at 25° C. and the solid was filtered. The solid was dried in air tray drier at 30° C. for 1 hour to obtain the title compound.

Example-13: Preparation of Form-Iota of Selinexor

A mixture of Selinexor (1 g) and nitromethane (35 mL) was stirred at 25° C. for 3 days. The solid was filtered and dried in air tray drier at 40° C. for 1 hour, 50° C. for 3 hours and 70° C. for 3 hours to obtain the title compound.

Alternate method: A mixture of Selinexor (1 g) and nitromethane (25 mL) was stirred at 25° C. for 18.5 hours. Filtered the solid and dried in air tray drier at 70° C. for 3 hour to obtain the title compound.

Example-14: Preparation of Form-Kappa of Selinexor

A mixture of amorphous Selinexor (1 g) and water (5 mL) was stirred at 25° C. for 30 minutes and filtered the solid to obtain the title compound.

Alternate method: Selinexor (20 g) was dissolved in methanol (200 mL) at 50° C. and filtered the solution to make it particle free. The clear solution was added in to chilled water (1000 mL) at 8° C. and stirred at the same temperature for 30 minutes. Water (300 mL) was added to the reaction mixture and stirred for 15 minutes. The solid was filtered under nitrogen atmosphere to obtain title compound. Yield: 16.5 g

Example-15: Preparation of Form-Lambda of Selinexor

A mixture of amorphous Selinexor (1 g) and glycerol (10 mL) was stirred at 25° C. for 30 minutes. The solid was filtered and dried in air tray drier at 70° C. for 6 hours to obtain the title compound.

Example-16: Preparation of Form-Mu of Selinexor

Selinexor (500 mg) was dissolved in dimethyl formamide (2 mL) at 25° C. and stirred the mixture for 24 hours at 25° C. and the mixture was kept open at 25° C. under atmospheric pressure for slow solvent evaporation for 4 days. The solid was filtered to obtain the title compound.

Example-17: Preparation of Form-Nu of Selinexor

Selinexor (500 mg) was dissolved in dimethyl formamide (2 mL) at 25° C. and stirred the mixture for 24 hours at 25° C. and the mixture was kept open at 25° C. under atmospheric pressure for slow solvent evaporation for 8 days. The solid was filtered to obtain the title compound.

Example-18: Preparation of Form-Xi of Selinexor

A mixture of amorphous Selinexor (1 g) and water (5 mL) was stirred at 25° C. for 30 minutes. Water (5 ml) was added to the mixture at 25° C. and continued stirring at the same temperature for 1 hour. The solid was filtered to obtain form-kappa and dried in air tray drier at 30° C. for 2.5 hours to obtain title compound.

Alternate method: A mixture of amorphous Selinexor (500 mg) and a mixture of water (4.5 mL) and methanol (0.5 mL) was stirred for 15 minutes at 25° C. A mixture of water (2.7 mL) and methanol (0.3 mL) was added to reaction mixture at 25° C. and stirred for 1.5 hours at the same temperature. The solid was filtered to obtain form-kappa and dried in air tray drier at 30° C. for 3 hours to obtain title compound.

Example-19: Preparation of Amorphous Form of Selinexor

Selinexor (0.3 g) was dissolved in methanol (10 mL) at 50° C. The clear solution was evaporated in a rotavapour at 60° C. under vacuum to obtain the title compound. XRD: Amorphous

Example-20: Preparation of Amorphous Form of Selinexor

Selinexor (0.3 g) was dissolved in acetone (10 mL) at 50° C. The clear solution was evaporated in a rotavapour at 60° C. under vacuum to obtain the title compound. XRD: Amorphous

Example-21: Preparation of Amorphous Solid Dispersion of Selinexor and Povidone Selinexor (0.3 g) and povidone K-30 (0.3 g) was dissolved in methanol (15 mL) at 60° C. The clear solution was evaporated in a rotavapour at 60° C. under vacuum to obtain the amorphous solid dispersion. Above obtained solid dispersion (150 mg) was combined with Syloid (75 mg) by gently grinding the mixture in a mortar and pestle for 10 minutes. XRD: Amorphous

Example-22: Preparation of Amorphous Solid Dispersion of Selinexor and HPMC Phthalate Selinexor (0.3 g) and HPMC phthalate (0.3 g) was dissolved in methanol (15 mL) at 60° C. The clear solution was evaporated in a rotavapour at 60° C. under vacuum to obtain the amorphous solid dispersion. Above obtained solid dispersion (500 mg) was combined with Syloid (500 mg) by gently grinding the mixture in a mortar and pestle for 10 minutes. XRD: Amorphous

Example-23: Preparation of Amorphous Form of Selinexor

Selinexor (1 g) was dissolved in methanol (30 mL) at 55° C. and evaporated the solution under reduced pressure in rotavapour at the same temperature to obtain amorphous Selinexor. Amorphous Selinexor (0.7 g) was combined with Syloid (0.7 g) and blended the mixture in rotavapour at 28° C. for 30 minutes. XRD: Amorphous

Example-24: Preparation of Amorphous Form of Selinexor

Selinexor (10 g) was dissolved in methanol (300 mL) at 25° C. and evaporated the solution under reduced pressure in rotavapour at the 50° C. to obtain amorphous Selinexor and dried the solid at 60° C. for 10 minutes to obtain title compound.

The invention claimed is:

1. A crystalline form of Selinexor, wherein the crystalline form of Selinexor is selected from group consisting of crystalline Form-Delta, characterized by a PXRD pattern comprising the peaks at 6.11, 12.16, 13.00, 20.28 and 24.43 ±0.2° 2θ, crystalline Form-Epsilon, characterized by a PXRD pattern comprising peaks at 5.87, 11.72, 17.61, 18.68, 20.50, 22.78, 23.20, 23.53 and 23.97 ±0.2° 2θ, crystalline Form-Zeta characterized by a PXRD pattern comprising peaks at 4.86, 6.99, 7.74, 10.86, 15.50 and 19.47 ±0.2° 2θ, crystalline Form-Eta characterized by a PXRD pattern comprising peaks at 3.54, 7.03, 9.91, 11.59, 19.84, 20.44 and 21.64 ±0.2° 2θ, crystalline Form-Theta characterized by a PXRD pattern comprising peaks at 6.96, 13.92, 20.95 and 22.82 ±0.2° 2θ, crystalline Form-Iota characterized by a PXRD pattern comprising peaks at 3.69, 7.33, 11.01, 14.66, 16.19 and 18.36 ±0.2° 2θ, crystalline Form-Kappa characterized by a PXRD pattern comprising peaks at 3.22, 11.71, 12.56, 14.42 and 25.20 ±0.2° 2θ, crystalline Form-Lambda characterized by a PXRD pattern comprising peaks at 12.61, 19.00, 19.95 and 21.29 ±0.2° 2θ, crystalline Form-Mu characterized by a PXRD pattern comprising peaks at 9.31, 17.45, 17.85 and 22.72 ±0.2° 2θ, crystalline Form-Nu characterized by a PXRD pattern comprising peaks at 10.75, 17.52, 21.84, 22.16 and 22.38 ±0.2° 2θ, and crystalline Form-Xi characterized by a PXRD pattern comprising peaks at 10.54, 11.68, 12.72 and 24.56 ±0.2° 2θ.

2. A pharmaceutical composition comprising the crystalline form of Selinexor of claim 1 and at least one pharmaceutically acceptable excipient, wherein the crystalline form of Selinexor is selected from group consisting of crystalline Form-Delta, Form-Epsilon, Form-Zeta, Form-Eta, Form-Theta, Form-Iota, Form-Kappa, Form-Lambda, Form-Mu, Form-Nu, and Form-Xi of Selinexor.

3. A process for preparing the crystalline Form Delta of Selinexor of claim 1, which comprises:
   a) combining Selinexor with methanol;
   b) stirring the mixture of step a); and
   c) isolating crystalline Form-Delta of Selinexor.

4. A process for preparing the crystalline Form Epsilon of Selinexor of claim 1, which comprises:
   a) combining Selinexor with ethanol;
   b) stirring the mixture of step a); and
   c) isolating crystalline Form-Epsilon of Selinexor.

5. A process for preparing the crystalline Form Zeta of Selinexor of claim 1, which comprises:
   a) combining Selinexor with acetic acid and water;
   b) stirring the mixture of step a); and
   c) isolating crystalline Form-Zeta of Selinexor.

6. A process for preparing the crystalline Form Eta of Selinexor of claim 1, which comprises:
   a) combining Selinexor with nitromethane;
   b) stirring the mixture of step a); and
   c) isolating crystalline Form-Eta of Selinexor.

7. A process for preparing the crystalline Form Theta of Selinexor of claim 1, which comprises:
   a) providing a solution of Selinexor in formic acid;
   b) contacting the solution of step a) with an anti-solvent; and
   c) isolating crystalline Form-Theta of Selinexor.

8. A process for preparing the crystalline Form Iota of Selinexor of claim 1, which comprises a step of drying crystalline Form Eta of Selinexor.

9. A process for preparing the crystalline Form Kappa of Selinexor of claim 1, which comprises:
   a) combining Selinexor with water;
   b) stirring the mixture of step a); and
   c) isolating crystalline Form-Kappa of Selinexor.

10. A process for preparing the crystalline Form Kappa of Selinexor of claim 1, which comprises:
    a) providing a solution of Selinexor in methanol;
    b) contacting the solution of step a) with water; and
    c) isolating crystalline Form-Kappa of Selinexor.

11. A process for preparing the crystalline Form Lambda of Selinexor of claim 1, which comprises:
    a) combining Selinexor with glycerol;
    b) stirring the mixture of step a); and
    c) isolating crystalline Form-Lambda of Selinexor.

12. A process for preparing the crystalline Form Mu of Selinexor of claim 1, which comprises:
    a) combining Selinexor with dimethyl formamide;
    b) stirring the mixture of step a); and
    c) isolating crystalline Form-Mu of Selinexor.

13. A process for preparing the crystalline Form Nu of Selinexor of claim 1, which comprises:

a) combining Selinexor with dimethylacetamide;
b) stirring the mixture of step a); and
c) isolating crystalline Form-Nu of Selinexor.

14. A process for preparing the crystalline Form Xi of Selinexor of claim 1, which comprises a step of drying crystalline Form-kappa of Selinexor.

15. A process for preparing a crystalline Form Alpha of Selinexor, which comprises:
a) combining Selinexor with acetone: water mixture;
b) stirring the mixture of step a); and
c) isolating crystalline Form-Alpha of Selinexor.

16. A process for the preparation of crystalline form of Selinexor of claim 1, or a solvate thereof, comprising a step of converting amorphous Selinexor to crystalline form of Selinexor or a solvate thereof.

* * * * *